United States Patent
Iwawaki et al.

(10) Patent No.: US 11,196,006 B2
(45) Date of Patent: Dec. 7, 2021

(54) ORGANIC COMPOUND AND ORGANIC LIGHT-EMITTING ELEMENT

(71) Applicant: CANON KABUSHIKI KAISHA, Tokyo (JP)

(72) Inventors: Hironobu Iwawaki, Yokohama (JP); Jun Kamatani, Tokyo (JP); Naoki Yamada, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/586,566

(22) Filed: Sep. 27, 2019

(65) Prior Publication Data

US 2020/0111963 A1 Apr. 9, 2020

(30) Foreign Application Priority Data

Oct. 3, 2018 (JP) .............................. JP2018-187929

(51) Int. Cl.

| | | |
|---|---|---|
| *C07D 209/86* | (2006.01) | |
| *H01L 51/00* | (2006.01) | |
| *C09K 11/06* | (2006.01) | |
| *C07D 213/06* | (2006.01) | |
| *C07D 307/91* | (2006.01) | |
| *G03B 13/02* | (2021.01) | |
| *F21V 23/02* | (2006.01) | |
| *F21S 43/145* | (2018.01) | |
| *H04N 5/225* | (2006.01) | |
| *G09G 3/20* | (2006.01) | |
| *C07C 13/62* | (2006.01) | |
| *H04B 1/3827* | (2015.01) | |
| *H01L 51/50* | (2006.01) | |
| *H01L 27/32* | (2006.01) | |
| *F21Y 115/15* | (2016.01) | |
| *F21W 103/35* | (2018.01) | |

(52) U.S. Cl.
CPC .......... *H01L 51/0056* (2013.01); *C07C 13/62* (2013.01); *C07D 213/06* (2013.01); *C07D 307/91* (2013.01); *C09K 11/06* (2013.01); *F21S 43/145* (2018.01); *F21V 23/02* (2013.01); *G03B 13/02* (2013.01); *G09G 3/2003* (2013.01); *H01L 51/0067* (2013.01); *H01L 51/0073* (2013.01); *H04N 5/2254* (2013.01); *C07C 2603/54* (2017.05); *C09K 2211/1011* (2013.01); *C09K 2211/1018* (2013.01); *F21W 2103/35* (2018.01); *F21Y 2115/15* (2016.08); *H01L 27/322* (2013.01); *H01L 51/504* (2013.01); *H01L 51/5012* (2013.01); *H04B 1/3827* (2013.01)

(58) Field of Classification Search
CPC .................................................. H01L 51/0056
USPC ............................................................ 585/26
See application file for complete search history.

(56) References Cited

U.S. PATENT DOCUMENTS

| | | | | |
|---|---|---|---|---|
| 8,822,043 B2 * | 9/2014 | Kamatani | ............... | C07C 13/62 428/690 |
| 8,963,813 B2 * | 2/2015 | Kamatani | ............ | C07D 215/06 345/76 |

FOREIGN PATENT DOCUMENTS

| | | |
|---|---|---|
| JP | 2011-011994 A | 1/2011 |
| JP | 2013-043846 A | 3/2013 |

OTHER PUBLICATIONS

Dorwald F. A. Side Reactions in Organic Synthesis, 2005, Wiley: VCH, Weinheim p. IX of Preface p. 1-15.*
Jianzhong, Chinese Science Bulletin 2004 vol. 49 No. 8, 797-802.*

* cited by examiner

*Primary Examiner* — Nizal S Chandrakumar
(74) *Attorney, Agent, or Firm* — Canon U.S.A., Inc., IP Division

(57) ABSTRACT

An organic compound that emits red light having a long wavelength and that is represented by formula [1] below. In the formula [1], $R_1$ to $R_{24}$ are each independently selected from a hydrogen atom or a substituent.

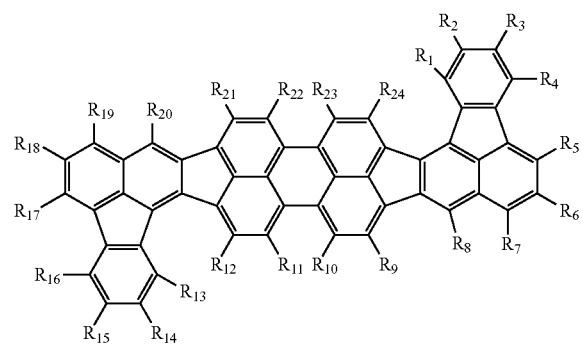

[1]

20 Claims, 6 Drawing Sheets

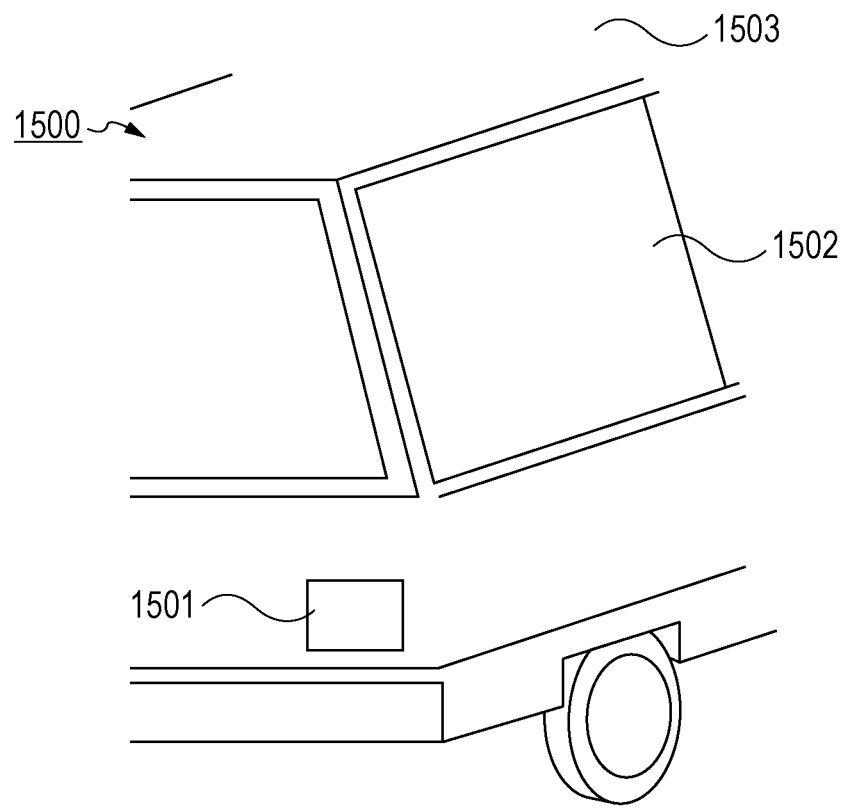

ORGANIC COMPOUND AND ORGANIC LIGHT-EMITTING ELEMENT

BACKGROUND

Field of the Invention

The present disclosure relates to an organic compound and an organic light-emitting element using the organic compound.

Description of the Related Art

An organic light-emitting element (organic electroluminescence element (organic EL element)) is an electronic element that includes a pair of electrodes and an organic compound layer disposed between the electrodes. Electrons and holes are injected from the pair of electrodes to thereby generate excitons of a light-emitting organic compound in the organic compound layer. The organic light-emitting element emits light when the excitons return to their ground state.

Recently, there have been remarkable progress in organic light-emitting elements. For example, it is possible to realize a low driving voltage, various emission wavelengths, high-speed response, and reductions in the thickness and weight of light-emitting devices.

The standards of sRGB and AdobeRGB are used as a color reproduction range used in displays, and materials that reproduce such colors have been desired. Recently, BT-2020 has been proposed as a standard that further expands the color reproduction range.

Light-emitting organic compounds have been actively created to date. This is because the creation of compounds having good light emission characteristics is important to provide high-performance organic light-emitting elements. An example of a compound that has been created to date is a compound 1-A disclosed in Japanese Patent Laid-Open No. 2013-043846 (hereinafter referred to as PTL 1).

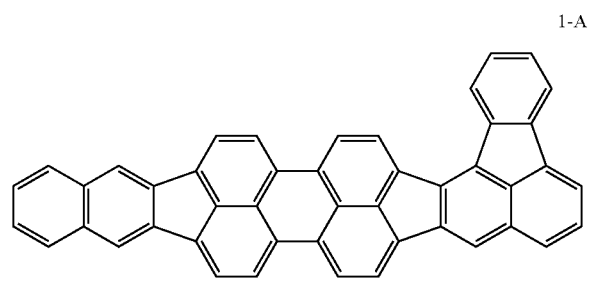

1-A

An organic light-emitting element using the compound disclosed in PTL 1 is difficult to reproduce chromaticity coordinates (0.71, 0.29) of red in the color reproduction range of BT-2020. Thus, a compound that emits red light at a longer wavelength has been desired.

SUMMARY

The present disclosure provides an organic compound that emits red light having a longer wavelength. The present disclosure further provides an organic light-emitting element having good light emission efficiency and driving durability.

An organic compound according to an embodiment of the present disclosure is represented by formula [1] below.

[1]

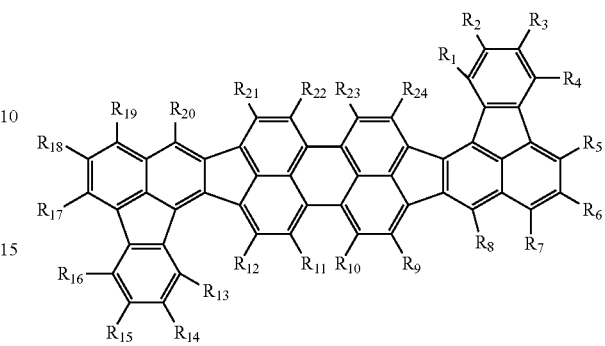

In the formula [1], $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

Further features of the present disclosure will become apparent from the following description of exemplary embodiments with reference to the attached drawings.

BRIEF DESCRIPTION OF THE DRAWINGS

FIG. 7 is a schematic view illustrating an example of a moving object according to the present embodiment.

DESCRIPTION OF THE EMBODIMENTS

Organic Compound

Figure 1:
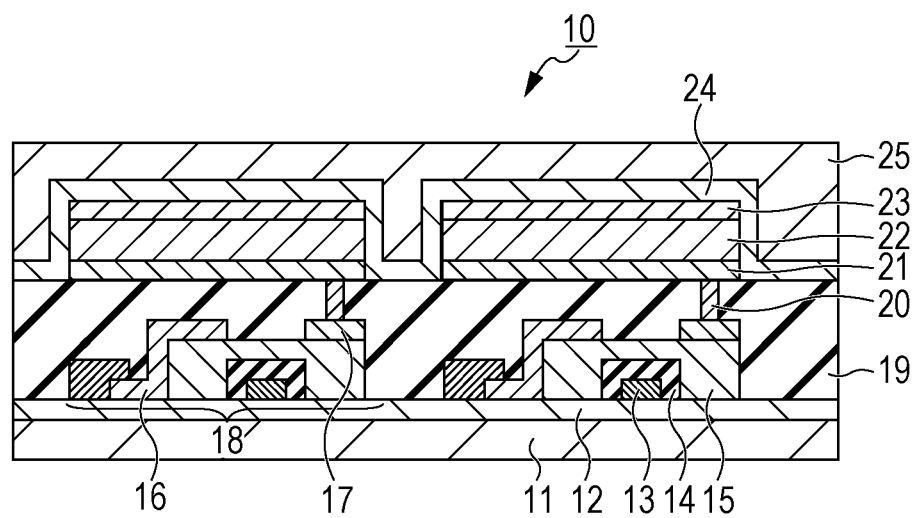
FIG. 1 is a schematic sectional view illustrating an example of a display device according to the present embodiment.

An organic compound according to an embodiment of the present disclosure will now be described. The organic compound according to the present embodiment is represented by formula [1] below.

[1]

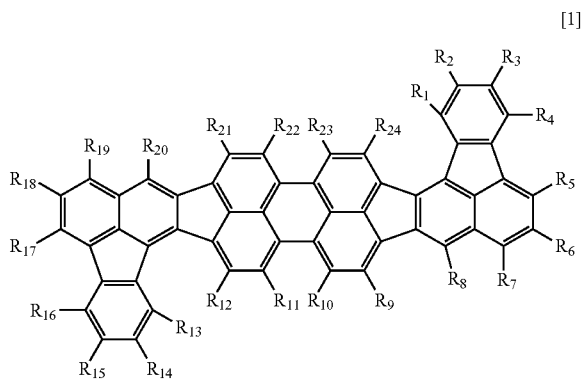

In the formula [1], $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group. Preferably, $R_1$ to $R_{24}$ are each independently selected from the group consisting of a hydrogen atom, a substituted or unsubstituted alkyl group having 1 to 10 carbon atoms, and a substituted or unsubstituted aryl group having 6 to 18 carbon atoms. More preferably, $R_1$ to $R_{24}$ are each independently selected from the group consisting of a hydrogen atom and a substituted or unsubstituted aryl group having 6 to 18 carbon atoms.

The basic skeleton as used herein refers to a skeleton in which $R_1$ to $R_{24}$ of the compound represented by formula [1] are each a hydrogen atom.

Examples of the halogen atom represented by $R_1$ to $R_{24}$ include, but are not limited to, fluorine, chlorine, bromine, and iodine.

The alkyl group represented by $R_1$ to $R_{24}$ may be an alkyl group having 1 to 10 carbon atoms. Examples thereof include, but are not limited to, a methyl group, an ethyl group, a normal propyl group, an isopropyl group, a normal butyl group, a tertiary butyl group, a secondary butyl group, an octyl group, a cyclohexyl group, a 1-adamantyl group, and a 2-adamantyl group. The alkyl group is preferably an alkyl group having 1 to 4 carbon atoms.

The alkoxy group represented by $R_1$ to $R_{24}$ may be an alkoxy group having 1 to 10 carbon atoms. Examples thereof include, but are not limited to, a methoxy group, an ethoxy group, a propoxy group, a 2-ethyl-octyloxy group, and a benzyloxy group. The alkoxy group is preferably an alkoxy group having 1 to 4 carbon atoms.

The amino group represented by $R_1$ to $R_{24}$ may be an amino group having, as a substituent, an alkyl group or an aryl group, or both. Examples thereof include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamimo group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tertiary butylphenyl)amino group, an N-phenyl-N-(4-trifluoromethylphenyl)amino group, and an N-piperidyl group.

The aryl group represented by $R_1$ to $R_{24}$ may be an aryl group having 6 to 18 carbon atoms. Examples thereof include, but are not limited to, a phenyl group, a naphthyl group, an indenyl group, a biphenyl group, a terphenyl group, a fluorenyl group, a phenanthryl group, and a triphenylenyl group. The aryl group is preferably an aryl group having 6 to 12 carbon atoms.

The heterocyclic group represented by $R_1$ to $R_{24}$ may be a heterocyclic group having 3 to 15 carbon atoms. Examples thereof include, but are not limited to, a pyridyl group, an oxazolyl group, an oxadiazolyl group, a thiazolyl group, a thiadiazolyl group, a carbazolyl group, an acridinyl group, a phenanthrolyl group, a dibenzofuranyl group, and a dibenzothiophenyl group. The heterocyclic group is preferably a heterocyclic group having 3 to 12 carbon atoms.

Examples of the aryloxy group represented by $R_1$ to $R_{24}$ include, but are not limited to, a phenoxy group and a thienyloxy group.

Examples of the silyl group represented by $R_1$ to $R_{24}$ include, but are not limited to, a trimethylsilyl group and a triphenylsilyl group.

Examples of the substituents that may be further contained in the alkyl group, the alkoxy group, the amino group, the aryl group, the heterocyclic group, and the aryloxy group include, but are not limited to, alkyl groups such as a methyl group, an ethyl group, a normal propyl group, an isopropyl group, a normal butyl group, and a tertiary butyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenyl amino group, and a ditolylamino group; alkoxy groups such as a methoxy group, an ethoxy group, and a propoxy group; aryloxy groups such as a phenoxy group, halogen atoms such as fluorine, chlorine, bromine, and iodine; and a cyano group. Examples of the substituents preferably include halogen atoms, substituted or unsubstituted alkyl groups having 1 to 10 carbon atoms, substituted or unsubstituted aryl groups having 6 to 12 carbon atoms, substituted or unsubstituted heterocyclic groups having 3 to 9 carbon atoms, and a cyano group.

Next, a method for synthesizing an organic compound according to the present embodiment will be described. The organic compound according to the present embodiment is synthesized in accordance with, for example, the following reaction scheme.

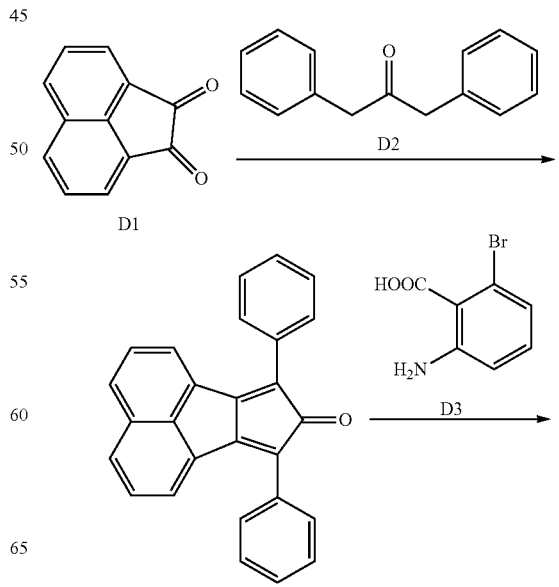

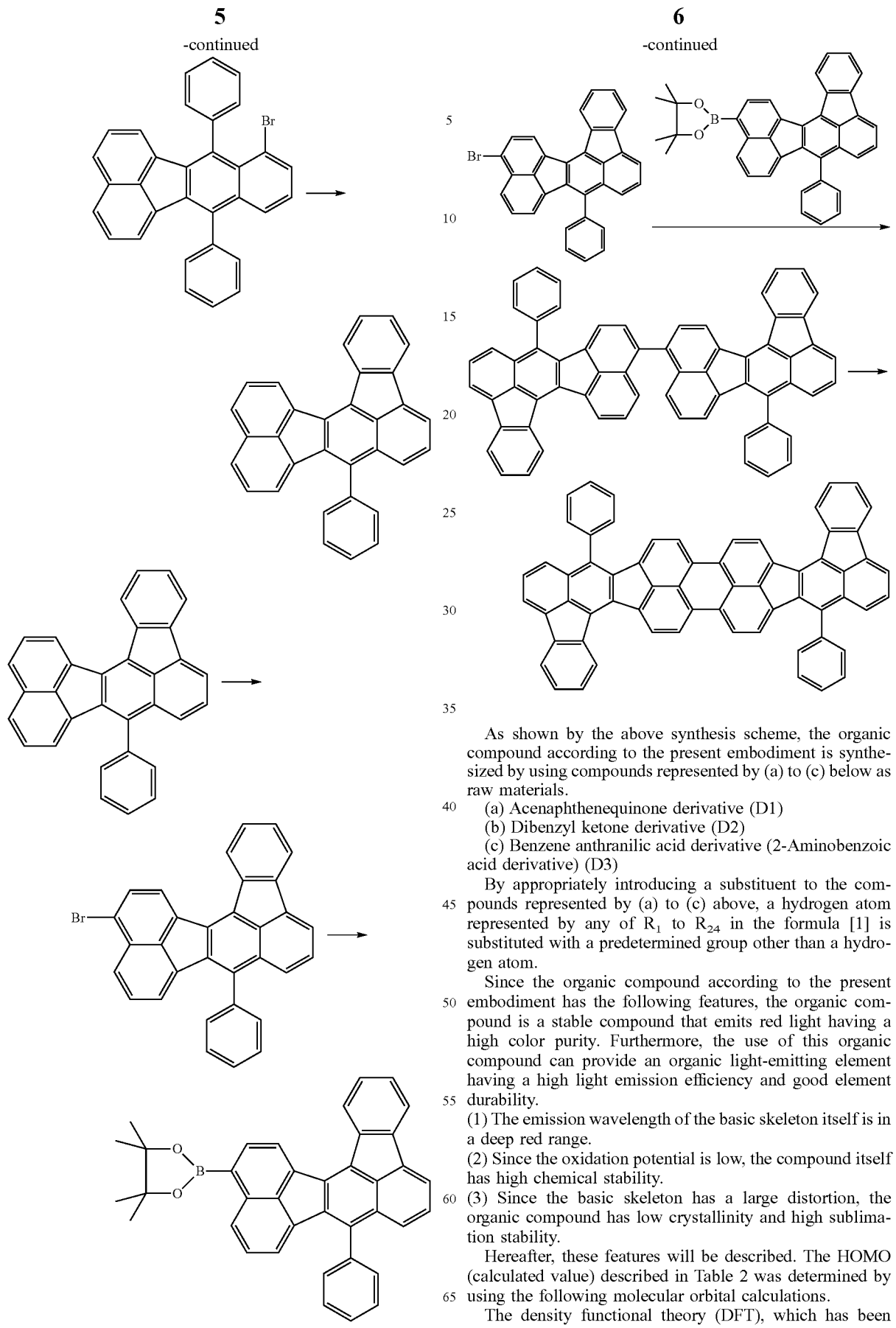

As shown by the above synthesis scheme, the organic compound according to the present embodiment is synthesized by using compounds represented by (a) to (c) below as raw materials.

(a) Acenaphthenequinone derivative (D1)
(b) Dibenzyl ketone derivative (D2)
(c) Benzene anthranilic acid derivative (2-Aminobenzoic acid derivative) (D3)

By appropriately introducing a substituent to the compounds represented by (a) to (c) above, a hydrogen atom represented by any of $R_1$ to $R_{24}$ in the formula [1] is substituted with a predetermined group other than a hydrogen atom.

Since the organic compound according to the present embodiment has the following features, the organic compound is a stable compound that emits red light having a high color purity. Furthermore, the use of this organic compound can provide an organic light-emitting element having a high light emission efficiency and good element durability.

(1) The emission wavelength of the basic skeleton itself is in a deep red range.
(2) Since the oxidation potential is low, the compound itself has high chemical stability.
(3) Since the basic skeleton has a large distortion, the organic compound has low crystallinity and high sublimation stability.

Hereafter, these features will be described. The HOMO (calculated value) described in Table 2 was determined by using the following molecular orbital calculations.

The density functional theory (DFT), which has been currently widely used, was used as a calculation technique of the molecular orbital calculations. The B3LYP was used as the functional, and the 6-31G* was used as the basis function. The molecular orbital calculations were conducted by using Gaussian09 (Gaussian09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010.), which has been currently widely used.

(1) The emission wavelength of the basic skeleton itself is in a deep red range.

In the creation of the organic compound represented by formula [1], the present inventors have focused on the basic skeleton itself. Specifically, the present inventors have attempted to provide an organic compound in which the emission wavelength of the molecule formed of the basic skeleton alone is within a desired wavelength range. In the present embodiment, the desired wavelength range is a red range. Specifically, the maximum emission wavelength is in a range of 610 nm or more and 640 nm or less in a dilute solution.

The emission wavelength range of the organic compound according to the present disclosure will be described while comparing with a reference compound having a structure similar to that of the organic compound according to the present disclosure. Here, the reference compound is comparative compound 1-A which is a compound described in PTL 1 and shown in Table 1. The present inventors compared the emission wavelength of comparative compound 1-A with the emission wavelength of exemplary compound A3 according to the present disclosure. Table 1 shows the results. The measurement of the emission wavelength was conducted by photoluminescence measurement of a diluted toluene solution at an excitation wavelength of 350 nm at room temperature using a fluorescence spectrophotometer F-4500 manufactured by Hitachi, Ltd.

TABLE 1

| | Structural formula | Maximum emission wavelength |
|---|---|---|
| Comparative compound 1-A | | 607 nm |
| Exemplary compound A3 | | 614 nm |

Referring to Table 1, the emission color of comparative compound 1-A is red but is not in the desired wavelength range. In contrast, since exemplary compound A3 has a maximum emission wavelength in the desired range, exemplary compound A3 exhibits an emission color suitable for red in a display standard. The same applies to exemplary compound A1, which is the basic skeleton itself. Accordingly, the basic skeleton according to the present disclosure can exhibit light emission having a high color purity and capable of reproducing deep red. Chromaticity coordinates of red will be described in detail in Examples.

(2) Since the oxidation potential is low, the compound itself has high chemical stability.

In the creation of a material having a desired emission wavelength range, the present inventors have focused on the HOMO energy of molecules. An emission wavelength range on the longer wavelength side means a narrow band gap. To achieve a narrow band gap, it is necessary to make the HOMO energy high or to make the LUMO energy low. Herein, a high HOMO energy means that the energy level is close to the vacuum level, and a low HOMO energy means that the energy level is far from the vacuum level.

For example, a compound in which diphenylamine is bound to a basic skeleton (benzoindenoperylene skeleton) having a fused ring structure, such as comparative compound 1-B shown in Table 2, has an emission wavelength range in a long-wavelength range (maximum emission wavelength: 599 nm). However, the compound is unstable to oxidation because of its high HOMO energy. In contrast, in the organic compound according to the present disclosure, an emission wavelength range in a longer wavelength range is realized so as to lower the HOMO energy level and the LUMO energy level. Specifically, the molecule has been designed to have a fused ring structure in which the conjugation length is extended so that the molecule has four, electron-withdrawing, five-membered rings in the basic skeleton thereof. Therefore, the HOMO energy level and the LUMO energy level are low, that is, the oxidation potential of the compound is low. Accordingly, the organic compound according to the present embodiment is stable to oxidation. A compound having two five-membered rings in the fused structure, such as comparative compound 1-C, has a higher HOMO energy than a compound having four five-membered rings in the fused structure, such as the compound according to the present disclosure.

TABLE 2

| | Structural formula | HOMO (Calculated value) |
|---|---|---|
| Comparative compound 1-B | | −4.69 eV |
| Comparative compound 1-C | | −4.72 eV |
| Exemplary compound A3 | | −4.89 eV |

The basic skeleton of the organic compound according to the present embodiment consists of carbon and has no heteroatom such as a nitrogen atom. This also contributes to the low oxidation potential of the compound itself and is one reason why the organic compound according to the present embodiment is stable to oxidation. Consequently, an organic light-emitting element using this compound has high stability and exhibits good element durability.

(3) Since the basic skeleton has a large distortion, the organic compound has low crystallinity and high sublimation stability.

In the organic compound according to the present disclosure, the conjugation length is extended such that the emission wavelength range of the basic skeleton itself is in a red range. In general, molecules having a long conjugation length have high molecular planarity, resulting in strong molecular packing. Molecular packing is not preferable because it increases crystallinity and causes concentration quenching and a decrease in sublimability. In view of this, the present inventors have focused on the steric distortion of the basic skeleton structures of molecules. In molecules having a large steric distortion, the molecular arrangement is easily disordered in a solid state compared with a case of molecules having a small steric distortion, and therefore, molecular packing, which is an ordered stacking of molecules, is suppressed. In molecules having a large steric distortion, molecular packing is suppressed to decrease crystallinity. Therefore, such molecules having a large steric distortion have high sublimability. According to the structure in the present disclosure, the molecule has a large steric distortion, and the planarity of the molecule is decreased. Therefore, the structure in the present disclosure is disadvantageous to intermolecular stacking, and thus is considered to be a basic skeleton structure advantageous in terms of sublimability. On the other hand, in a structure having very high planarity, which enhances molecular packing, the sublimation temperature is increased to around the decomposition temperature of the compound. Accordingly, the compound is less likely to sublimate and is easily decomposed.

Furthermore, an example of a method for enhancing the effect of suppressing molecular packing includes introducing a substituent other than a hydrogen atom, preferably, a bulky group or a group having a bulky substituent in at least one, preferably, at least two selected from $R_6$, $R_8$, $R_{18}$, and $R_{20}$ of formula [1]. The effect of suppressing molecular packing can be further enhanced by combining the effect of the distortion of the basis skeleton and the effect of introducing a group other than a hydrogen atom. The group other than a hydrogen atom is a halogen atom, a substituted or unsubstituted alkyl group having 1 to 10 carbon atoms, a substituted or unsubstituted alkoxy group having 1 to 10 carbon atoms, a substituted or unsubstituted amino group, a substituted or unsubstituted aryl group having 6 to 18 carbon atoms, a substituted or unsubstituted heterocyclic group having 3 to 15 carbon atoms, a substituted or unsubstituted aryloxy group, a silyl group, or a cyano group. The group other than a hydrogen atom is preferably a substituted or unsubstituted alkyl group having 1 to 10 carbon atoms or a substituted or unsubstituted aryl group having 6 to 18 carbon atoms. Specifically, when the group other than a hydrogen atom is an alkyl group having 1 to 10 carbon atoms, for example, a methyl group, an ethyl group, a propyl group, a butyl group, a hexyl group, or an octyl group is preferred. An isopropyl group or a tertiary butyl group, which is sterically bulky, is particularly preferred. When the group other than a hydrogen atom is an aryl group having 6 to 18 carbon atoms, an aryl group such as a phenyl group or a naphthyl group is preferred. A phenyl group, which has a low molecular weight, is preferred from the viewpoint of sublimability. An aryl group such as a phenyl group having a substituent, e.g., a methyl group, an isopropyl group, or a tertiary butyl group, is preferred. From the above viewpoint, a fluorine atom or an aryl group having a fluorine atom is also preferred as the group other than a hydrogen atom. The group other than a hydrogen atom is preferably introduced because, when the organic compound is used in a method including incorporating the organic compound in a liquid, disposing (applying) the resulting liquid at a predetermined position, and subsequently removing the solvent, properties of the resulting film improve.

Furthermore, as the effect of improvement, the present inventors have attempted to introduce a group that covers a π-conjugated plane. As a result, it has been found that an aryl group having a substituent at an ortho position thereof, the aryl group being introduced as at least one, preferably, at least two selected from $R_6$, $R_8$, $R_{18}$, and $R_{20}$, covers a π-conjugated plane of the basic skeleton and can suppress intermolecular stacking. Examples of the compound having such a structure include an ortho-tolyl compound having a methyl group at an ortho-position of a phenyl group introduced as at least one, preferably, at least two selected from $R_6$, $R_8$, $R_{18}$, and $R_{20}$ and an ortho-biphenyl compound having a phenyl group at an ortho-position of a phenyl group introduced as at least one, preferably, at least two selected from $R_6$, $R_8$, $R_{18}$, and $R_{20}$. A phenyl group has a higher effect of covering the π-conjugated plane than a methyl group and can suppress intermolecular stacking.

Furthermore, by introducing different groups in $R_6$ and $R_8$, and $R_{18}$ and $R_{20}$, the symmetry is further lost, and molecular packing can be suppressed. In particular, when an aryl group such as a phenyl group is introduced in $R_8$ and $R_{20}$, the aryl group is sterically orthogonal to the plane of the basic skeleton, and consequently, a particularly high effect of suppressing molecular packing is achieved. When a bulky group is introduced in $R_6$ and $R_{18}$, the bulky group acts in a direction in which the planarity in the molecular long axis direction is lost. Thus, the effect of suppressing molecular packing can be enhanced. The enhancement of the effect of suppressing molecular packing enables improvement in sublimability and reduction in concentration quenching. The improvement in sublimability can realize a higher purity of a material by sublimation purification and preparation of an organic light-emitting element by vapor deposition. As a result, impurities contained in the organic light-emitting element can be reduced to prevent a decrease in the light emission efficiency and a decrease in driving durability due to impurities. The reduction in concentration quenching is preferred from the viewpoint of improving the light emission efficiency of the organic light-emitting element.

Specific examples of the organic compound according to the present disclosure are shown below. However, the present disclosure is not limited thereto.

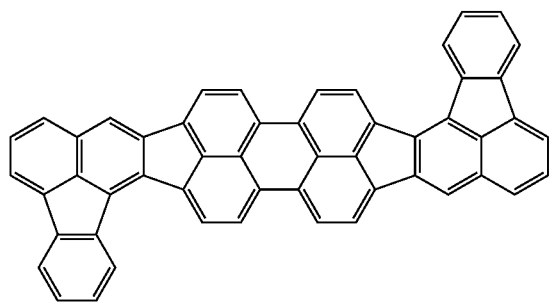
A1
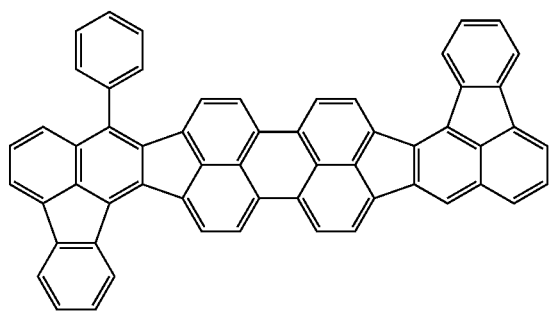
A2
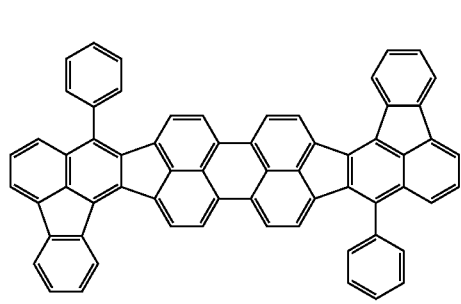
A3
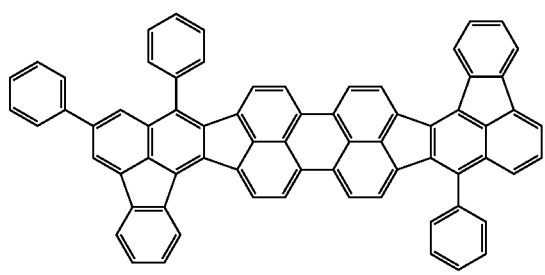
A4
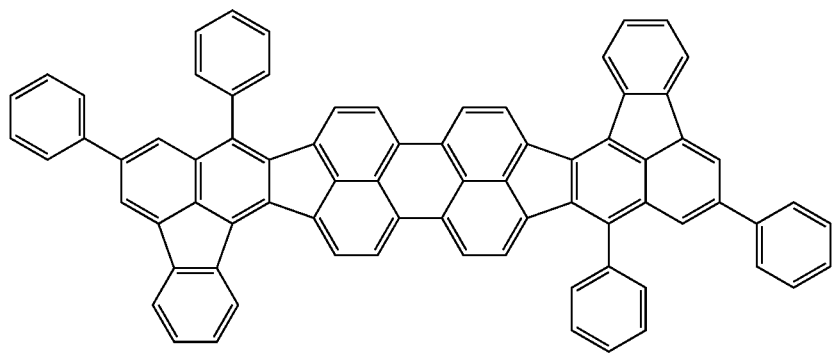
A5
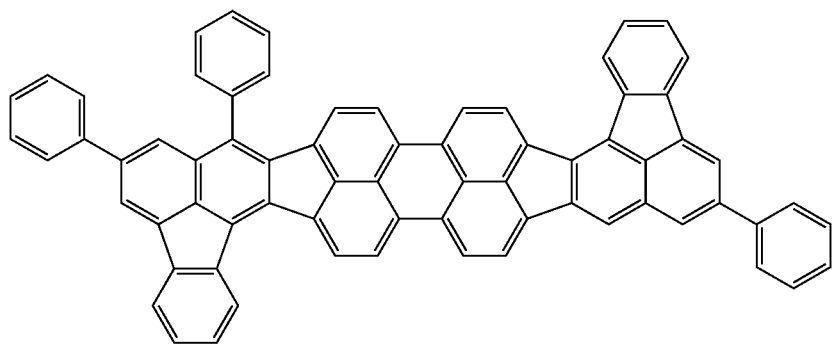
A6

A7
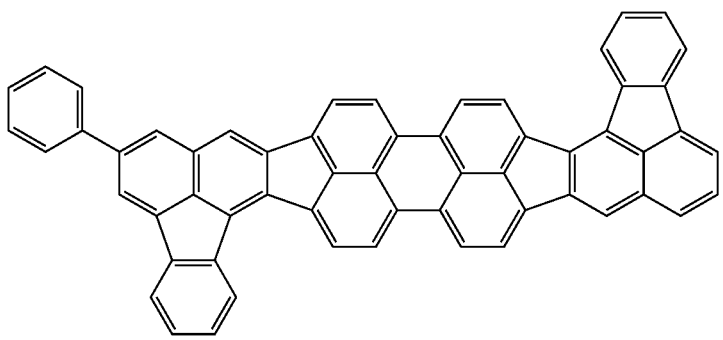
A8
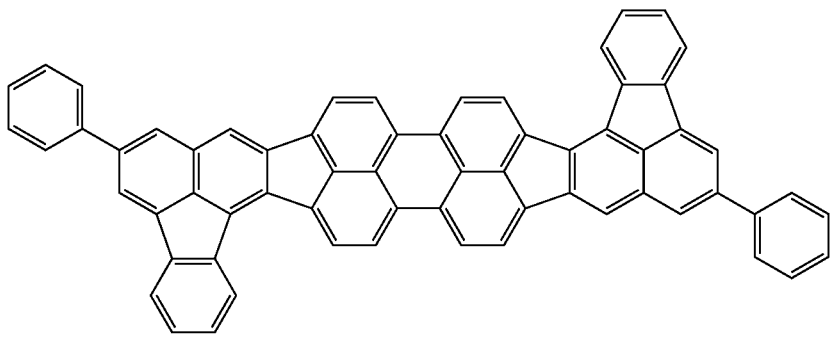
A9
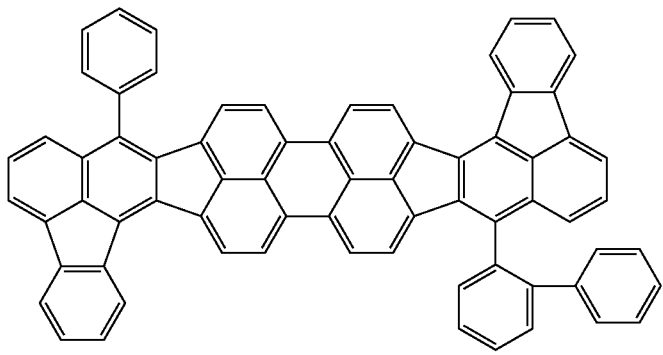
A10
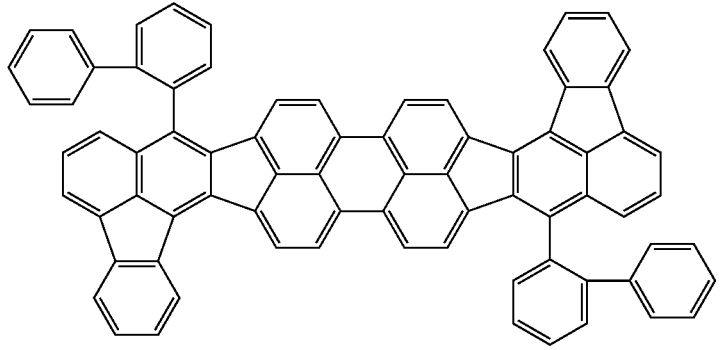

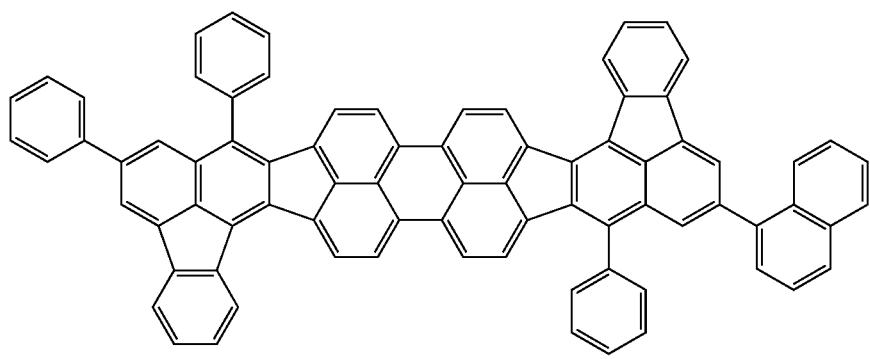
A11
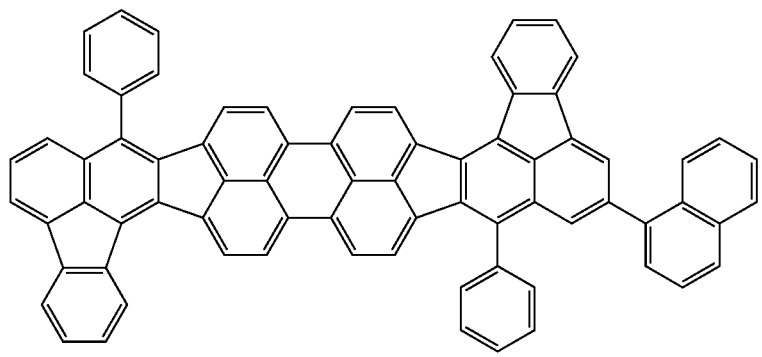
A12
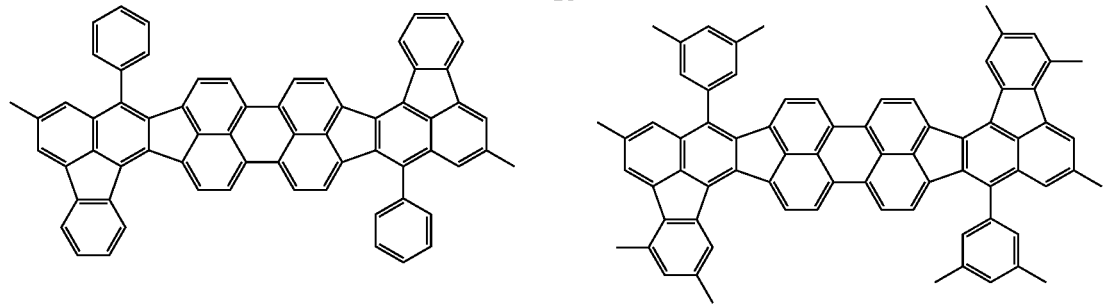
B1　　B2
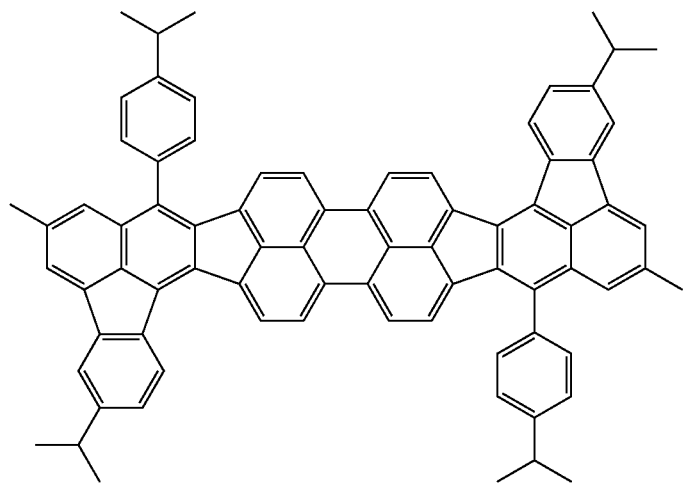
B3

-continued
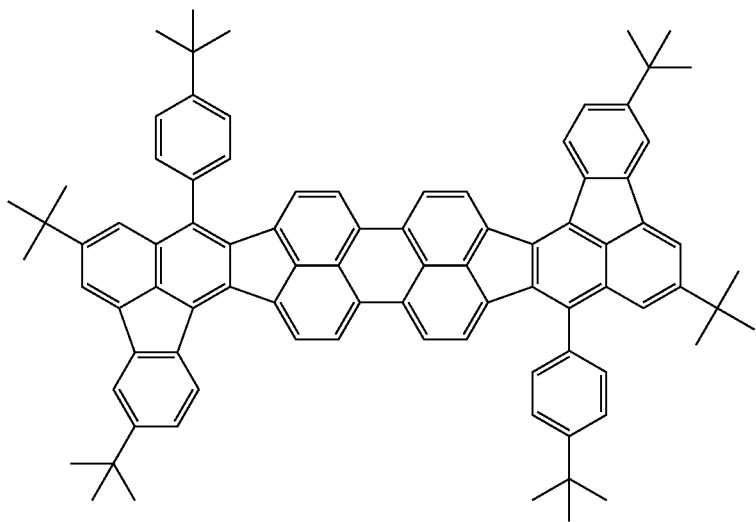
B4
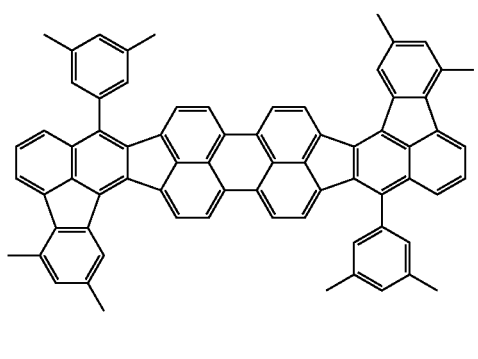
B5
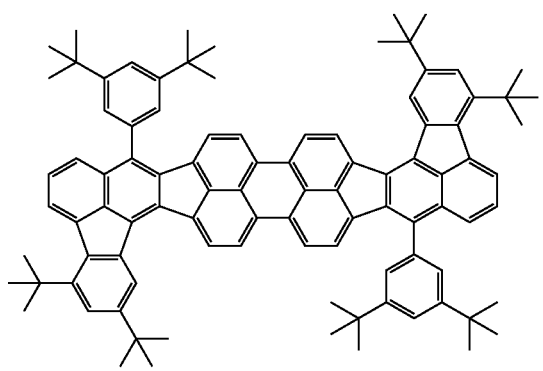
B6
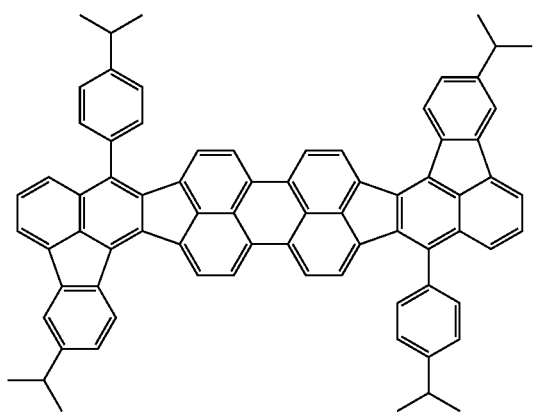
B7
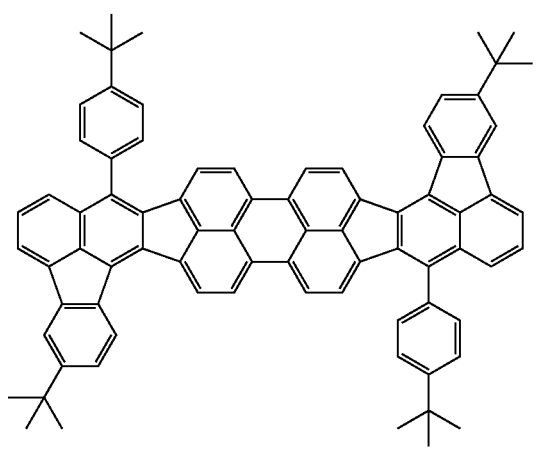
B8

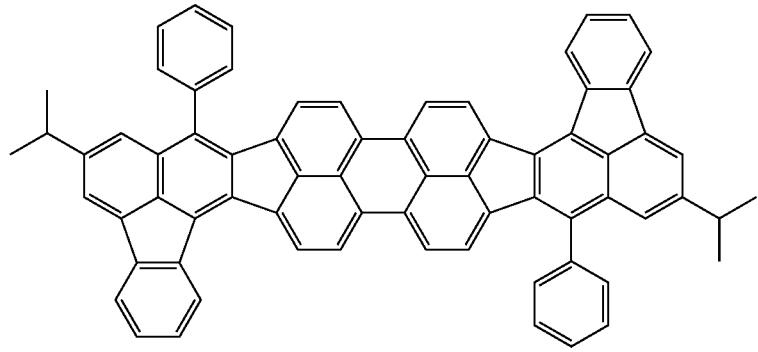
B9
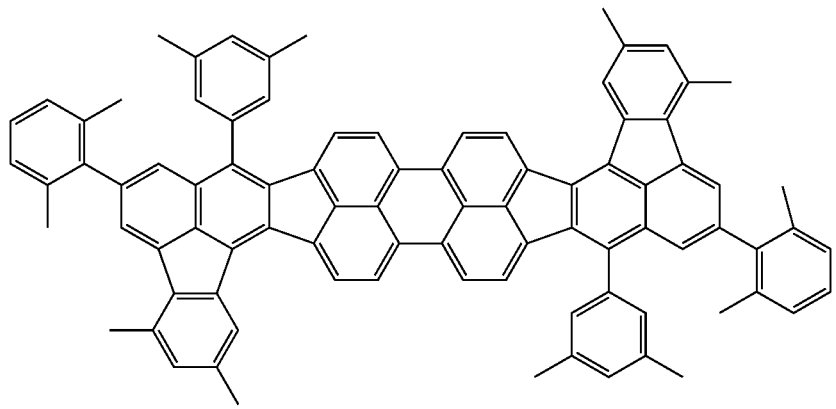
B10
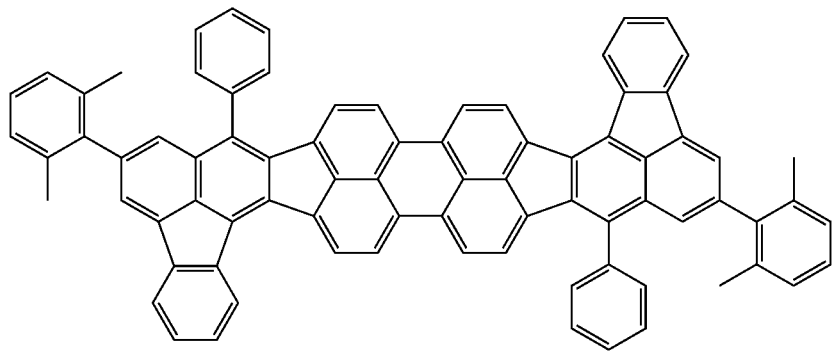
B11
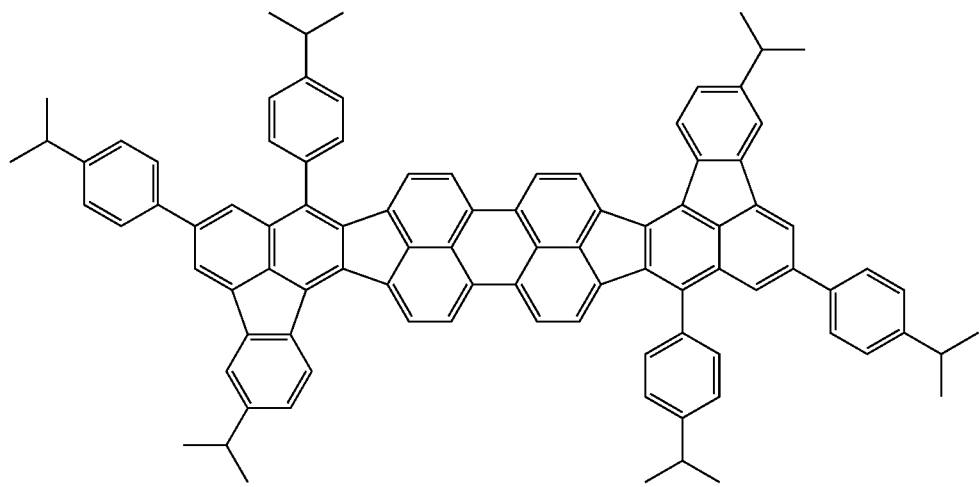
B12

-continued
B13
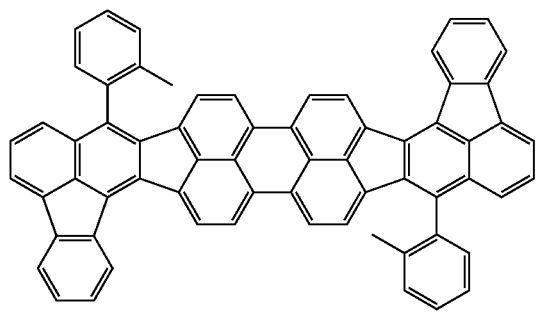
B14
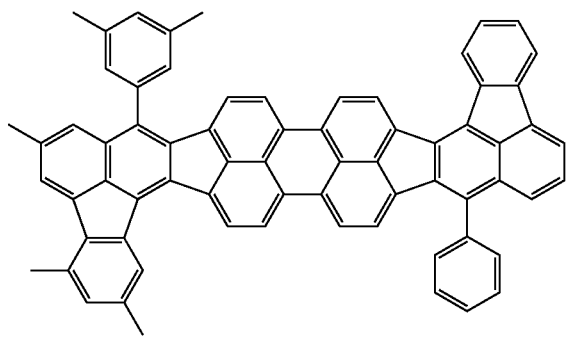
B15
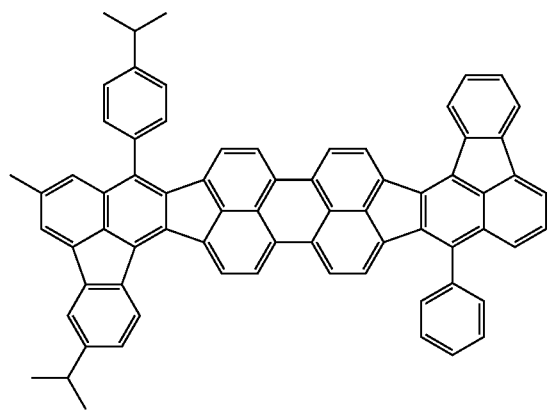
B16
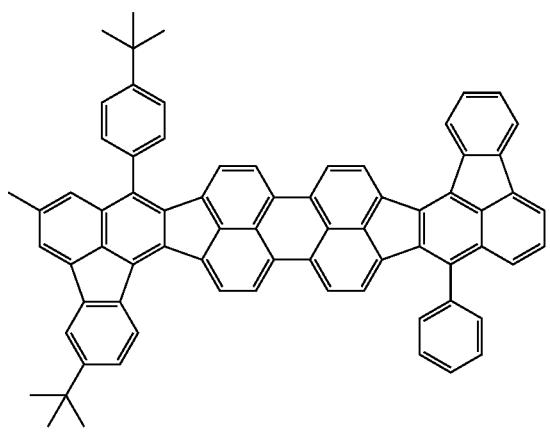
B17
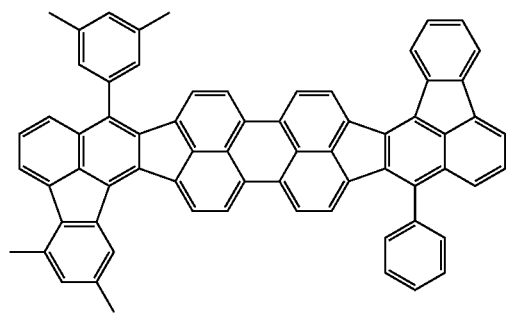
B18
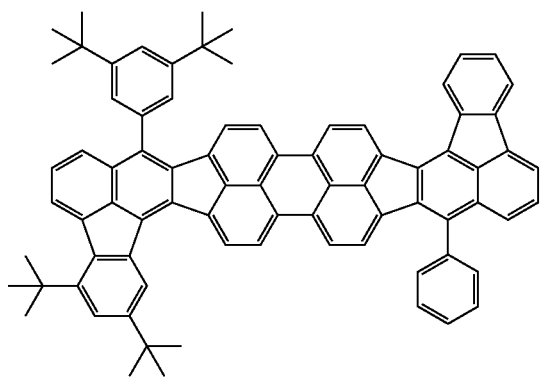

-continued
B19
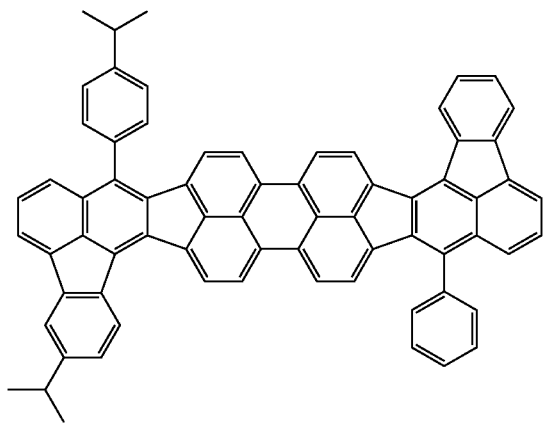
B20
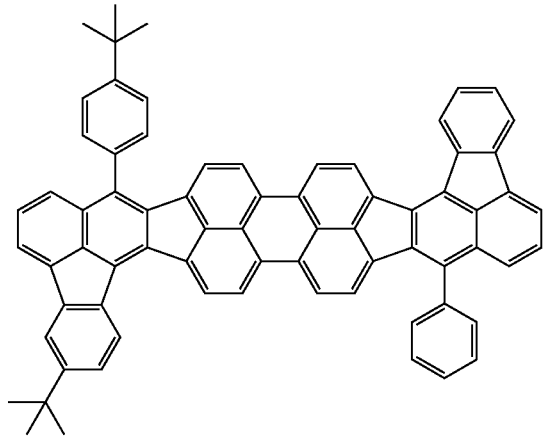
B21
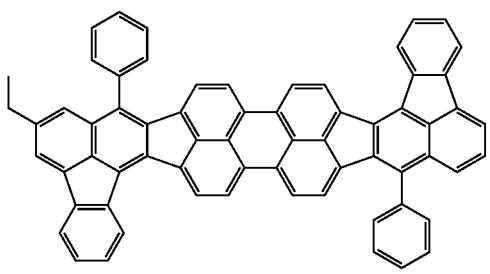
B22
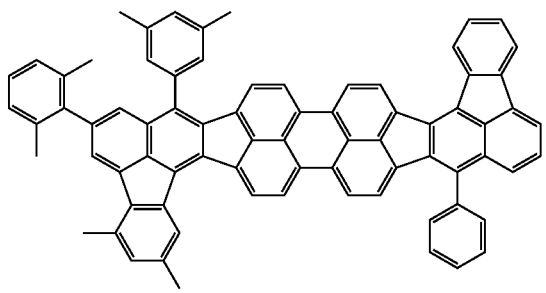
B23
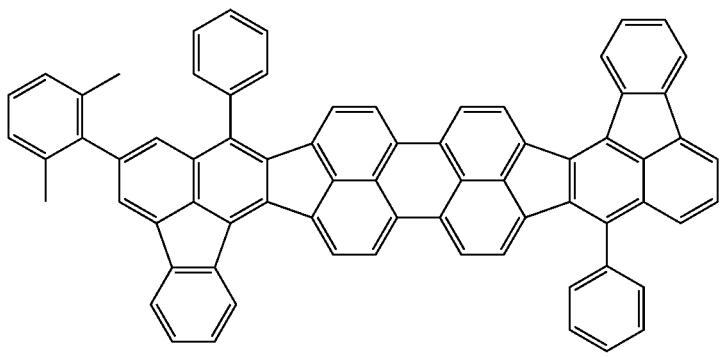
B24
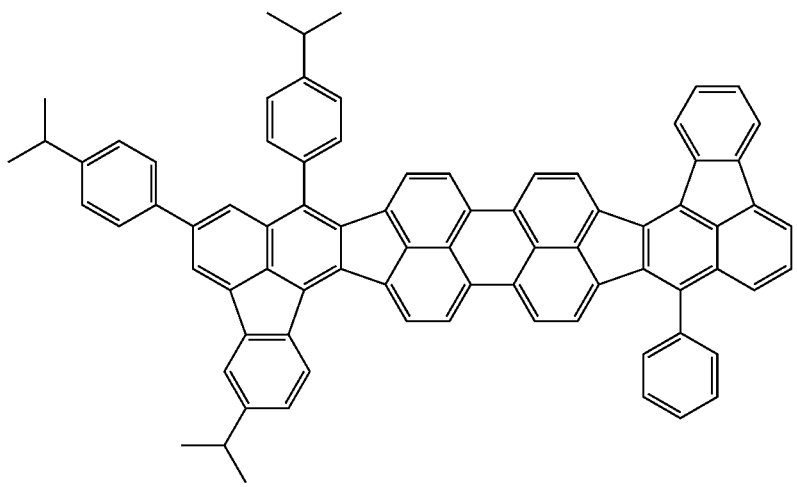

-continued
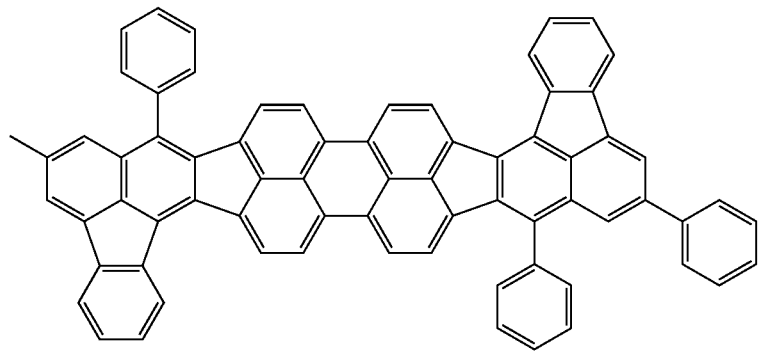
B25
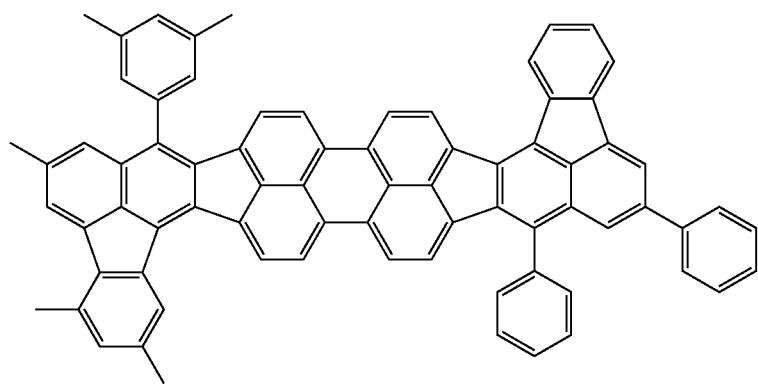
B26
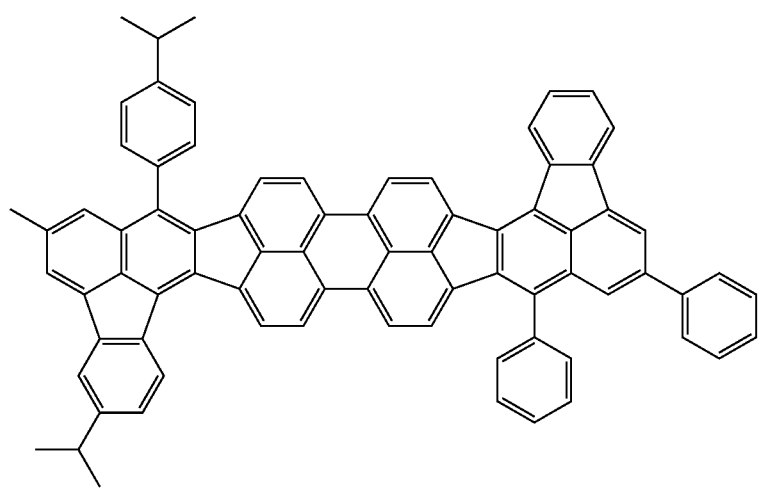
B27

-continued
B28
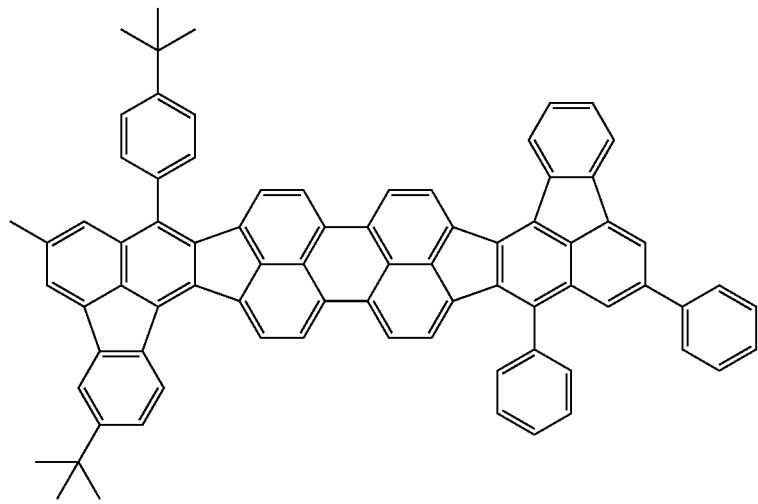
B29
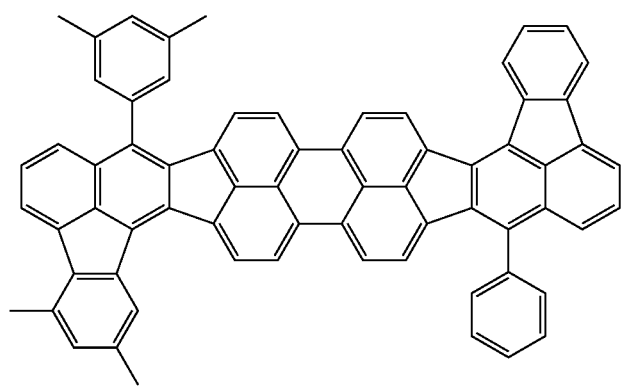
B30
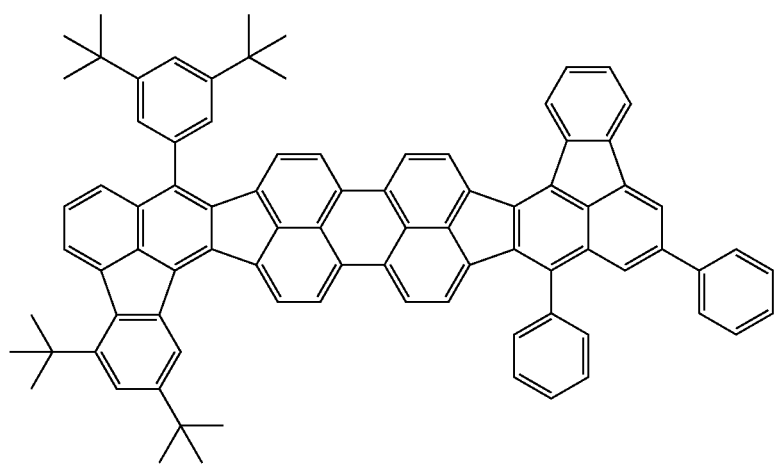

B31
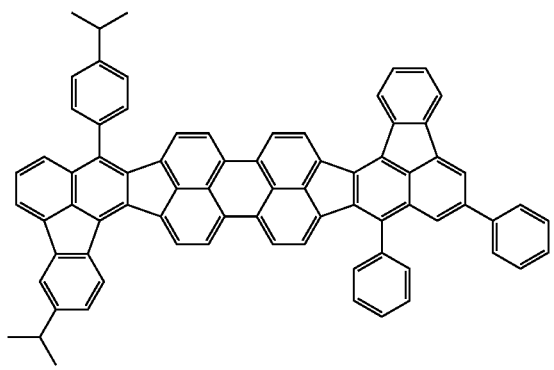
B32
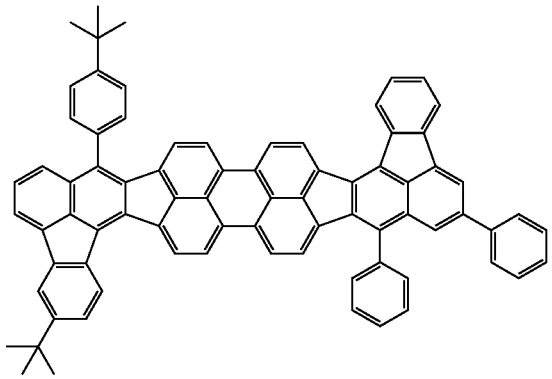
B33
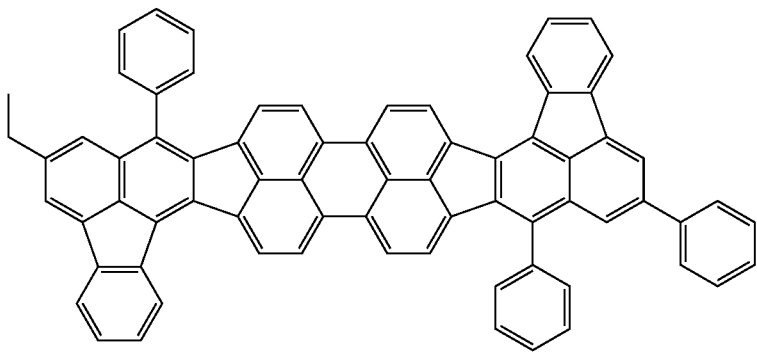
C1
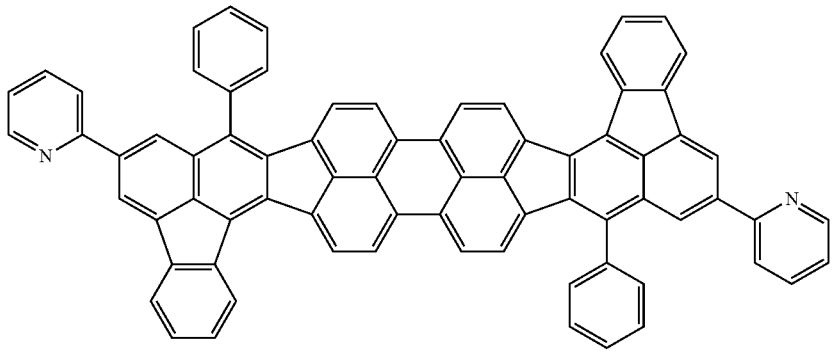
C2
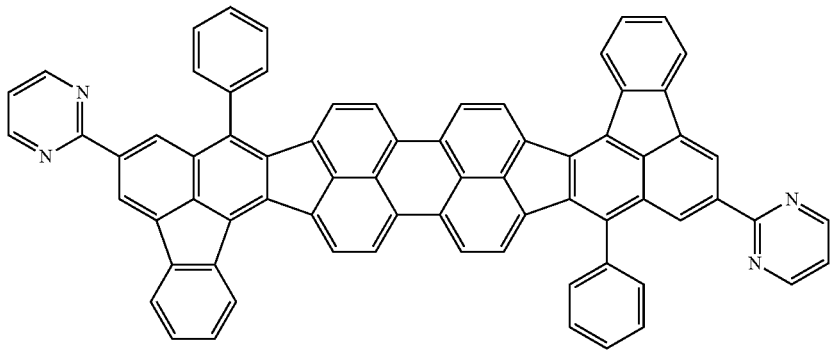

-continued
C3
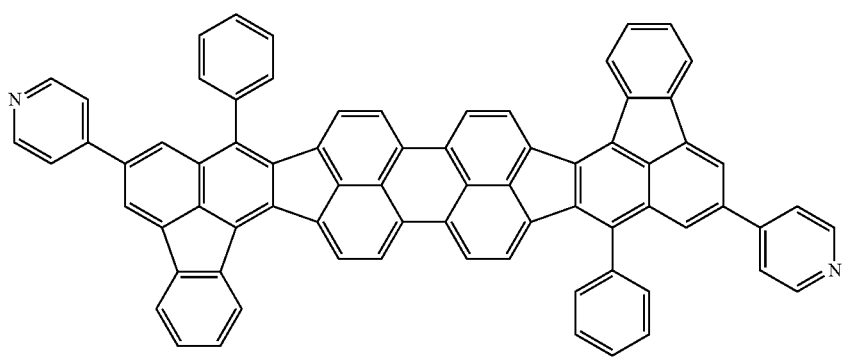
C4
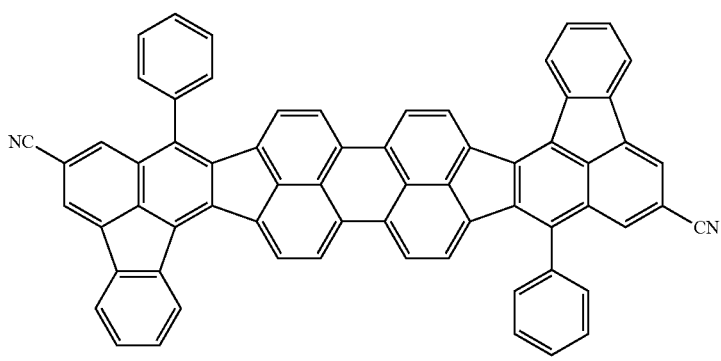
C5
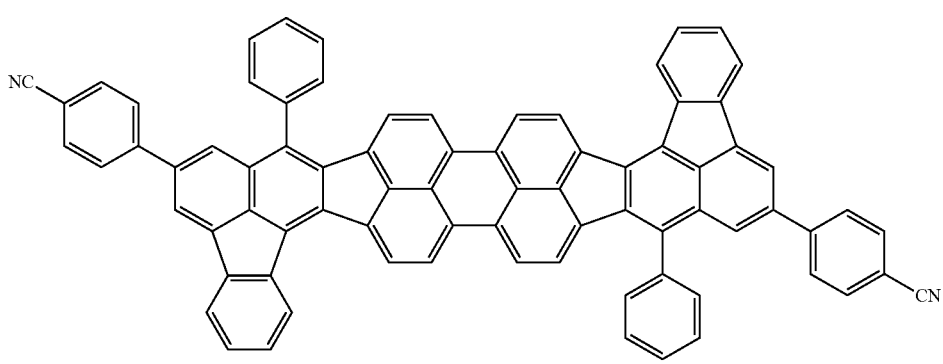
C6
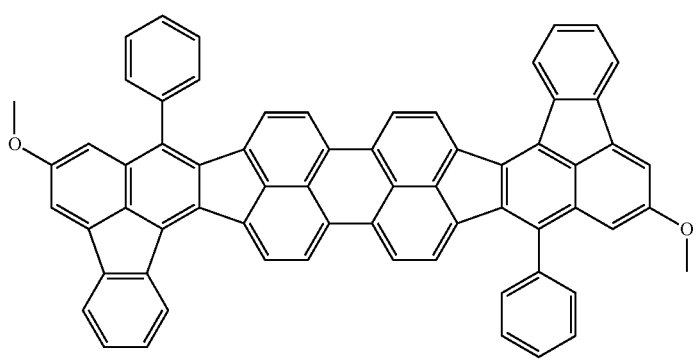

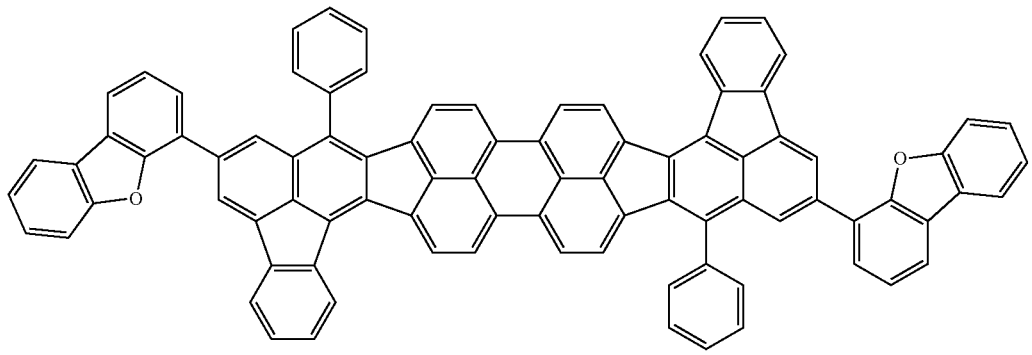

C7

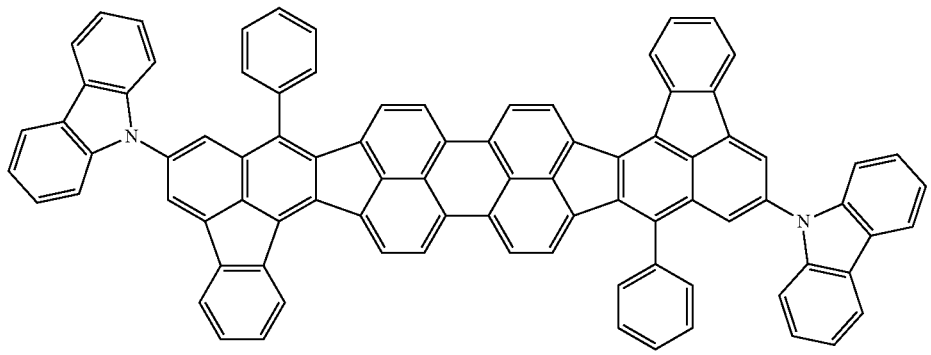

C8

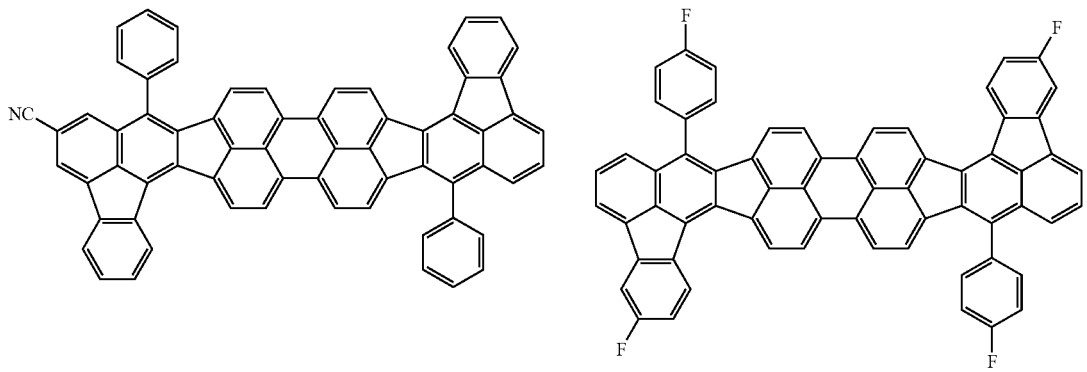

C9

C10

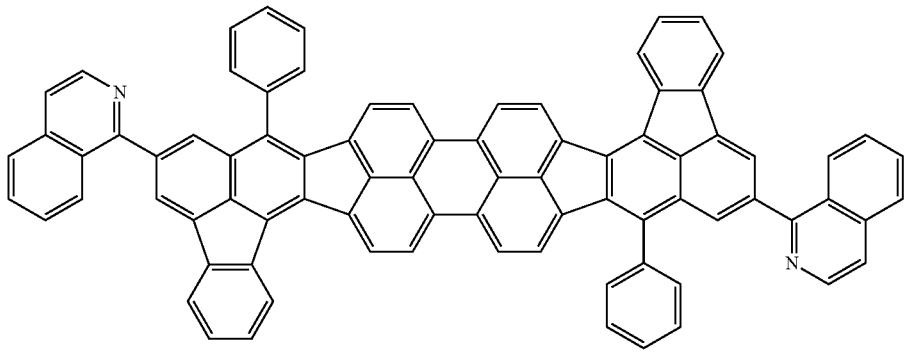

C11

Among the above exemplary compounds, the exemplary compounds belonging to group A are molecules each entirely consisting of carbon with an $sp^2$ hybrid orbital and hydrogen. In general, compounds consisting of carbon with an $sp^2$ hybrid orbital and hydrogen have low HOMO energy levels. Accordingly, the compounds belonging to group A are compounds that have low oxidation potentials, that is, compounds that are stable to oxidation. Accordingly, among the compounds according to the present embodiment, organic compounds consisting of carbon with an $sp^2$ hybrid orbital and hydrogen, that is, the compounds belonging to group A are preferred because of their high molecular stability. More specifically, the compounds belonging to group A can be used as a light-emitting-layer host material, a transport layer, or an injection layer.

Among the above exemplary compounds, the exemplary compounds belonging to group B are each an example in which an alkyl group is introduced. In the compounds in which an alkyl group is introduced, intermolecular stacking is prevented, and a start temperature of sublimation or vapor deposition decreases. When such compounds are used as a light-emitting-layer guest material, concentration quenching can be reduced. Furthermore, since the compounds have improved solubility, the compounds can be used as materials for coating.

Among the above exemplary compounds, the exemplary compounds belonging to group C each have a group containing a heteroatom. In this case, the oxidation potential of the molecule itself is significantly changed, or intermolecular interaction is changed. In compounds in which a nitrogen-containing heterocyclic group or a cyano group is introduced, the effect of withdrawing an electron acts on the basic skeleton. Therefore, these compounds each have a lower HOMO energy level and are more stable to oxidation than the compounds belonging to group A or group B. The organic compounds belonging to group C are useful as electron transport, hole transport, and hole trap light-emitting materials.

Compounds in which an aryl group having 7 or more carbon atoms or a heterocyclic group is introduced have a higher glass transition temperature than compounds in which a phenyl group is introduced. Accordingly, when these compounds are used as a light-emitting-layer host material or a transport layer, a thermally stable amorphous film is formed.

The organic compound according to the present disclosure is a compound that exhibits light emission suitable for red-light emission. Therefore, when the organic compound according to the present disclosure is used as a material of an organic light-emitting element, an organic light-emitting element having good light emission characteristics and excellent durability can be produced.

Organic Light-Emitting Element

Next, an organic light-emitting element of the present embodiment will be described. The organic light-emitting element of the present embodiment includes at least an anode and a cathode, which are a pair of electrodes, and an organic compound layer disposed between the electrodes. In the organic light-emitting element of the present embodiment, the organic compound layer may be formed of a single layer or a layered product including a plurality of layers as long as the organic compound layer includes a light-emitting layer. When the organic compound layer is a layered product including a plurality of layers, the organic compound layer may include, besides a light-emitting layer, for example, a hole injection layer, a hole transport layer, an electron blocking layer, a hole/exciton blocking layer, an electron transport layer, and an electron injection layer. The light-emitting layer may be a single layer or a layered product including a plurality of layers.

In the organic light-emitting element of the present embodiment, at least one layer of the organic compound layer contains the organic compound according to the present embodiment. Specifically, the organic compound according to the present embodiment is contained in any of the hole injection layer, the hole transport layer, the electron blocking layer, the light-emitting layer, the hole/exciton blocking layer, the electron transport layer, and the electron injection layer. The organic compound according to the present embodiment is preferably contained in the light-emitting layer.

When the organic compound according to the present embodiment is contained in a light-emitting layer in the organic light-emitting element of the present embodiment, the light-emitting layer may be a layer consisting of the organic compound according to the present embodiment or a layer that contains the organic compound according to the present embodiment and another compound. When the light-emitting layer is a layer containing the organic compound according to the present embodiment and another compound, the organic compound according to the present embodiment may be used as a host of the light-emitting layer or a guest of the light-emitting layer. Alternatively, the organic compound according to the present embodiment may be used as an assist material that can be contained in the light-emitting layer. Herein, the host refers to, among the compounds that form the light-emitting layer, a compound having the highest mass ratio. The guest refers to, among the compounds that form the light-emitting layer, a compound that has a lower mass ratio than the host and that is responsible for main light emission. The assist material refers to, among the compounds that form the light-emitting layer, a compound that has a lower mass ratio than the host and that assists light emission of the guest. The assist material is also referred to as a second host.

When the organic compound according to the present embodiment is used as the guest of the light-emitting layer, the concentration of the guest is preferably 0.01% by mass or more and 20% by mass or less and more preferably 0.1% by mass or more and 5% by mass or less of the total of the light-emitting layer.

When the organic compound according to the present embodiment is used as the guest of the light-emitting layer, a material having a higher LUMO energy than the organic compound according to the present embodiment (a material having a LUMO energy level closer to the vacuum level) may be used as the host. This is because the organic compound according to the present embodiment has a low LUMO energy, and thus the use of a material having a higher LUMO energy than the organic compound of the present embodiment as the host enables the organic compound according to the present embodiment to receive a larger part of the electrons supplied to the host of the light-emitting layer.

As a results of various studies, the present inventors have found that the use of the organic compound according to the present embodiment as the host or the guest of a light-emitting layer, in particular, as the guest of a light-emitting layer provides an element that produces optical output with high efficiently and high luminance and that has extremely high durability. This light-emitting layer may be formed of a single layer or may have a multilayer structure. The light-emitting layer may contain another light-emitting material having another emission color so as to emit light having a color mixed with red which is the emission color of the present embodiment. The multilayer structure refers to a state where the light-emitting layer and another light-emitting layer are stacked. In such a case, the emission color of the organic light-emitting element is not limited to red. More specifically, the emission color may be white or intermediate color. When the emission color is white, the other light-emitting layer emits light having a color other than red, specifically, blue or green. The light-emitting layer is formed by a method such as vapor deposition or coating. Details of the method will be more specifically described in Examples below.

The organic compound according to the present embodiment can be used as a material that forms an organic compound layer other than the light-emitting layer included in an organic light-emitting element of the present embodiment. Specifically, the organic compound according to the present embodiment may be used as a material that forms an electron transport layer, an electron injection layer, a hole transport layer, a hole injection layer, a hole blocking layer, or the like. In such a case, the emission color of the organic light-emitting element is not limited to red. More specifically, the emission color may be white or intermediate color.

Herein, the organic compound according to the present embodiment may be used in combination with a known low-molecular-weight or high-molecular-weight hole injection compound or hole transport compound, a compound serving as the host, a light-emitting compound, an electron injection compound, an electron transport compound, and the like, as required. Examples of these compounds will be described below.

A hole injection/transport material is preferably a material having a high hole mobility so as to facilitate hole injection from the anode and to enable the injected holes to be transported to the light-emitting layer. From the viewpoint of suppressing deterioration of the film quality such as crystallization in the organic light-emitting element, a material having a high glass transition temperature is preferred. Examples of the low-molecular-weight or high-molecular-weight material having a hole injection/transport performance include triarylamine derivatives, arylcarbazole derivatives, phenylenediamine derivatives, stilbene derivatives, phthalocyanine derivatives, porphyrin derivatives, poly(vinylcarbazole), poly(thiophene), and other electrically conductive polymers. The above hole injection/transport material is also suitably used as an electron blocking layer. Specific examples of the compound used as the hole injection/transport material are shown below but are not limited thereto.

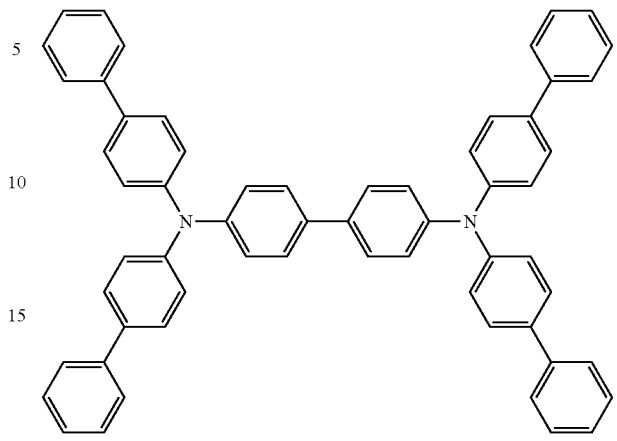

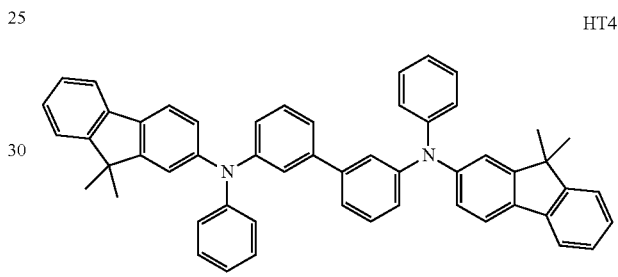

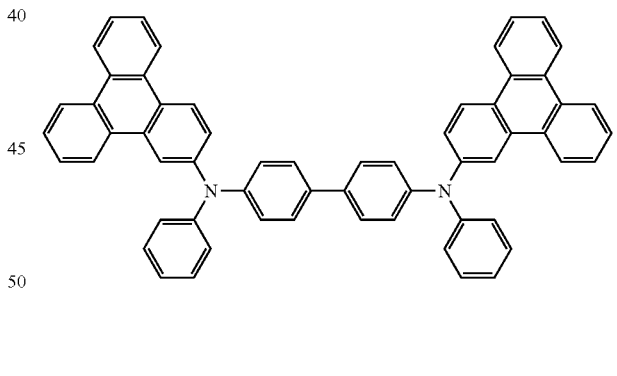

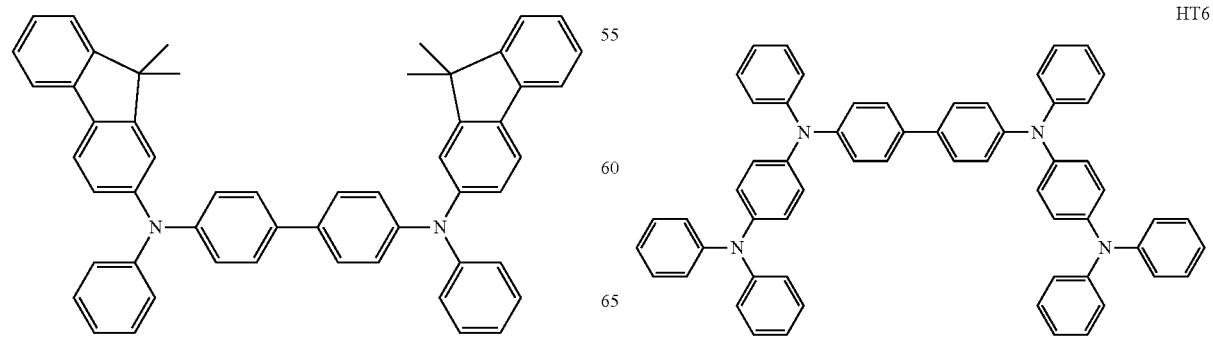

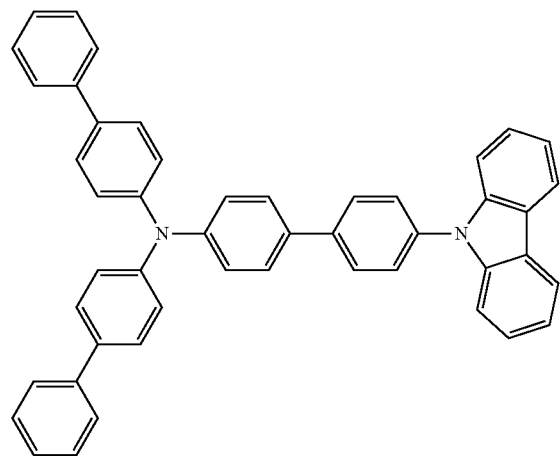
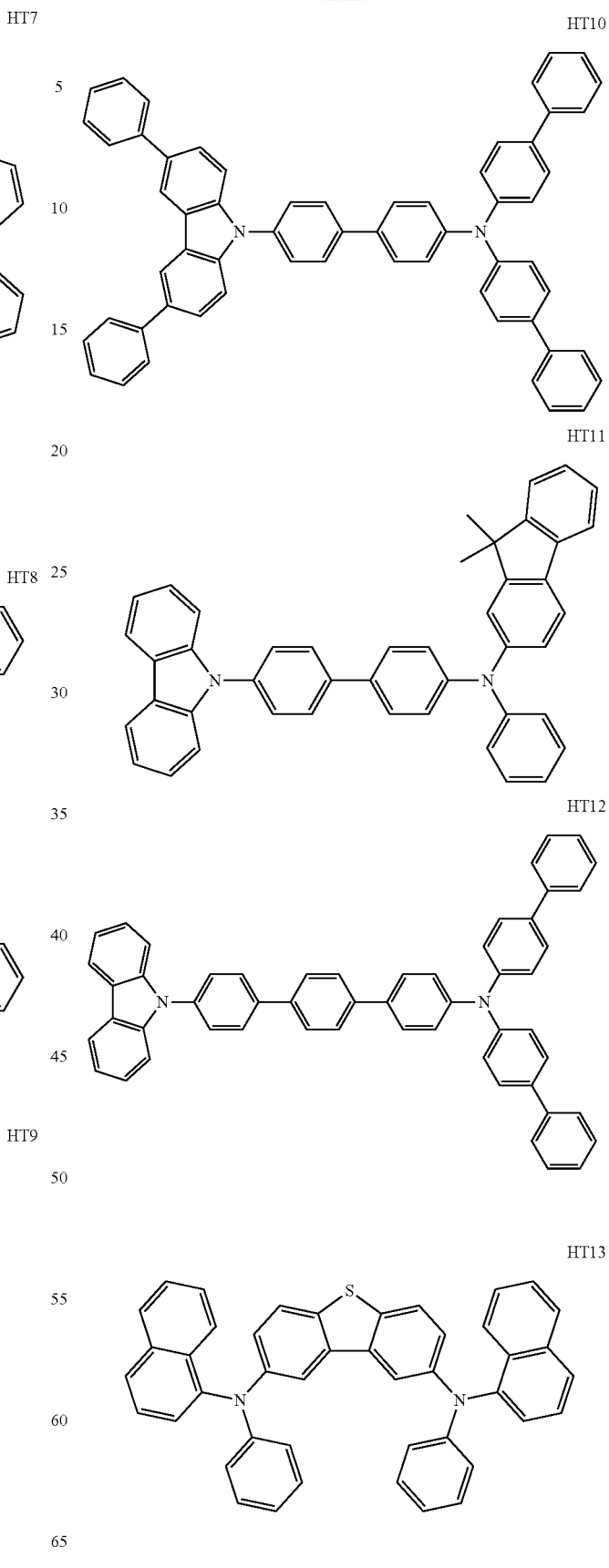

HT14

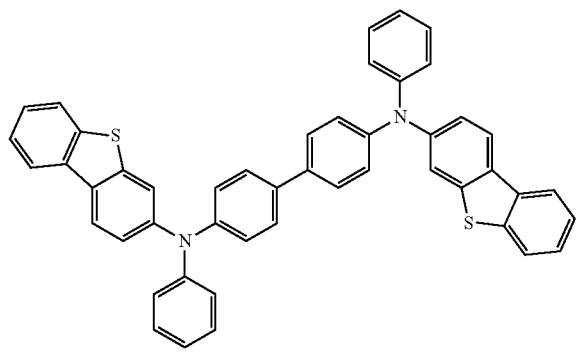

HT19

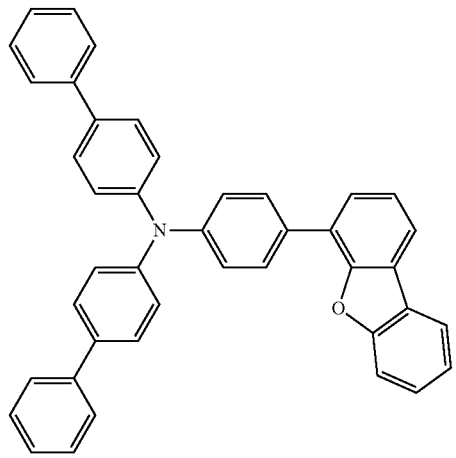

HT15

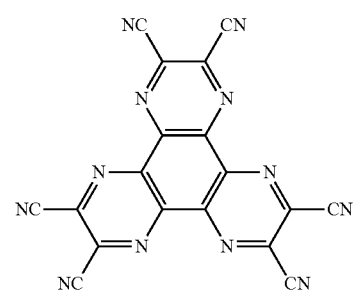

HT16

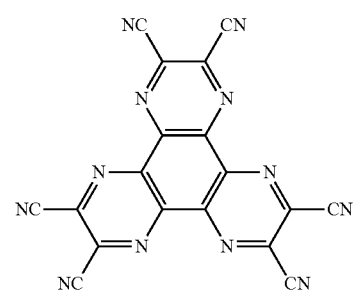

HT17

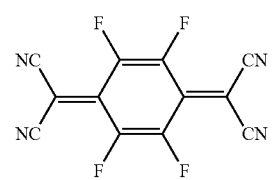

HT18

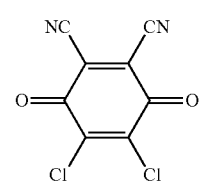

Examples of the light-emitting material that mainly relates to the function of light emission include, besides the organic compound represented by formula [1], fused ring compounds (such as fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives.

The organic compound according to the present disclosure is a compound having a narrow bandgap and low HOMO/LUMO energy. Accordingly, when the organic compound according to the present disclosure forms a mixture layer together with another light-emitting material or a plurality of light-emitting layers are stacked, similarly, the other light-emitting material also preferably has low HOMO/LUMO energy. This is because when the HOMO/LUMO energy is high, a quenching component or a trap level may be formed, for example, the other light-emitting material may form an exciplex together with the organic compound according to the present disclosure.

Specific examples of the compound used as the light-emitting material are shown below but are not limited thereto.

BD1

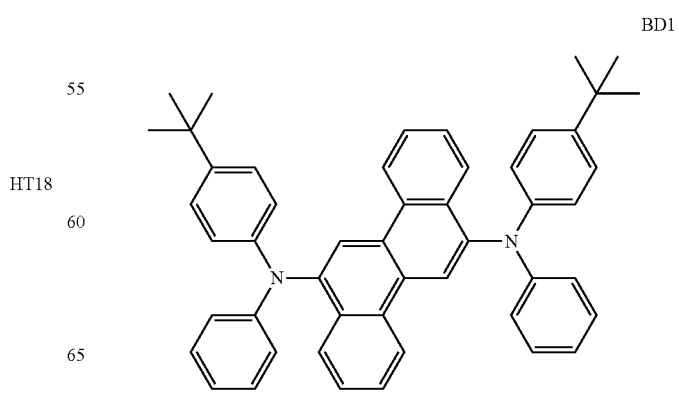

BD2 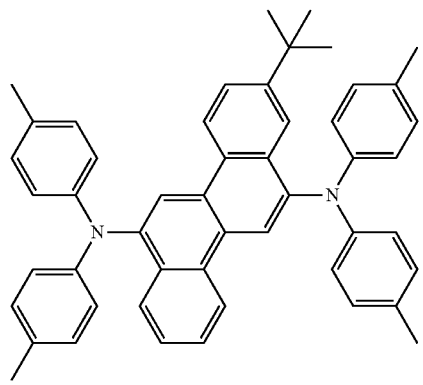
BD6 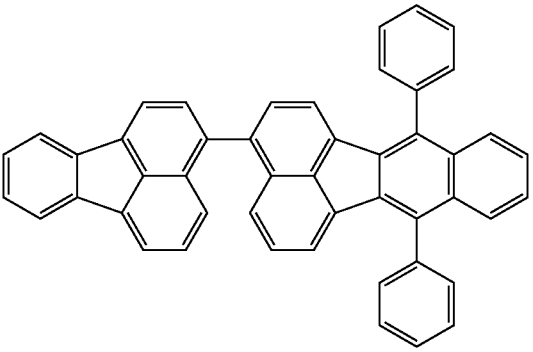
BD3 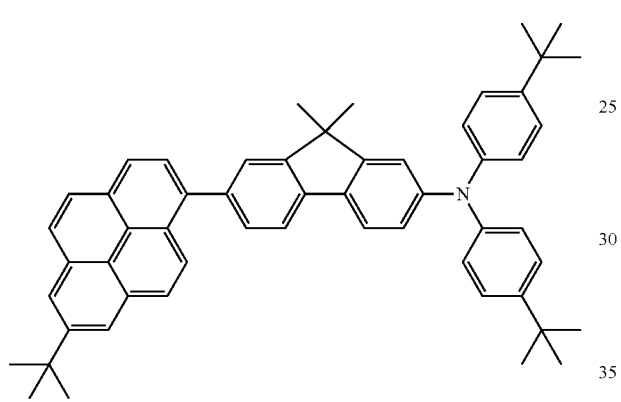
BD7 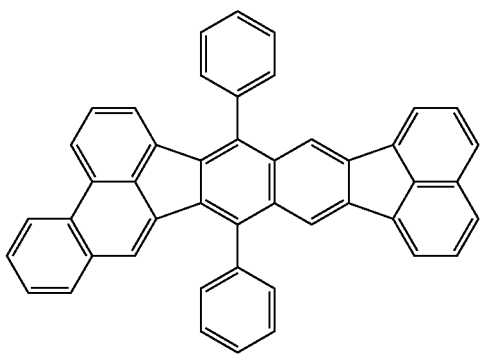
BD4 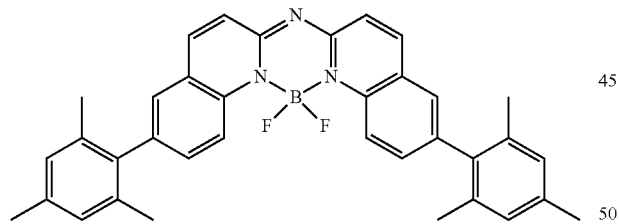
BD8 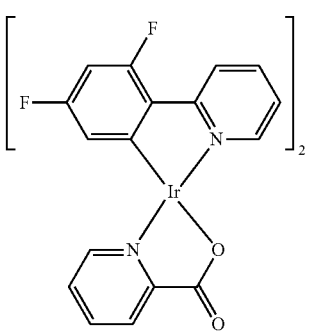
GD1 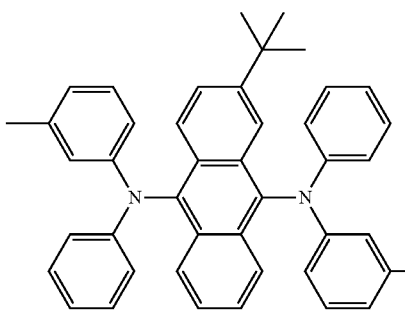
BD5 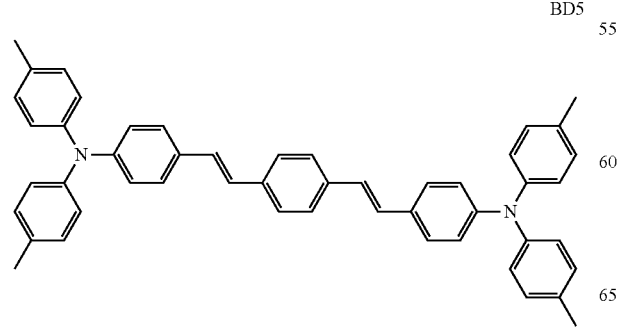
GD2 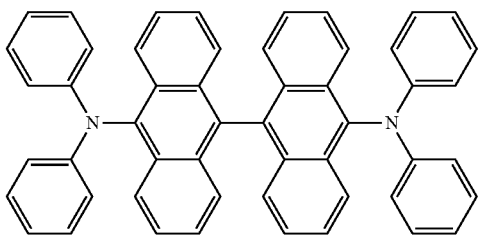

GD3
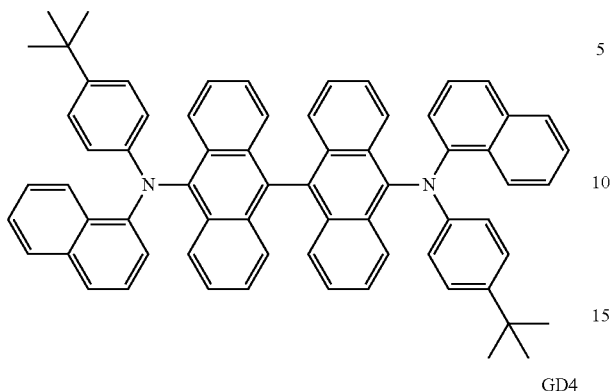
GD4
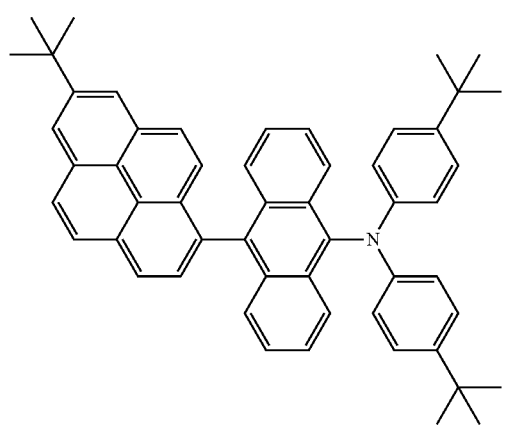
GD5
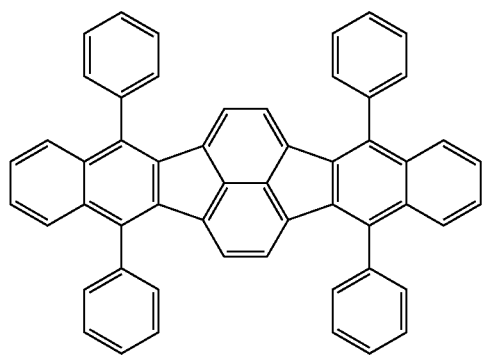
GD6
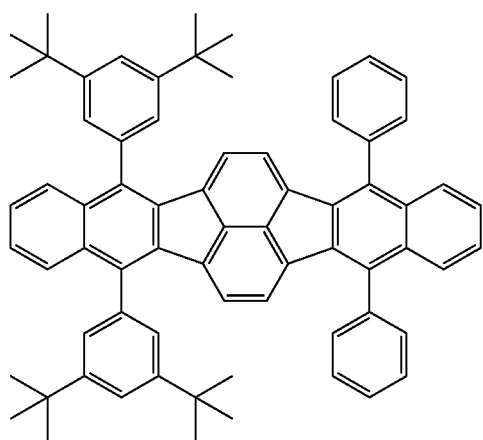
GD7
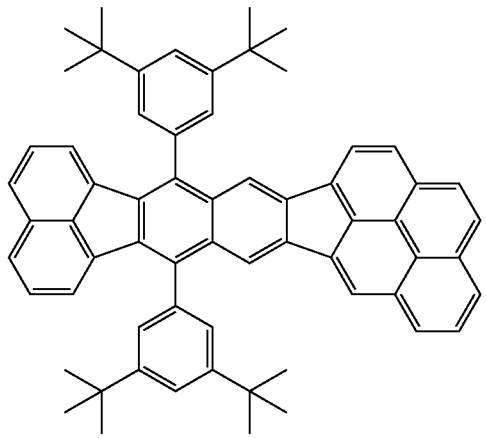
GD8
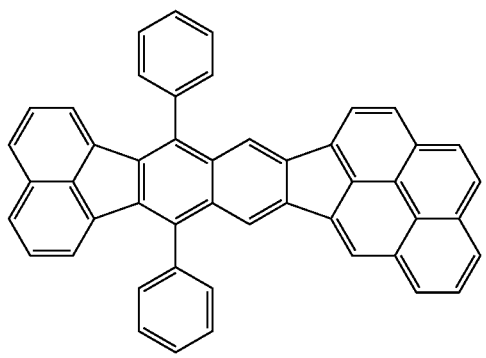
GD9
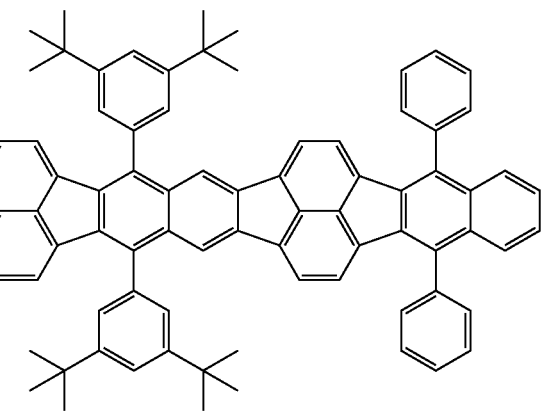
GD10
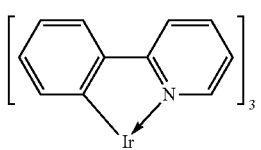

GD11

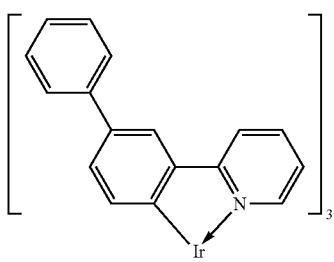

GD12

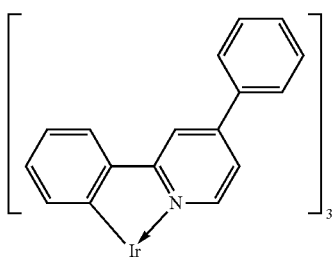

Examples of the light-emitting-layer host or the light-emission assist material that is contained in the light-emitting layer include, besides aromatic hydrocarbon compounds and derivatives thereof, carbazole derivatives, dibenzofuran derivatives, dibenzothiophene derivatives, organoaluminum complexes such as tris(8-quinolinolato) aluminum, and organoberyllium complexes.

The organic compound according to the present disclosure is a compound having a narrow bandgap and low HOMO/LUMO energy. Accordingly, preferably, the host material is also formed of a hydrocarbon and similarly has low HOMO/LUMO energy. This is because when the host material contains a heteroatom such as a nitrogen atom, the HOMO/LUMO energy is high, and a quenching component or a trap level may be formed, for example, the host material may form an exciplex together with the organic compound of the present disclosure.

The host material particularly preferably has an anthracene, tetracene, perylene, or pyrene skeleton in its molecular skeleton. This is because such a compound is constituted by a hydrocarbon as described above and has S1 energy capable of causing the organic compound of the present disclosure to sufficient energy transfer.

Specific examples of the compound used as the light-emitting-layer host or light-emission assist material that is contained in the light-emitting layer are shown below but are not limited thereto.

EM1

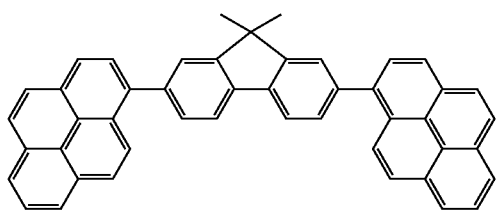

EM2

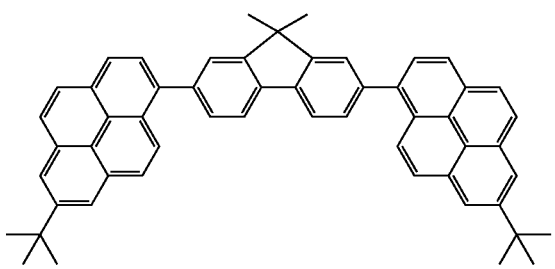

EM3

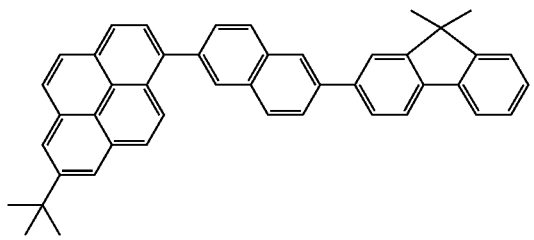

EM4

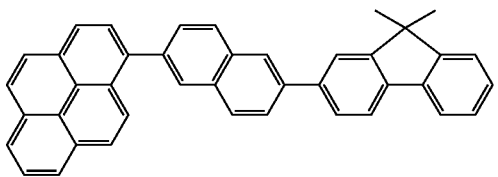

EM5

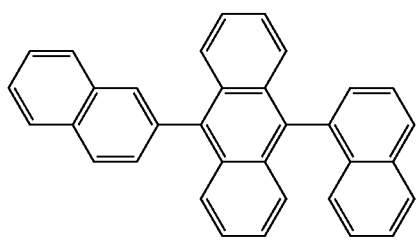

EM6

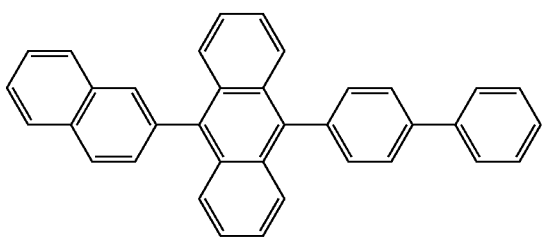

-continued
EM7
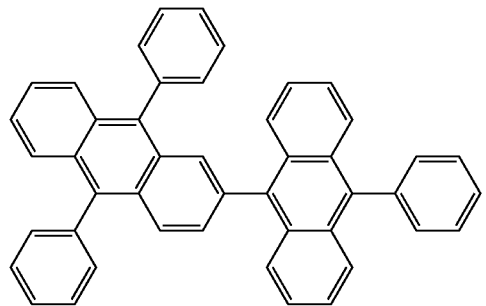
EM8
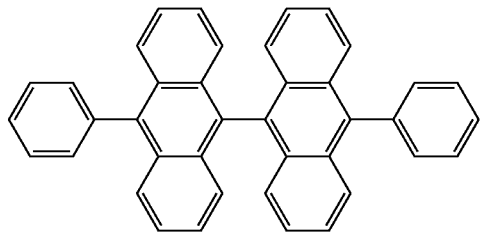
EM9
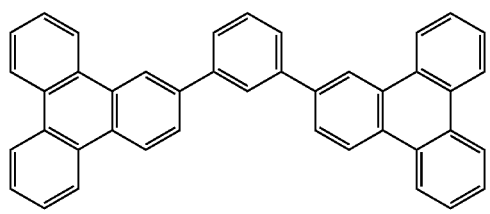
EM10
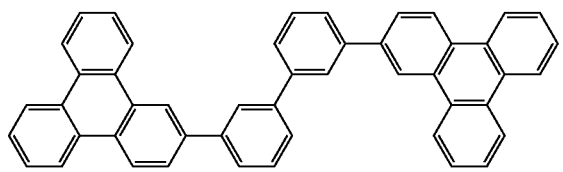
EM11
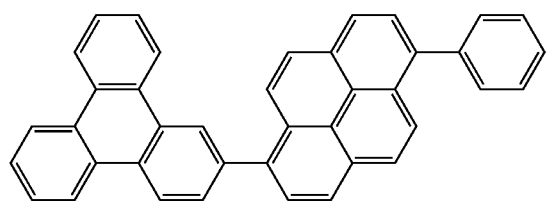
EM12
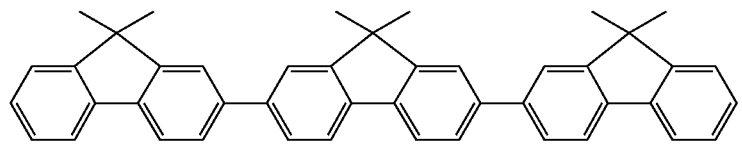
EM13
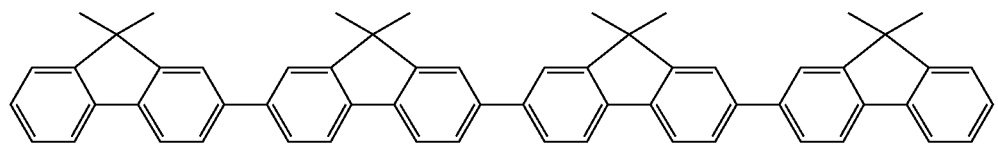
EM14
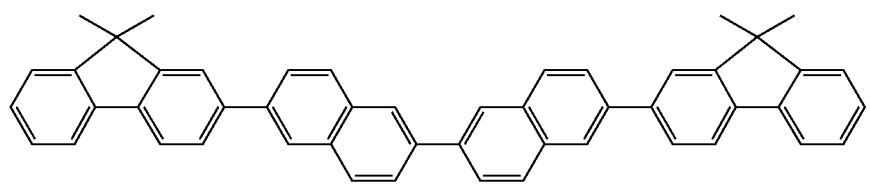
EM15
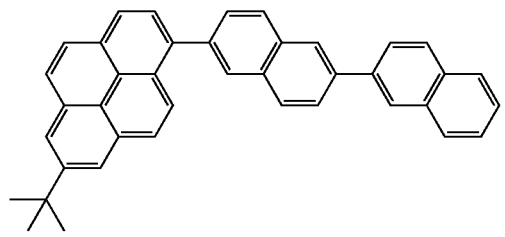
EM16
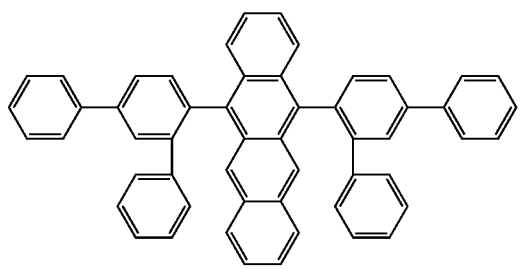

-continued
EM17
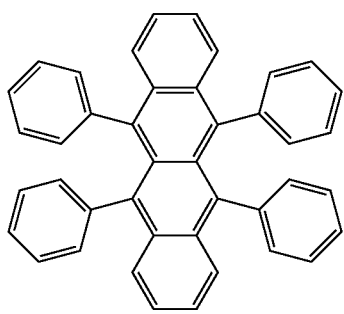
EM18
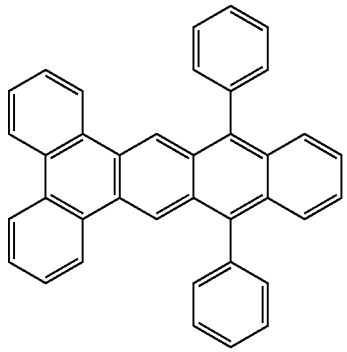
EM19
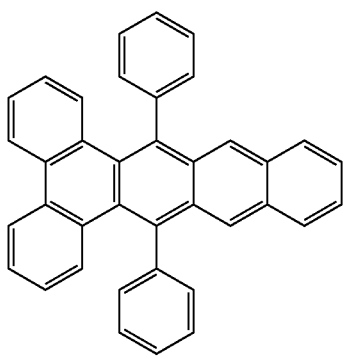
EM20
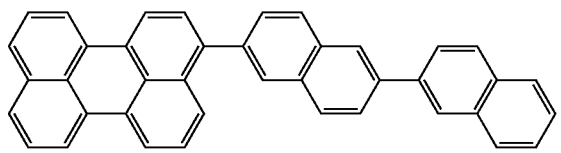
EM21
EM22
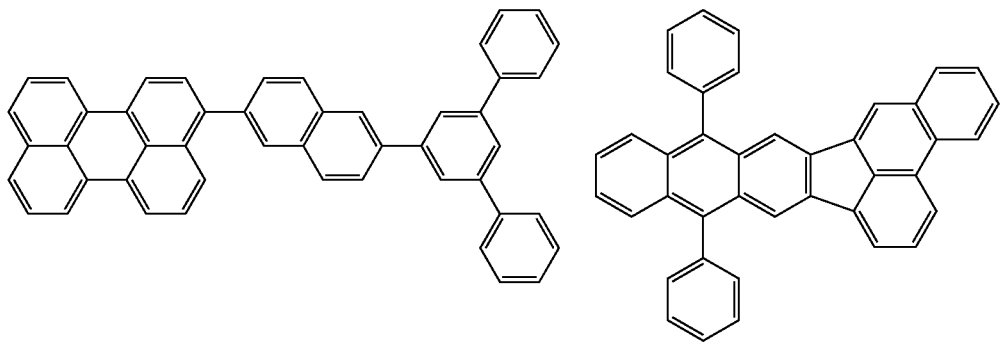
EM23
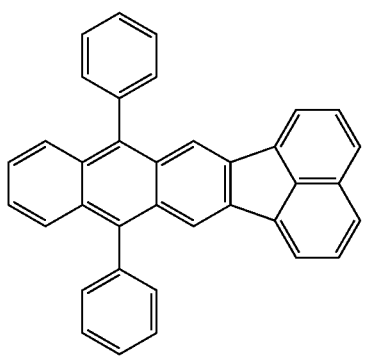
EM24
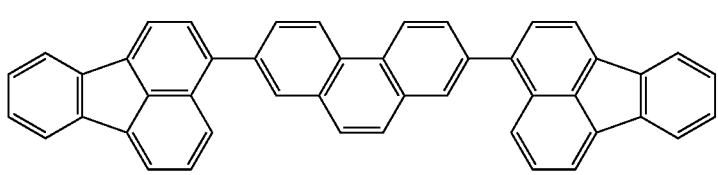

-continued

EM25
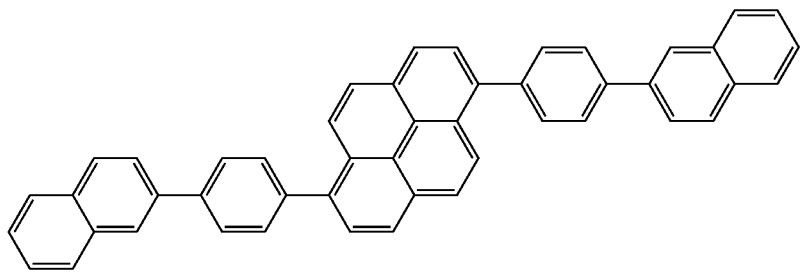

EM26
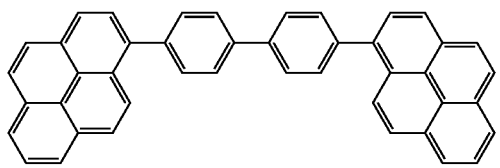

EM27
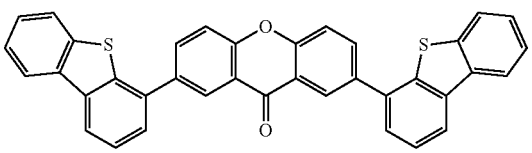

EM28
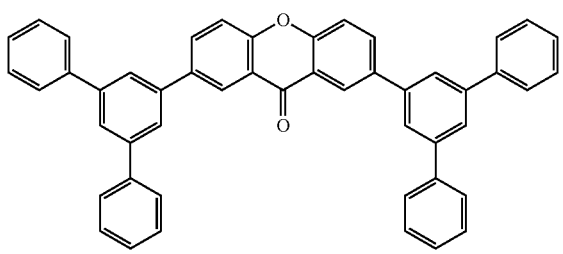

EM29
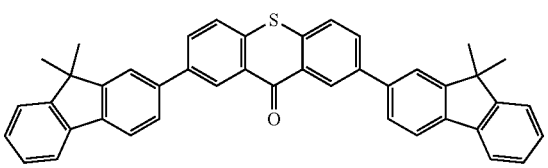

EM30
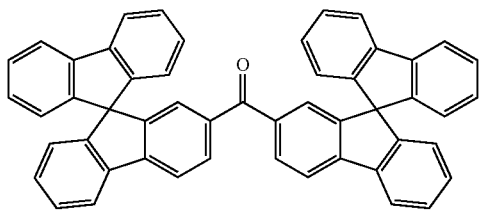

EM31
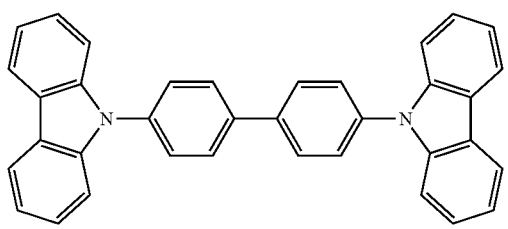

EM32
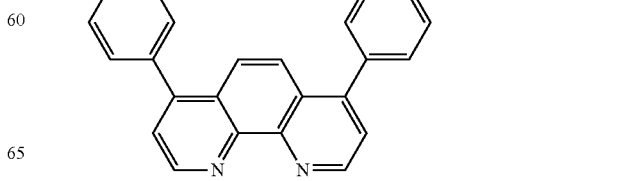

The electron transport material can be freely selected from materials capable of transporting electrons injected from the cathode to the light-emitting layer and is selected in consideration of, for example, the balance with the hole mobility of the hole transport material. Examples of the material having an electron transport performance include oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused ring compounds (such as fluorene derivatives, naphthalene derivatives, chrysene derivatives, and anthracene derivatives). The above electron transport material is also suitably used as a hole blocking layer. Specific examples of the compound used as the electron transport material are shown below but are not limited thereto.

ET1

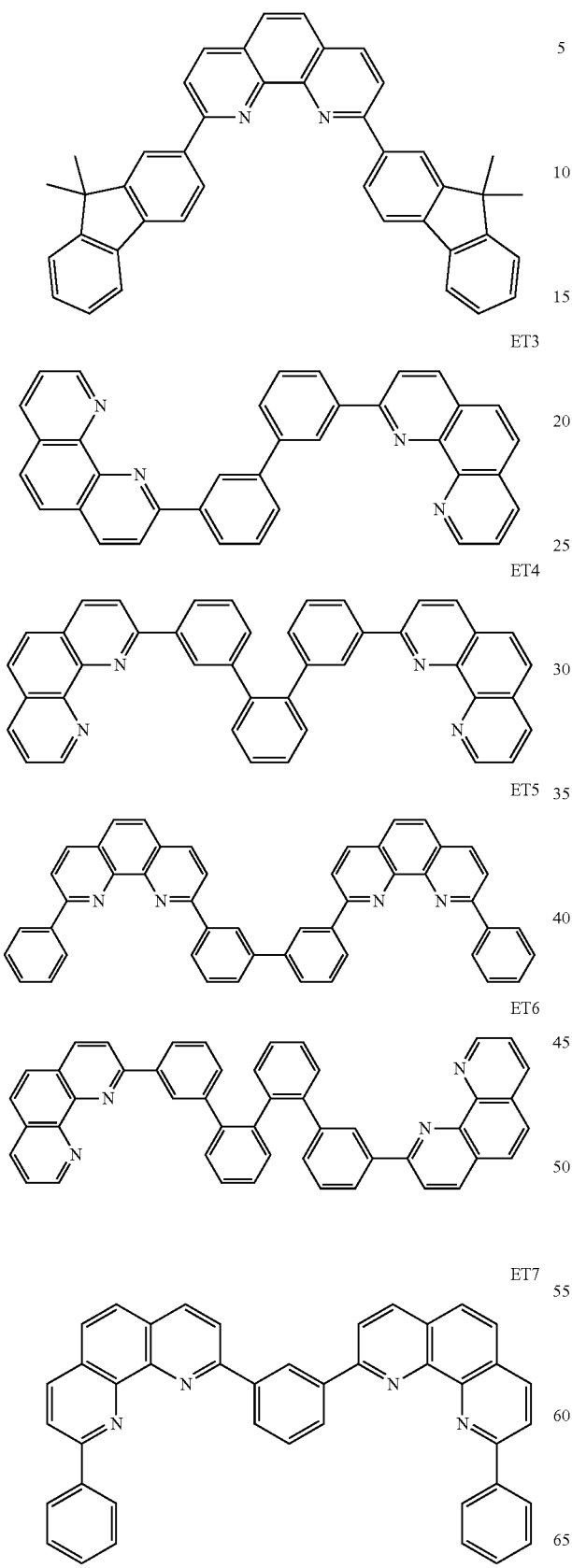
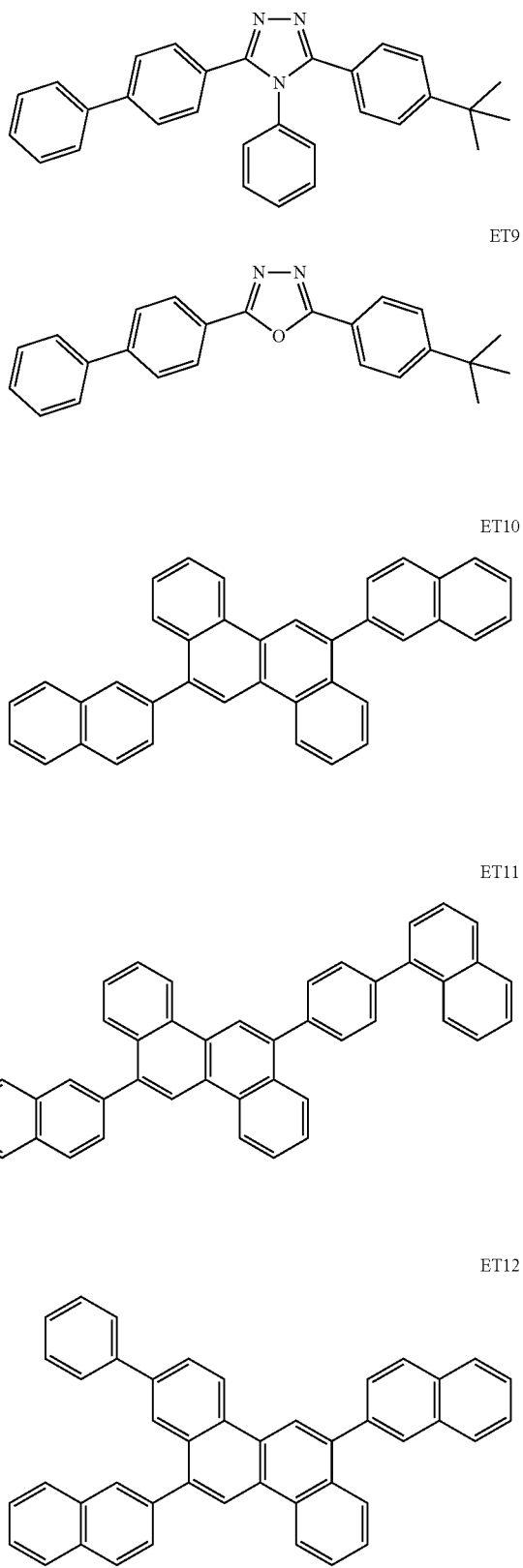

ET13
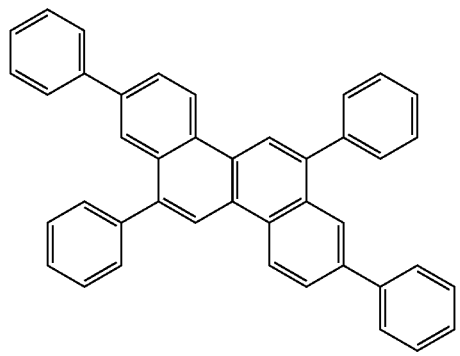
ET14
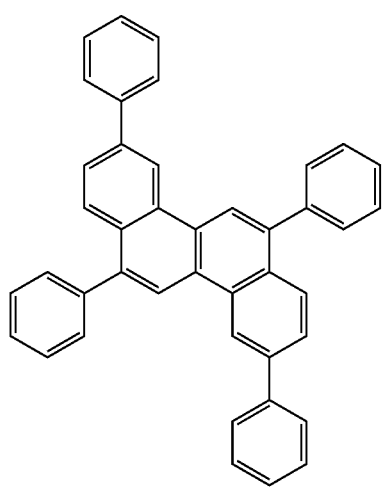
ET15
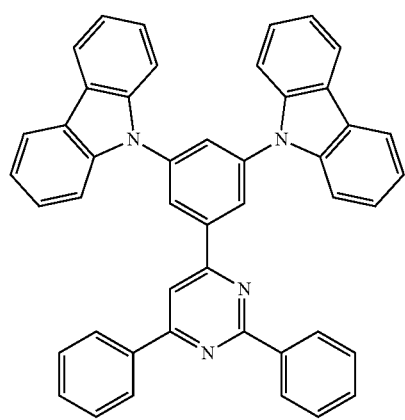
ET16
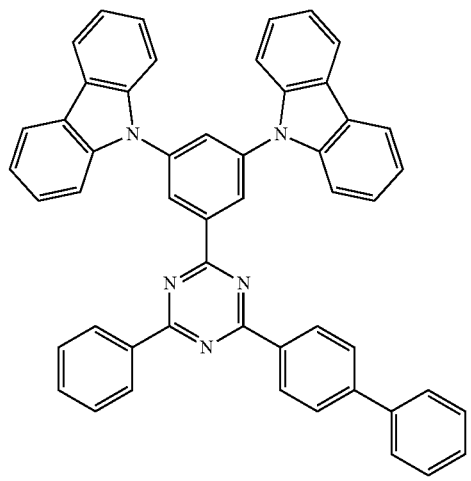
ET17
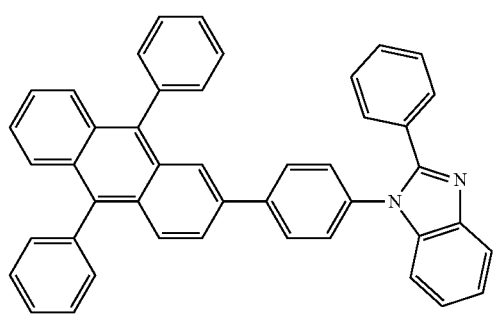
ET18
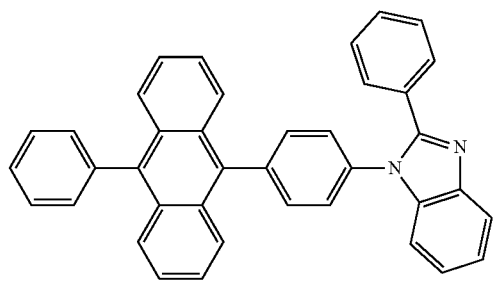
ET19
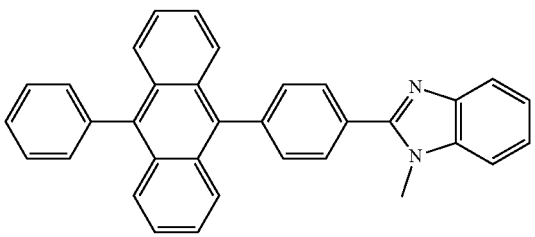

-continued

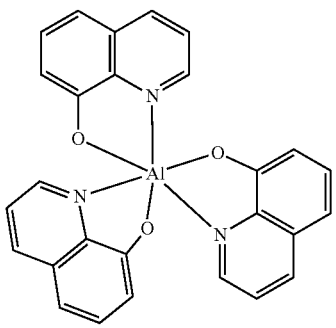
ET20

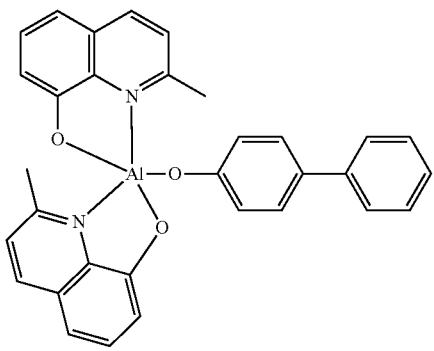
ET21

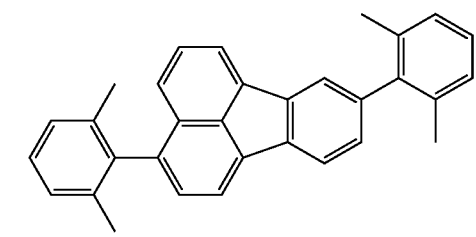
ET22

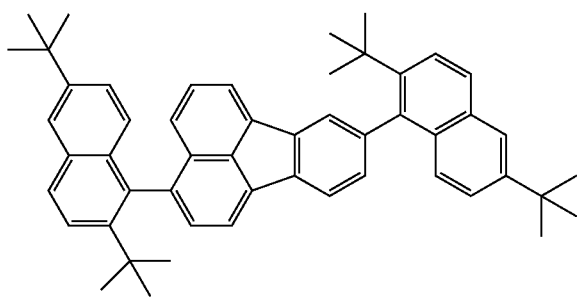
ET23

Components other than the organic compound layer, the components forming an organic light-emitting element of the present embodiment, will be described below.

The organic light-emitting element of the present embodiment may include a substrate. Any material such as quartz, glass, a silicon wafer, a resin, or a metal may be used as the substrate. Switching elements, such as transistors, and conductive lines are disposed on the substrate, and an insulating layer may be further disposed thereon. Any material may be used as the insulating layer as long as a contact hole can be formed in order to reliably establish electrical connection between an anode and a conductive line and insulation from an unconnected conductive line can be ensured. Examples of the material of the insulating layer include resins such as polyimide, silicon oxide, and silicon nitride.

The material of the anode preferably has a work function that is as high as possible. Examples of the material of the anode include elemental metals such as gold, platinum, silver, copper, nickel, palladium, cobalt, selenium, vanadium, and tungsten; mixtures containing these metals; alloys of these metals; and metal oxides such as tin oxide, zinc oxide, indium oxide, indium tin oxide (ITO), and indium zinc oxide. Examples thereof further include conductive polymers such as polyaniline, polypyrrole, and polythiophene. These electrode materials may be used alone or in combination of two or more thereof. The anode may be formed of a single layer or a plurality of layers. When the anode is used as a reflective electrode, for example, chromium, aluminum, silver, titanium, tungsten, molybdenum, an alloy thereof, or a laminate thereof can be used. When the anode is used as a transparent electrode, a transparent conductive oxide layer made of, for example, indium tin oxide (ITO) or indium zinc oxide can be used, but the transparent electrode is not limited thereto. Photolithography can be used for forming the anode.

In contrast, the material of the cathode preferably has a low work function. Examples of the material of the cathode include alkali metals such as lithium; alkaline earth metals such as calcium; elemental metals such as aluminum, titanium, manganese, silver, lead, and chromium; and mixtures containing these metals. Alloys of these elemental metals can also be used. For example, magnesium-silver, aluminum-lithium, aluminum-magnesium, silver-copper, and zinc-silver can be used. Metal oxides such as indium tin oxide (ITO) can also be used. These electrode materials may be used alone or in combination of two or more thereof. The cathode may be formed of a single layer or multiple layers.

The form of the cathode is not particularly limited. The cathode may be a conductive oxide layer made of ITO or the like to provide a top-emission element. Alternatively, the cathode may be a reflective electrode made of aluminum (Al) or the like to provide a bottom-emission element. The method for forming the cathode is not particularly limited. For example, DC and AC sputtering methods may be used because good film coverage is achieved to easily reduce the resistance.

After the formation of the cathode, a sealing member may be formed. For example, a glass plate provided with a moisture absorbent may be bonded to the cathode. Thus, permeation of water or the like in an organic compound layer can be suppressed to suppress the occurrence of display defects. In another embodiment, a passivation film made of silicon nitride or the like may be formed on the cathode to suppress permeation of water or the like in an organic compound layer. For example, after the formation of the cathode, the resulting substrate may be transferred to another chamber without breaking the vacuum, and a silicon nitride film having a thickness of 2 µm may be formed by a CVD method to provide a sealing film.

A color filter may be disposed on each pixel. For example, color filters each having a size corresponding to the pixel size may be formed on another substrate, and this substrate may be bonded to the substrate having organic light-emitting elements thereon. Alternatively, a color filter may be formed by patterning on a sealing film made of silicon oxide or the like using photolithography.

The organic compound layers (such as a hole injection layer, a hole transport layer, an electron blocking layer, a light-emitting layer, a hole blocking layer, an electron transport layer, and an electron injection layer) that form an organic light-emitting element according to the present embodiment are formed by the following method. Specifically, a dry process such as a vacuum vapor deposition method, an ionized vapor deposition method, sputtering, or plasma can be employed to form the organic compound layers. Alternatively, instead of the dry process, it is also possible to employ a wet process in which an organic compound is dissolved in a suitable solvent, and a layer is formed by a known coating method (such as spin coating, dipping, a casting method, a Langmuir-Blodgett (LB) method, or an ink jet method). When a layer is formed by, for example, a vacuum vapor deposition method or a solution coating method, crystallization is unlikely to occur, and the resulting layer has good stability with time. When a layer is formed by a coating method, the layer may be formed by using a suitable binder resin in combination. Examples of the binder resin include, but are not limited to, polyvinylcarbazole resins, polycarbonate resins, polyester resins, ABS resins, acrylic resins, polyimide resins, phenolic resins, epoxy resins, silicone resins, and urea resins. These binder resins may be used alone as a homopolymer or a copolymer or in combination as a mixture of two or more thereof. Furthermore, known additives such as a plasticizer, an oxidation inhibitor, and an ultraviolet absorbent may be optionally used in combination.

Devices Using Organic Light-Emitting Element

The organic light-emitting element according to the present embodiment can be used as a member of a display device or an illumination device. In addition, the organic light-emitting element may be used as, for example, an exposure light source of an electrophotographic image forming apparatus, a backlight of a liquid crystal display device, or a light-emitting device including a white light source having a color filter. An example of the color filler is a filter through which any of three colors of red, green, and blue transmits.

A display device according to the present embodiment includes a plurality of pixels. At least one of the pixels includes an organic light-emitting element of the present embodiment. The at least one of the pixels includes an organic light-emitting element according to the present embodiment and an active element. Examples of the active element include switching elements and amplifying elements. A specific example of the active element is a transistor. An anode or a cathode of the organic light-emitting element is electrically connected to a drain electrode or a source electrode of the transistor. The transistor may include an oxide semiconductor in an active region thereof. The oxide semiconductor may be amorphous or crystalline, or may contain both an amorphous phase and a crystalline phase. In a case of a crystalline oxide semiconductor, the crystal may be any of a single crystal, a microcrystal, and a crystal in which a specific axis, such as the c-axis, is oriented. Alternatively, at least two of these may coexist.

An organic light-emitting device that includes such a switching element may be used as an image display device in which organic light-emitting elements are provided as pixels or may be used as an illumination device. Alternatively, the organic light-emitting device may be used as an exposure light source for exposing a photoreceptor of an electrophotographic image forming apparatus such as a laser beam printer or a copier.

Herein, the display device can be used as an image display device such as a personal computer (PC). An example of the transistor is a TFT element. The TFT element is disposed, for example, on an insulating surface of s substrate. The display device may be an image information processing device that includes an image input unit configured to input image information from an area CCD, a linear CCD, a memory card, or the like and an information processing unit in which the input information is processed, and that displays an input image on a display unit. The display unit included in an imaging device or an ink jet printer may have a touch panel function. The touch panel function may be operated by using infrared, an electrostatic capacitance, a resistive film, or electromagnetic induction, and the operation method is not particularly limited. The display device may be used as a display unit of a multifunctional printer.

The illumination device is, for example, a device that illuminates a room. The illumination device may emit white light (color temperature: 4,200 K), natural white light (color temperature: 5,000 K), or any other light such as blue light to red light. Among organic light-emitting elements included in the illumination device, any of the organic light-emitting elements may be an organic light-emitting element according to the present disclosure. The illumination device according to the present embodiment includes an organic light-emitting element according to the present embodiment and an AC/DC converter connected to the organic light-emitting element. The AC/DC converter is a circuit configured to convert an alternating voltage to a direct voltage. This converter is a circuit configured to supply a driving voltage to the organic light-emitting element. The illumination device may further include a color filter. The illumination device according to the present embodiment may include a heat dissipation unit. The heat dissipation unit dissipates heat in the device to the outside of the device and may be made of, for example, a metal having a high specific heat or liquid silicon.

The emission luminance of the organic light-emitting element according to the present embodiment is controlled by a TFT, which is an example of a switching element. Accordingly, when a plurality of such organic light-emitting elements are arranged in a plane, an image can be displayed by controlling the emission luminance of each of the organic light-emitting elements. The switching element according to the present embodiment is not limited to a TFT. The switching element may be a transistor, an MIM element, or an active matrix driver formed on a substrate such as a Si substrate. The active matrix driver may be formed in the substrate. Whether on a substrate or in a substrate is selected depending on the level of resolution. For example, in the case of a size of 1 inch and a resolution of about QVGA, organic light-emitting elements may be disposed on a Si substrate. By driving the display device including the organic light-emitting elements according to the present embodiment, an image having good image quality can be stably displayed for a long time.

Display Device

FIG. 1 is a schematic sectional view illustrating an example of a display device according to the present embodiment and is a view illustrating an example of a display device that includes organic light-emitting elements and TFT elements connected to the organic light-emitting elements. The TFT elements are each an example of an active element. The display device according to the present embodiment may include red, green, and blue color filters. The red, green, and blue color filters may be arranged in a delta array.

A display device 10 in FIG. 1 includes a substrate 11 made of, for example, glass and a moisture-proof film 12 that is disposed on the substrate 11 and that protects a TFT element 18 or an organic compound layer 22. TFT elements 18 each include a metal gate electrode 13, a gate insulating film 14, a semiconductor layer 15, a drain electrode 16, and a source electrode 17. An insulating film 19 is disposed over the TFT elements 18. An anode 21 that forms an organic light-emitting element and the source electrode 17 are connected to each other through a contact hole 20. The form of electrical connection between electrodes (anode 21 and cathode 23) included in the organic light-emitting element and electrodes (source electrode 17 and drain electrode 16) included in a TFT is not limited to the form illustrated in FIG. 1. Specifically, either the anode 21 or the cathode 23 is electrically connected to either the source electrode 17 or the drain electrode 16 of the TFT element. In the display device 10 in FIG. 1, the organic compound layer 22 is illustrated as if the organic compound layer 22 is formed of a single layer. Alternatively, the organic compound layer 22 may be formed of a plurality of layers. A first protective layer 24 and a second protective layer 25 that suppress deterioration of the organic light-emitting element are disposed over the cathode 23.

In the display device 10 in FIG. 1, transistors are used as switching elements. Alternatively, MIM elements may be used as the switching elements instead of the transistors. The transistors used in the display device 10 in FIG. 1 are not limited to transistors using a single-crystal silicon wafer. Alternatively, the transistors may be thin-film transistors having an active layer on an insulating surface of a substrate. Examples of the active layer include single-crystal silicon, amorphous silicon, non-single-crystal silicon such as microcrystalline silicon, and non-single-crystal oxide semiconductors such as indium zinc oxide and indium gallium zinc oxide. Thin-film transistors are also referred to as TFT elements. The transistors included in the display device 10 in FIG. 1 may be formed in a substrate such as a Si substrate. The expression "formed in a substrate" as used herein means that transistors are produced by processing a substrate, such as a Si substrate, itself. That is, having transistors in a substrate can also be considered that a substrate and transistors are integrally formed. Whether or not transistors are disposed in a substrate is selected depending on the level of resolution. For example, in the case of a size of 1 inch and a resolution of about QVGA, the transistor may be disposed in a Si substrate.

Figure 2:
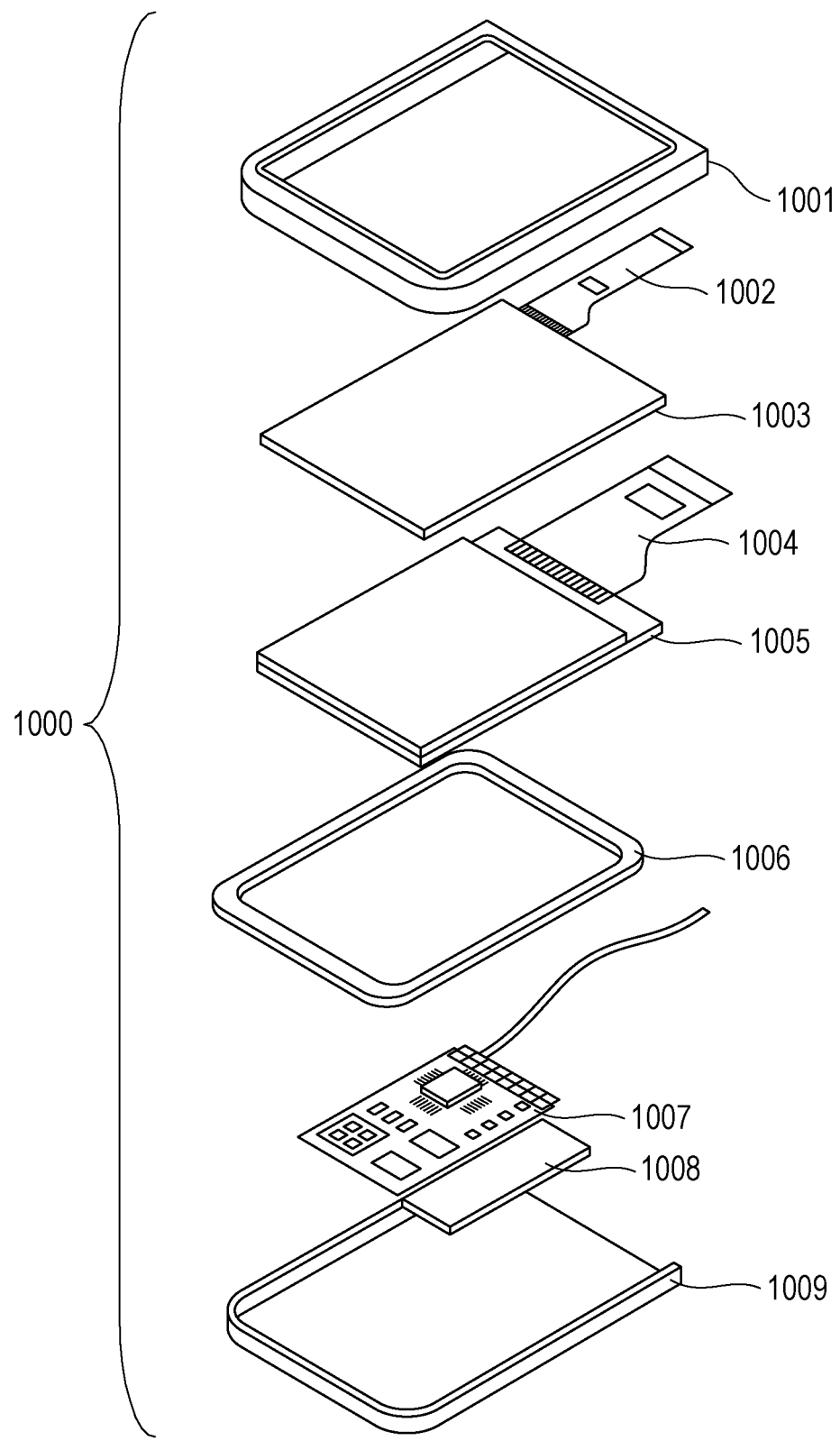
FIG. 2 is a schematic view illustrating an example of a display device according to the present embodiment.

FIG. 2 is a schematic view illustrating an example of a display device according to the present embodiment. A display device 1000 may include an upper cover 1001 and a lower cover 1009, and a touch panel 1003, a display panel 1005, a frame 1006, a printed circuit board 1007, and a battery 1008 that are disposed between the upper cover 1001 and the lower cover 1009. The touch panel 1003 and the display panel 1005 are connected to flexible printed circuits (FPC) 1002 and 1004, respectively. An organic light-emitting element according to the present embodiment may be used in the display panel 1005. Transistors are printed on the printed circuit board 1007. The battery 1008 is not necessarily provided unless the display device is a mobile device. Even when the display device is a mobile device, the battery 1008 is not necessarily disposed at the position illustrated in the figure.

Figure 3A:
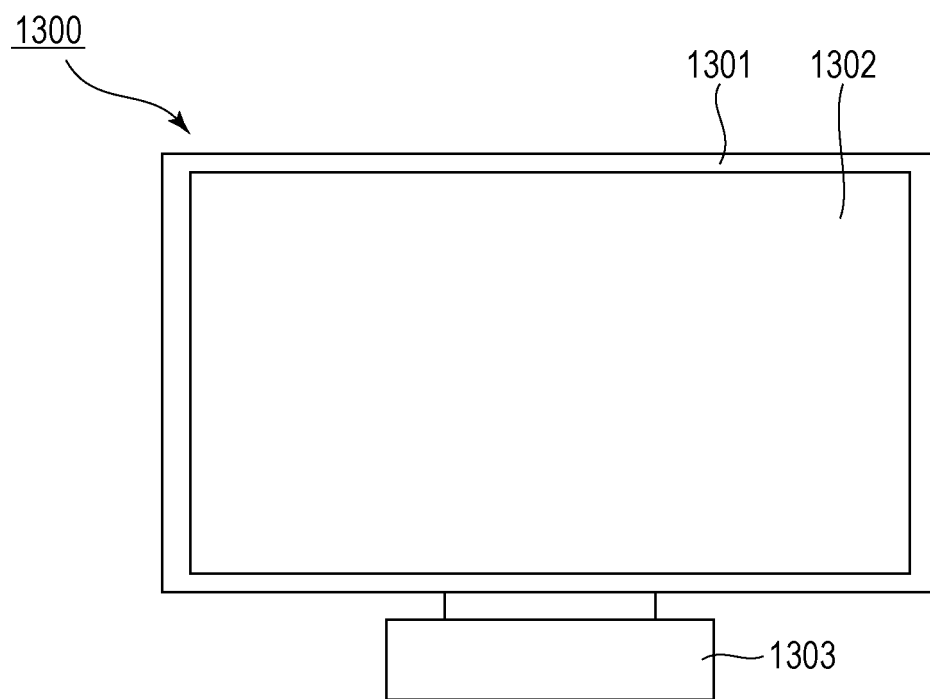
FIG. 3A is a schematic view illustrating an example of a display device according to the present embodiment.
Figure 3B:
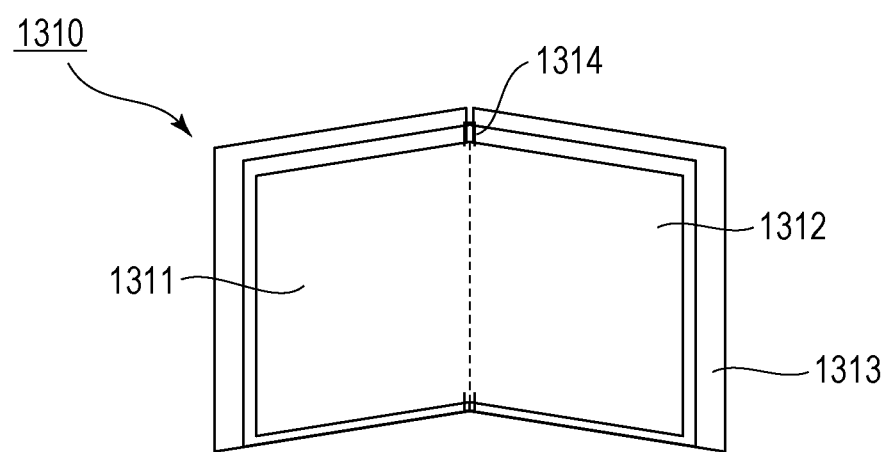
FIG. 3B is a schematic view illustrating an example of a display device according to the present embodiment.

FIGS. 3A and 3B are schematic views each illustrating an example of a display device according to the present embodiment. FIG. 3A illustrates a display device such as a television monitor or a PC monitor. A display device 1300 includes a frame 1301 and a display unit 1302. An organic light-emitting element according to the present embodiment may be used in the display unit 1302. The display device 1300 further includes a base 1303 that supports the frame 1301 and the display unit 1302. The base 1303 is not limited to the form illustrated in FIG. 3A. Alternatively, the lower side of the frame 1301 may also function as the base. The frame 1301 and the display unit 1302 may be curved. The radius of curvature of the frame 1301 and the display unit 1302 may be 5,000 mm or more and 6,000 mm or less. A display device 1310 illustrated in FIG. 3B is configured to be foldable and is a so-called foldable display device. The display device 1310 has a first display unit 1311, a second display unit 1312, a housing 1313, and a folding point 1314. Each of the first display unit 1311 and the second display unit 1312 may include an organic light-emitting element accordion to the present embodiment. The first display unit 1311 and the second display unit 1312 may be a single display device without a joint. The first display unit 1311 and the second display unit 1312 can be separated from each other in the folding point 1314. The first display unit 1311 and the second display unit 1312 may display images that are different from each other. Alternatively, one image may be displayed on a set of the first display unit 1311 and the second display unit 1312.

Imaging Device

A display device according to the present embodiment may be used as a display unit of an imaging device including an optical unit having a plurality of lenses and an imaging element that receives light that has passed through the optical unit. The imaging device may include a display unit configured to display information acquired by the imaging element. The display unit may be a display unit exposed to the outside of the imaging device or a display unit disposed in a viewfinder. The imaging device may be a digital camera or a digital camcorder.

Figure 4:
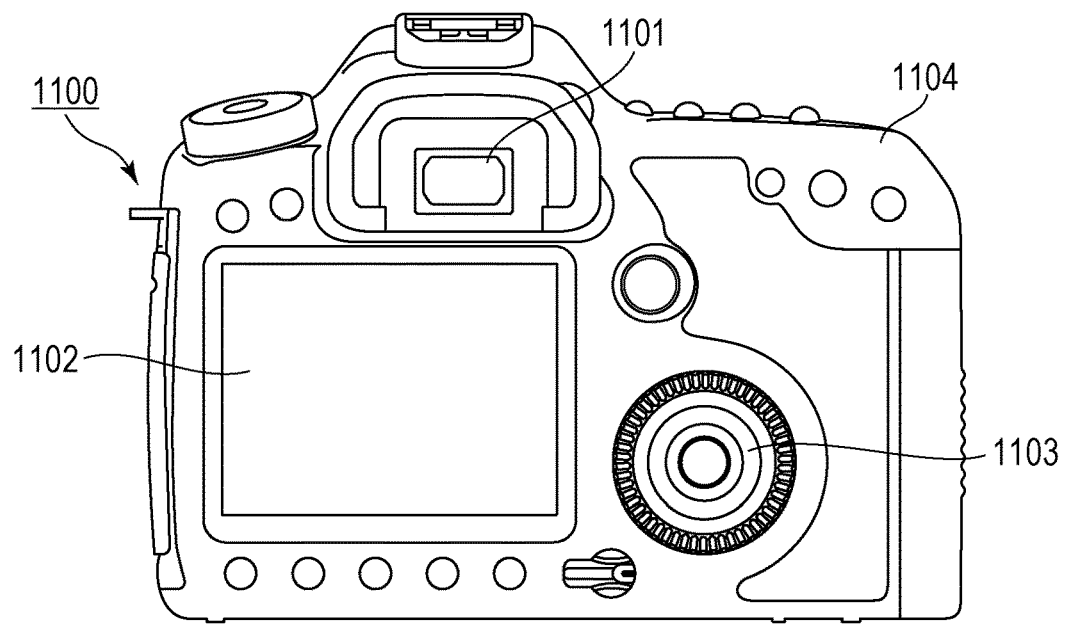
FIG. 4 is a schematic view illustrating an example of an imaging device according to the present embodiment.

FIG. 4 is a schematic view illustrating an example of an imaging device according to the present embodiment. An imaging device 1100 may include a viewfinder 1101, a rear display 1102, an operation unit 1103, and a housing 1104. The viewfinder 1101 may include a display device according to the present embodiment. In such a case, the display device may display not only an image to be captured but also, for example, environmental information and imaging instructions. The environmental information may include, for example, the intensity of external light, the direction of external light, the moving speed of a subject to be captured, and the possibility that the subject is hidden by an object. Since the suitable timing for capturing an image is a very short period of time, it is desirable to display information as quickly as possible. Accordingly, the display device that includes an organic light-emitting element according to the present disclosure is preferably used. This is because the organic light-emitting element has a high response speed. The display device that includes an organic light-emitting element is more suitable than liquid crystal display devices for use in devices for which a high display speed is required. The imaging device 1100 includes an optical unit (not illustrated). The optical unit has a plurality of lenses and forms an image on an imaging element disposed in the housing 1104. The focus can be adjusted by adjusting the relative positions of the plurality of lenses. This operation may be automatically performed.

Electronic Device

A display device according to the present embodiment may be used in a display unit of an electronic device such as a mobile terminal. In such a case, the display unit may have both a display function and an operational function. Examples of the mobile terminal include mobile phones, such as smartphones, tablet computers, and head-mounted displays.

Figure 5:
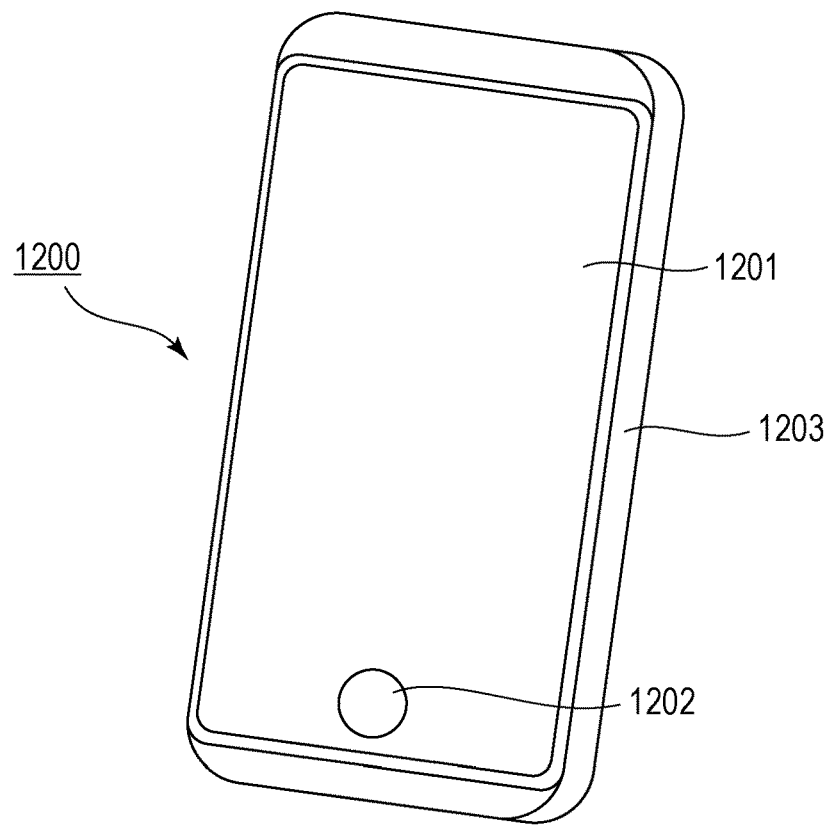
FIG. 5 is a schematic view illustrating an example of a mobile device according to the present embodiment.

FIG. 5 is a schematic view illustrating an example of a mobile device according to the present embodiment. A mobile device 1200 includes a display unit 1201, an operation unit 1202, and a housing 1203. The housing 1203 may include therein circuits, a printed board having the circuits, a battery, and a communication unit. The operation unit 1202 may be a button or a touch-panel response unit. The operation unit 1202 may be a biometric authentication unit configured to, for example, recognize the fingerprint and release the lock. A mobile device including a communication unit may be referred to as a communication device.

Illumination Device

Figure 6:
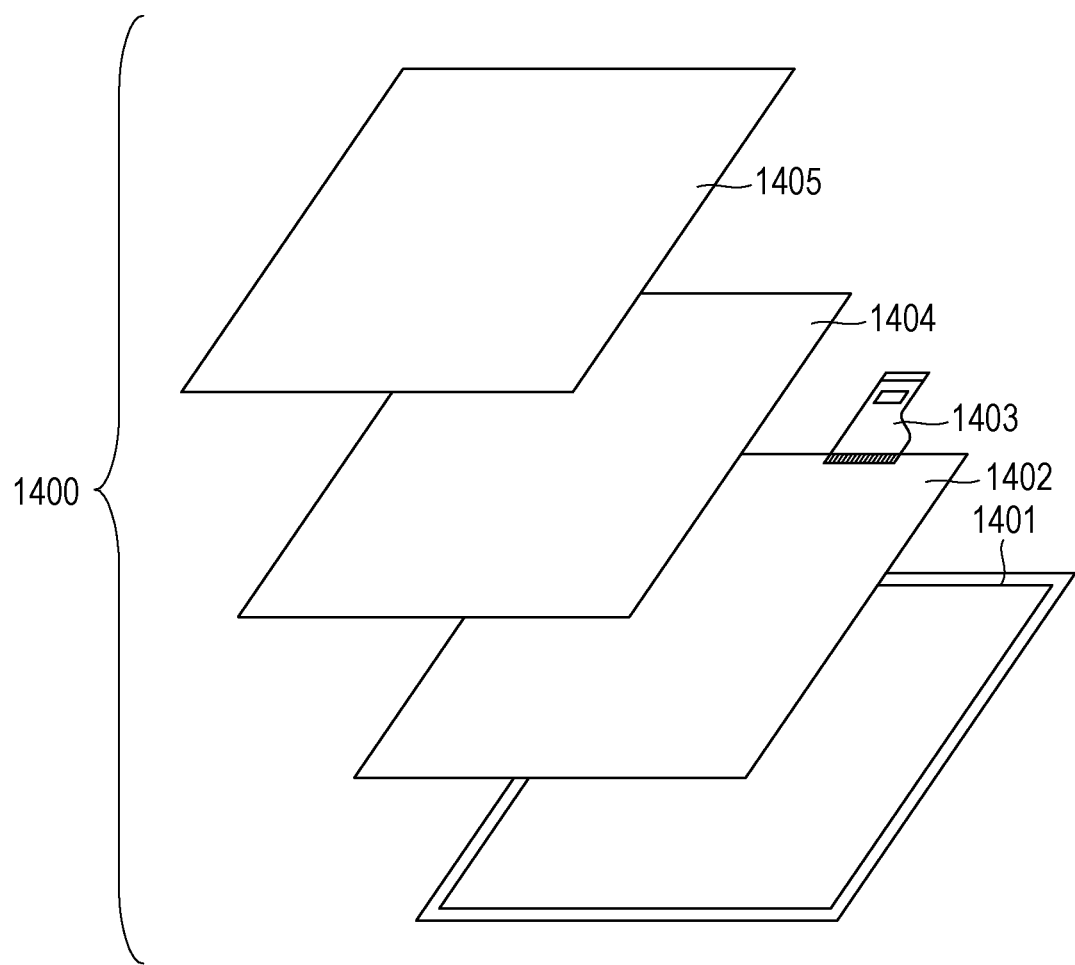
FIG. 6 is a schematic view illustrating an example of an illumination device according to the present embodiment.

FIG. 6 is a schematic view illustrating an example of an illumination device according to the present embodiment. An illumination device 1400 may include a housing 1401, a light source 1402, a circuit board 1403, an optical filter 1404, and a light diffusion unit 1405. The light source 1402 may include an organic light-emitting element according to the present embodiment. The optical filter 1404 may be a filter that improves the color rendering properties of the light source 1402. The light diffusion unit 1405 effectively diffuses light emitted from the light source 1402 and allows the light to reach a wide region, for example, for lighting up. A cover may be optionally disposed on an outermost portion.

The illumination device is, for example, a device that illuminates a room. The illumination device may emit white light, natural white light, or any other light such as blue light to red light. The illumination device may include a light modulation circuit configured to modulate the light. The illumination device may include an organic light-emitting element according to the present disclosure and a power supply circuit connected to the organic light-emitting element. The power supply circuit is a circuit configured to convert an alternating voltage to a direct voltage. The white light has a color temperature of 4,200 K, and the natural white light has a color temperature of 5,000 K. The illumination device may include a color filter.

The illumination device according to the present embodiment may include a heat dissipation unit. The heat dissipation unit dissipates heat in the device to the outside of the device and may be made of, for example, a metal having a high specific heat or liquid silicon.

Moving Object

A moving object according to the present embodiment includes a body and a lighting fixture disposed on the body. FIG. 7 is a schematic view illustrating an example of the moving object according to the present embodiment and is a view illustrating an automobile including a tail lamp which is an example of a lighting fixture for a vehicle. An automobile 1500 functioning as the body includes a tail lamp 1501, and the tail lamp 1501 may light up when, for example, the brakes are applied. The tail lamp 1501 may include an organic light-emitting element according to the present embodiment. The tail lamp 1501 may include a protective member that protects the organic light-emitting element. The protective member may be made of any material as long as the strength of the protective member is high to a certain extent, and the protective member is transparent. The protective member may be made of polycarbonate or the like. The polycarbonate may be mixed with a furandicarboxylic acid derivative, an acrylonitrile derivative, or the like. The automobile 1500 may include a car body 1503 and a window 1502 attached to the car body 1503. The window 1502 may be a transparent display unless it is a window for checking of the front and rear of the automobile 1500. The transparent display may include an organic light-emitting element according to the present embodiment. In such a case, the members such as electrodes of the organic light-emitting element are made of transparent materials.

EXAMPLES

The present disclosure will now be described by way of Examples. However, the present disclosure is not limited to these Examples.

Example 1

Synthesis of Exemplary Compound A3

(1) Synthesis of Compound E7

Compound E7 was synthesized in accordance with the synthesis method described in Japanese Patent Laid-Open No. 2011-011994. Specifically, the synthesis was conducted in accordance with the following scheme.

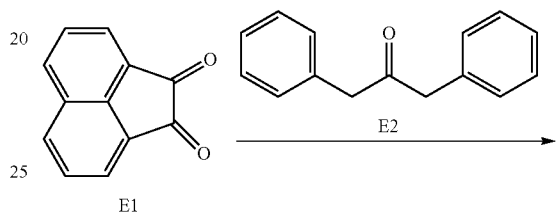

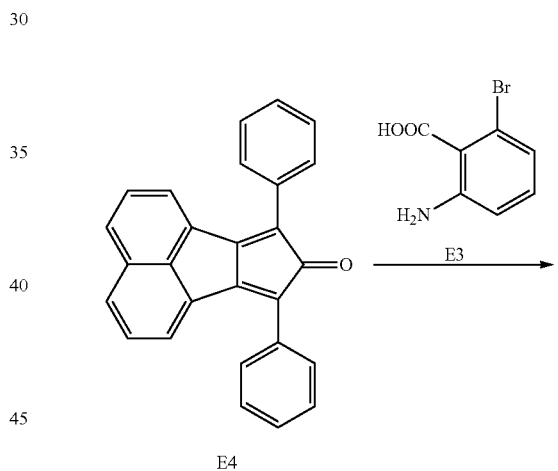

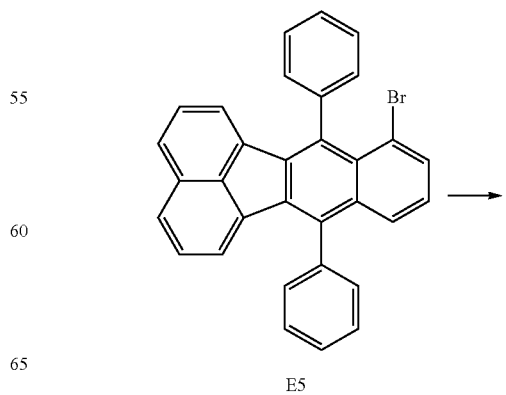

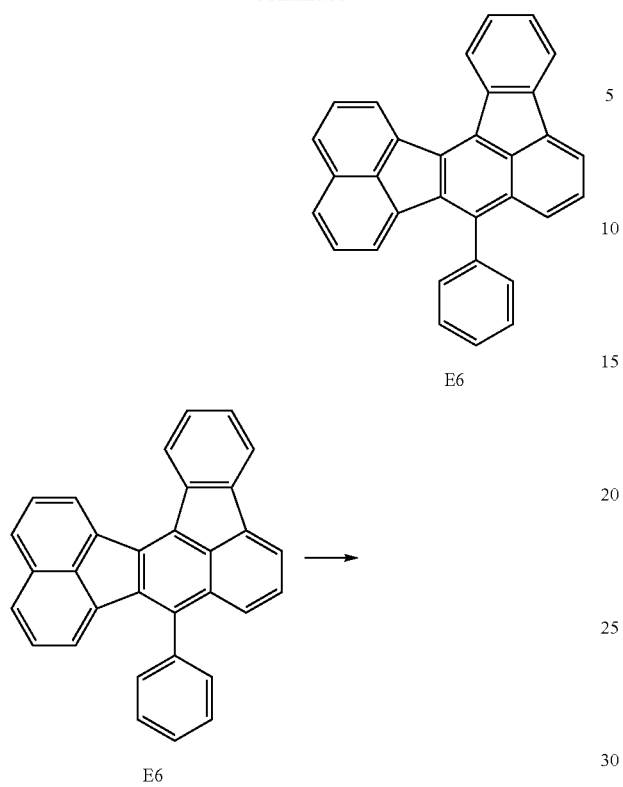

E6

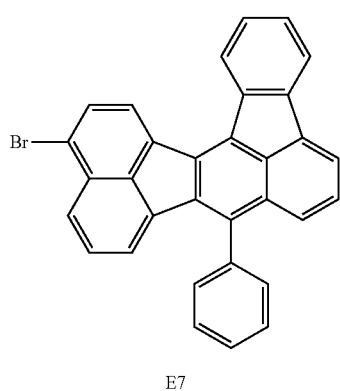

E7

(2) Synthesis of Compound E8

Compound E8 was synthesized by the following scheme.

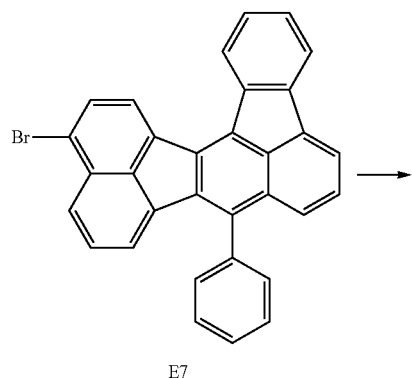

E7

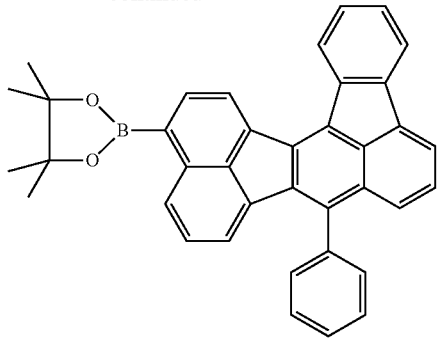

E8

The following reagents were placed in a 100-mL recovery flask.

Compound E7: 2.4 g (5.0 mmol)

Bis(pinacolato)diboron: 1.3 g (5.0 mmol)

[1,1'-Bis(diphenylphosphino)ferrocene]palladium(II) dichloride dichloromethane adduct: 0.33 g (0.41 mmol)

Potassium acetate: 1.3 g (13.0 mmol)

1,4-Dioxane: 50 mL

The resulting reaction solution was heated and refluxed in nitrogen for five hours under stirring. After the completion of the reaction, the solvent was distilled off under reduced pressure. The resulting solid was purified with a silica gel column (chloroform:heptane=2:1). As a result, 1.8 g of compound E8 was obtained (yield: 70%).

(3) Synthesis of Exemplary Compound A3

Exemplary Compound A3 was synthesized by the following scheme.

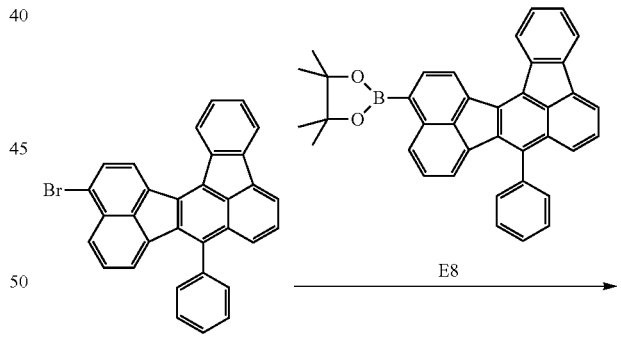

E7

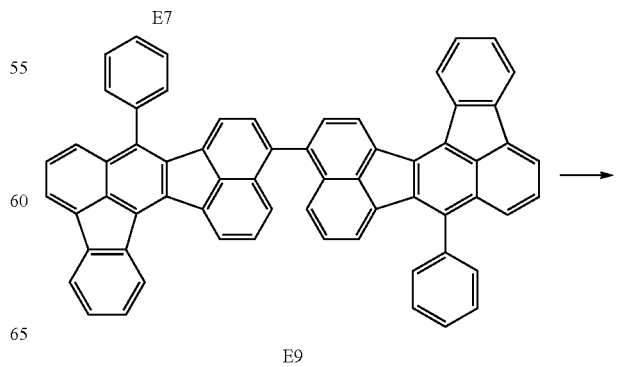

E9

-continued

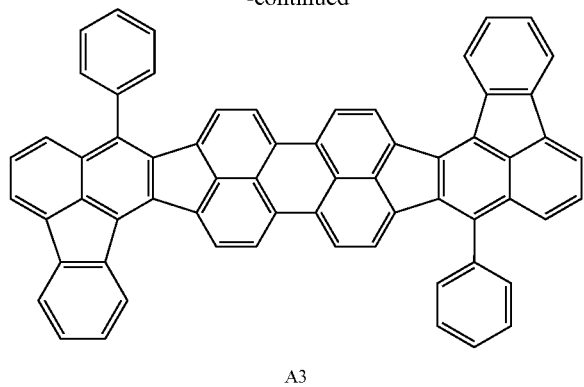

A3

The following reagents and solvents were placed in a 100-mL recovery flask.
Compound E7: 1.6 g (3 mmol)
Compound E8: 1.6 g (3 mmol)
Pd(PPh$_3$)$_4$: 0.6 g
Toluene: 100 mL
Ethanol: 10 mL
2M-Aqueous sodium carbonate solution: 30 mL Next, the resulting reaction solution was heated to 80° C. in a nitrogen stream and stirred at this temperature (80° C.) for eight hours. After the completion of the reaction, ethanol was added to the resulting reaction solution to precipitate a crystal. The crystal was then separated by filtration and sequentially dispersed and washed in water, ethanol, and heptane. Next, the resulting crystal was dissolved in chlorobenzene under heating, subsequently subjected to hot filtration, and then recrystallized. As a result, 1.7 g of compound E9, which was a red compound, was obtained (yield: 65%).

The following reagents and solvent were placed in a 500-mL reaction container.

Compound E9: 1.7 g (2 mmol)
Trifluoroacetic acid: 20 mL
Methylene chloride: 150 mL Next, the following reagent was placed in the reaction container in a water bath.
BF$_3$.OEt: 4 mL Next, after the reaction solution was stirred for about 10 minutes, 1.0 g of 2,3-dichloro-5,6-dicyano-p-benzoquinone (DDQ) was placed in the reaction container. Subsequently, after the reaction solution was stirred for 10 minutes, 1.0 g of ferrocene was placed in the reaction container in the water bath at 20° C. After stirring was conducted for about five minutes, 150 mL of methanol was added. A red precipitate generated at this time was filtered to obtain a red solid. Next, the solid was dissolved in chlorobenzene and recrystallized with heptane. As a result, 1.0 g of exemplary compound A3 was obtained in the form of a blackish red crystal (yield: 60%).

Exemplary compound A3 was subjected to mass spectrometry by using a matrix assisted laser desorption/ionization time-of-flight mass spectrometer (MALDI-TOF-MS) (Autoflex LRF manufactured by Bruker Corporation).
MALDI-TOF-MS
Actual measured value: m/z=800
Calculated value: C$_{64}$H$_{32}$=800

Examples 2 to 9

Synthesis of Exemplary Compounds

Exemplary compounds shown in Table 3 were synthesized as in Example 1 except that the raw materials E2, E3, E7, and E8 in Example 1 were changed to a raw material 1, a raw material 2, a raw material 3, and a raw material 4, respectively. Table 3 further shows the actual measured value m/z of the results of mass spectrometry performed as in Example 1.

TABLE 3

| Example | Exemplary compound/m/z | Raw material 1 | Raw material 2 |
|---|---|---|---|
| Example 2 | A10/953 | | E3 |

TABLE 3-continued
| Example 3 | 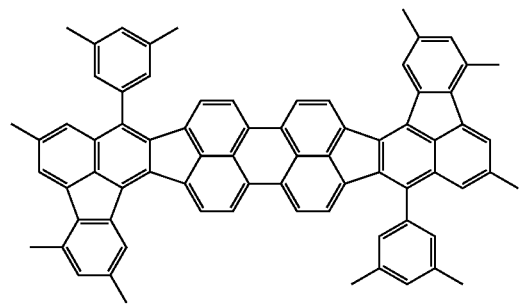 B2/941 | 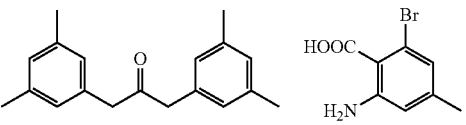 |
| Example 4 | 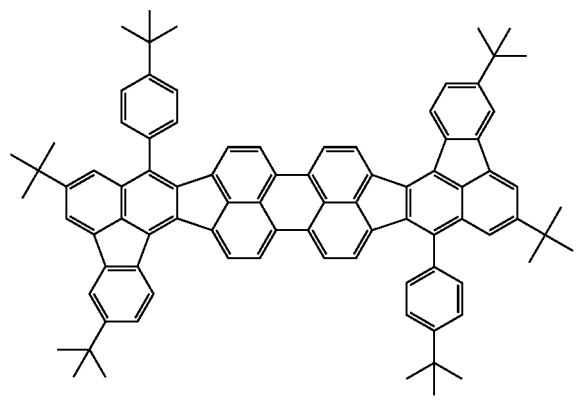 B4/1053 | 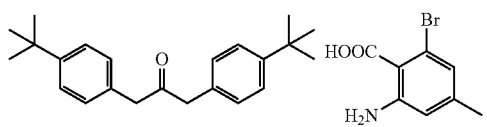 |
| Example 5 | 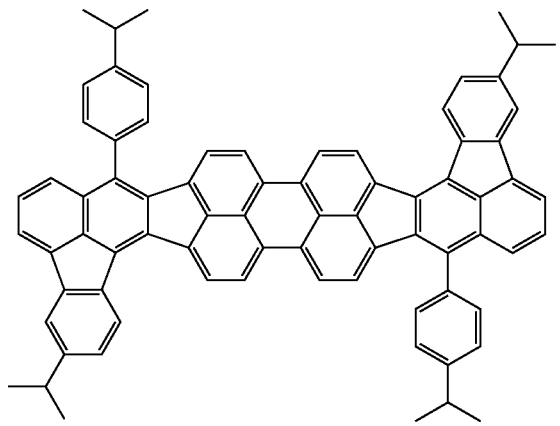 B7/969 |  | E3 |
| Example 6 | 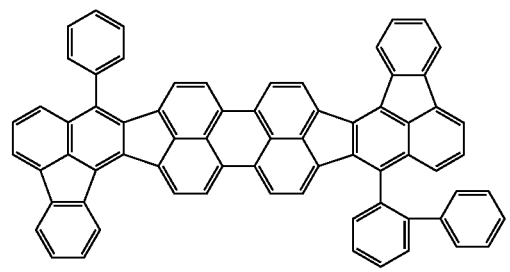 A9/877 | 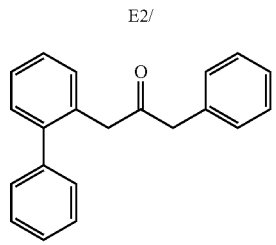 E2/ | E3 |

TABLE 3-continued
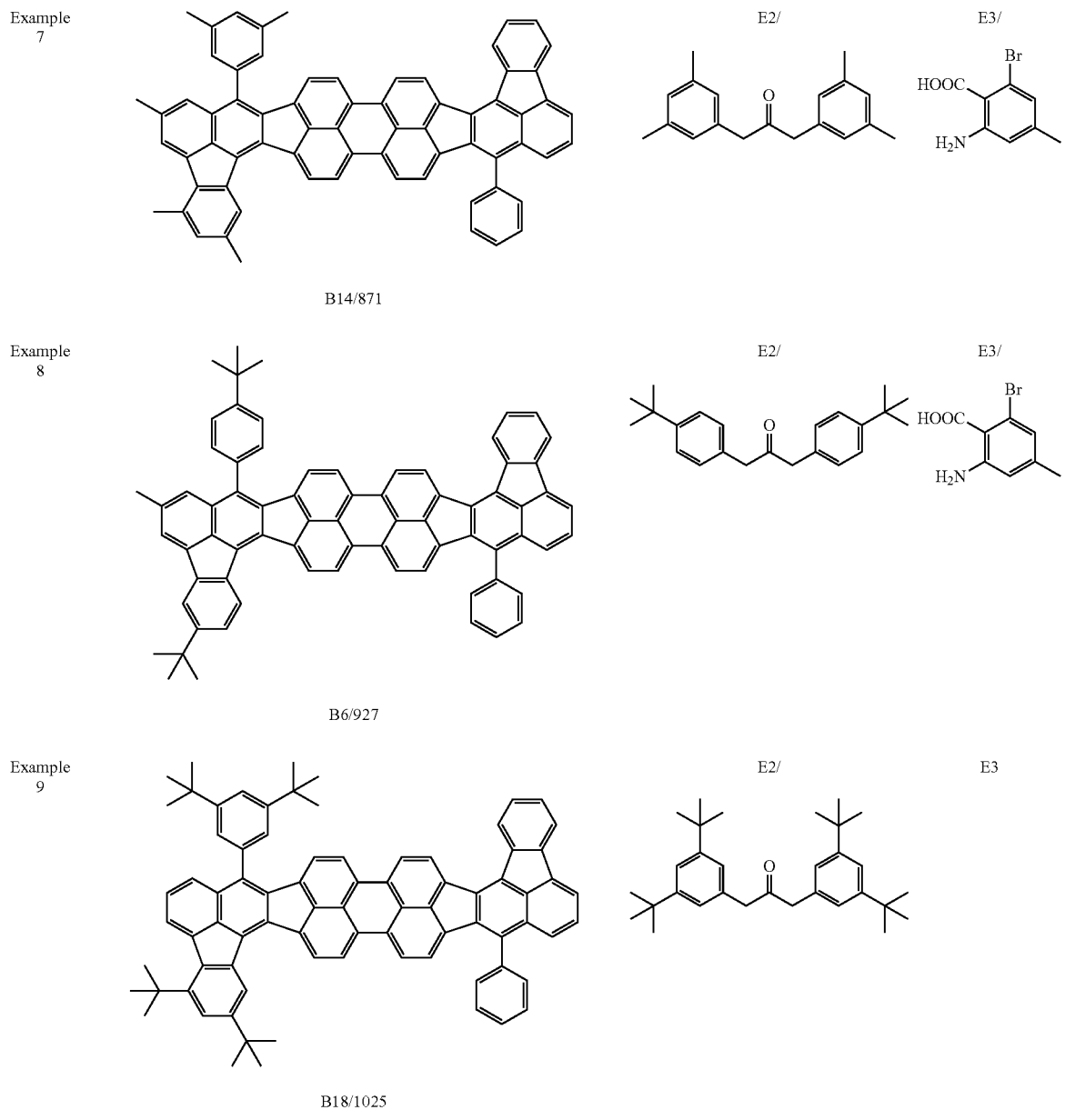
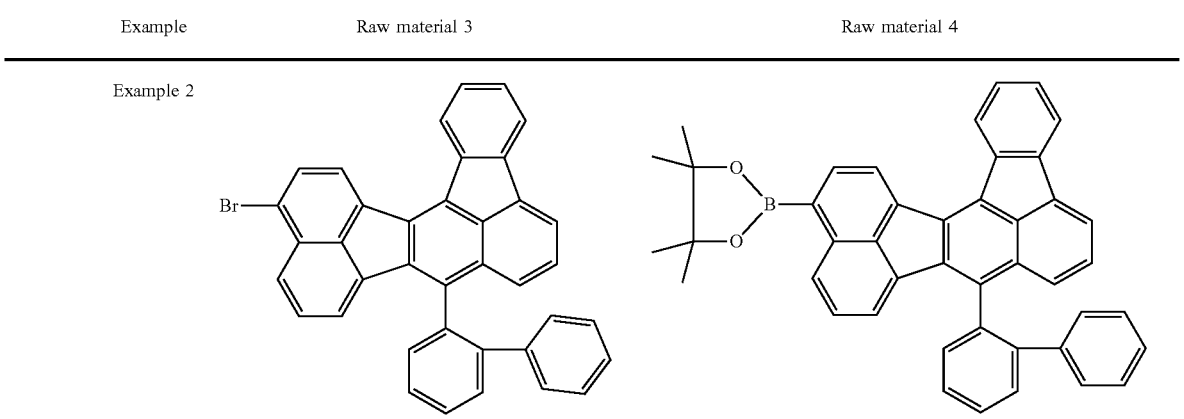

TABLE 3-continued
Example 3
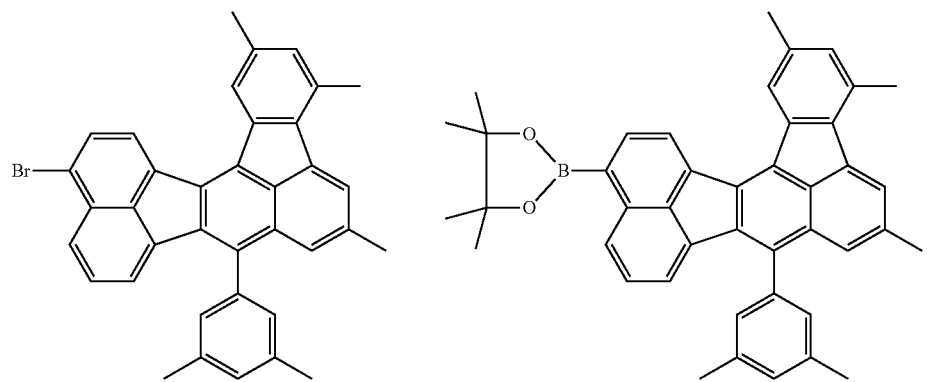
Example 4
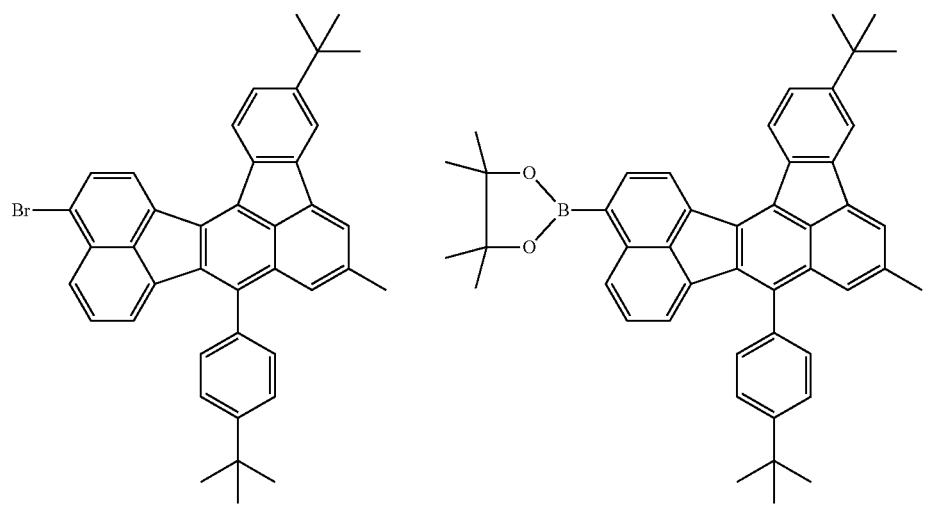
Example 5
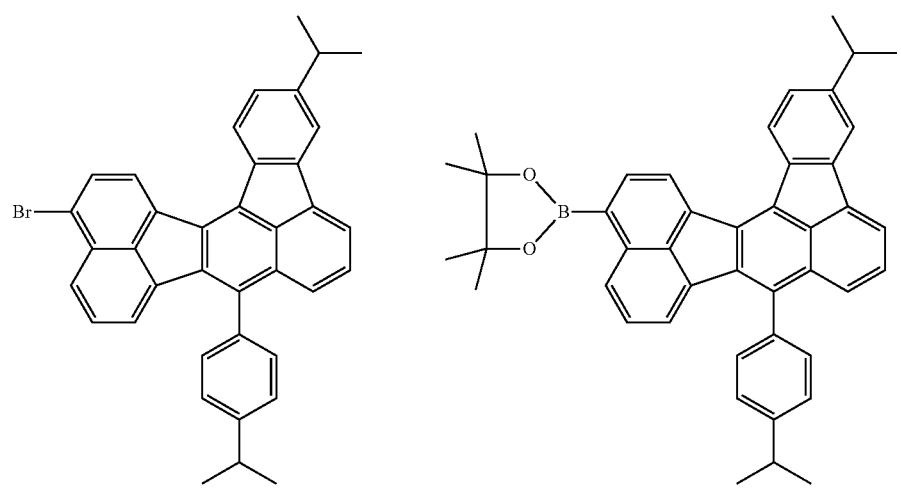

TABLE 3-continued
| Example 6 | 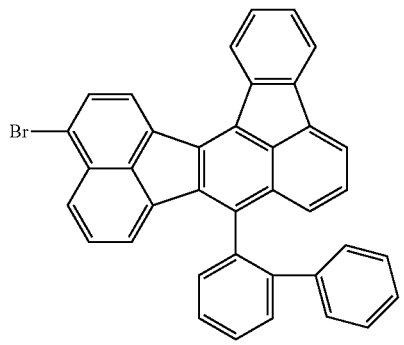 [SMILES: Brc1ccc2c3c1cccc3c1c(-c3ccccc3-c3ccccc3)c3cccc4c5ccccc5c(c34)c21] | E8 |
| Example 7 | 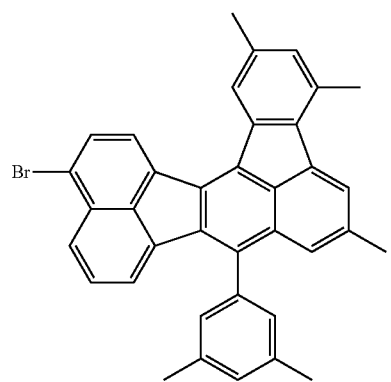 [SMILES: Cc1cc(C)cc(-c2c3cc(C)cc4c5c(C)cc(C)cc5c(c34)c3c4ccc(Br)c5cccc(c23)c54)c1] | E8 |
| Example 8 | 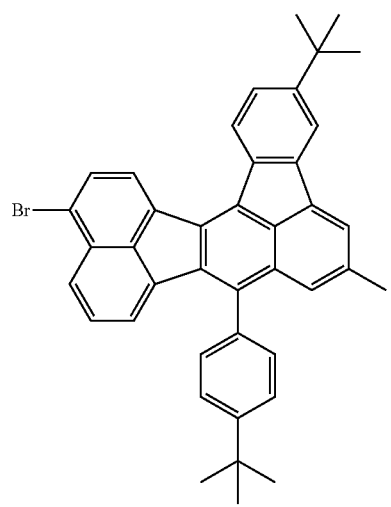 [SMILES: Cc1cc2c(-c3ccc(C(C)(C)C)cc3)c3c4cccc5c(Br)ccc(c54)c3c3c4ccc(C(C)(C)C)cc4c(c1)c23] | E8 |

TABLE 3-continued

| Example 9 | E8 |
|---|---|

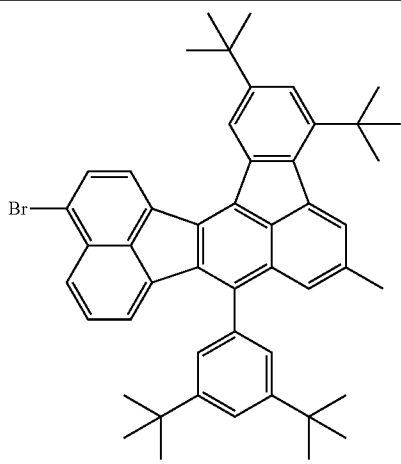

Example 10

Synthesis of Exemplary Compound A5

(1) Synthesis of Compound E13

Compound E13 was synthesized as in Example 1 except that, in the scheme from compound E1 to compound E9 in Example 1, E10 was used instead of the raw material E3.

(2) Synthesis of Exemplary Compound A5

Exemplary compound A5 was synthesized by the following scheme.

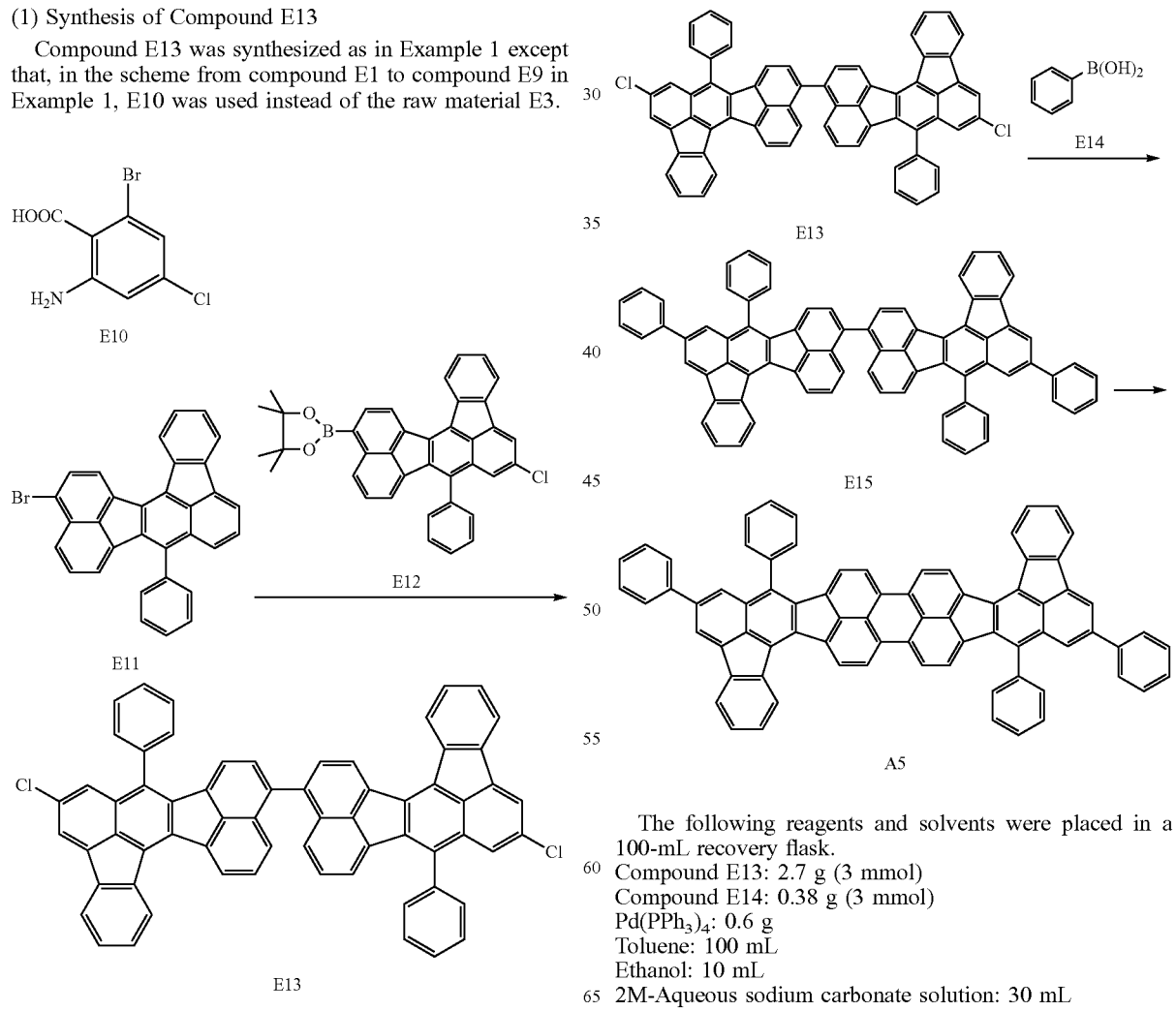

The following reagents and solvents were placed in a 100-mL recovery flask.
Compound E13: 2.7 g (3 mmol)
Compound E14: 0.38 g (3 mmol)
Pd(PPh$_3$)$_4$: 0.6 g
Toluene: 100 mL
Ethanol: 10 mL
2M-Aqueous sodium carbonate solution: 30 mL Next, the resulting reaction solution was heated to 80° C. in a nitrogen stream and stirred at this temperature (80° C.)

for eight hours. After the completion of the reaction, ethanol was added to the resulting reaction solution to precipitate a crystal. The crystal was then separated by filtration and sequentially dispersed and washed in water, ethanol, and heptane. Next, the resulting crystal was dissolved in chlorobenzene under heating, subsequently subjected to hot filtration, and then recrystallized. As a result, 2.1 g of compound E15, which was a red compound, was obtained (yield: 70%).

The following reagents and solvent were placed in a 500-mL reaction container.
Compound E15: 1.9 g (2 mmol)
Trifluoroacetic acid: 20 mL
Methylene chloride: 150 mL Next, the following reagent was placed in the reaction container in a water bath.
BF$_3$·OEt: 4 mL Next, after the reaction solution was stirred for about 10 minutes, 1.0 g of 2,3-dichloro-5,6-dicyano-p-benzoquinone (DDQ) was placed in the reaction container. Subsequently, after the reaction solution was stirred for 10 minutes, 1.0 g of ferrocene was placed in the reaction container in the water bath at 20° C. After stirring was conducted for about five minutes, 150 mL of methanol was added. A red precipitate generated at this time was filtered to obtain a red solid. Next, the solid was dissolved in chlorobenzene and recrystallized with heptane. As a result, 1.2 g of exemplary compound A5 was obtained in the form of a blackish red crystal (yield: 60%).

Exemplary compound A5 was subjected to mass spectrometry by using a MALDI-TOF-MS (Autoflex LRF manufactured by Bruker Corporation).
MALDI-TOF-MS
Actual measured value: m/z=953
Calculated value: $C_{76}H_{40}$=953

Examples 11 to 15

Synthesis of Exemplary Compounds

Exemplary compounds shown in Table 4 were synthesized as in Example 10 except that the raw material E2 in Example 1 and the raw materials E11, E12, and E14 in Example 10 were changed to a raw material 5, a raw material 6, a raw material 7, and a raw material 8, respectively. Table 4 further shows the actual measured value m/z of the results of mass spectrometry performed as in Example 10.

TABLE 4

| Example | Exemplary compound/m/z |
|---|---|
| Example 11 | 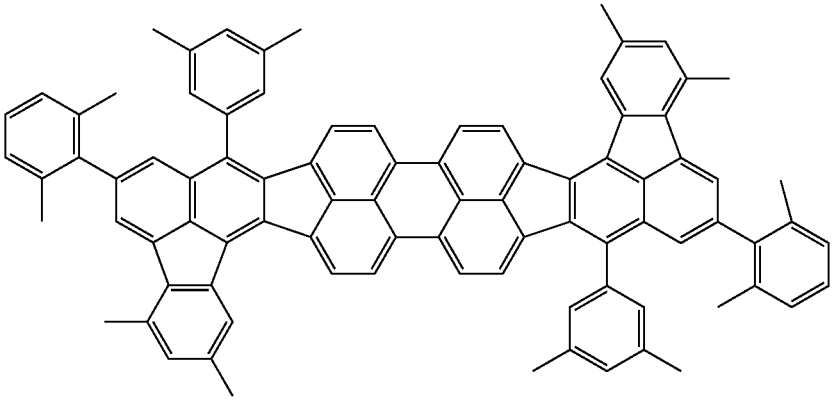<br>B10/1121 |
| Example 12 | 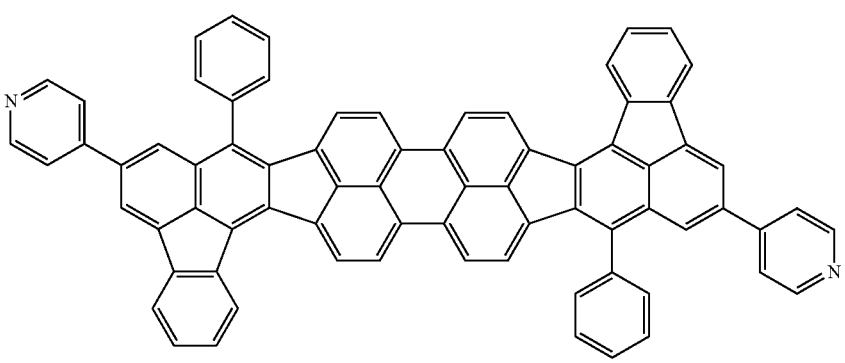<br>C3/955 |

Example 13
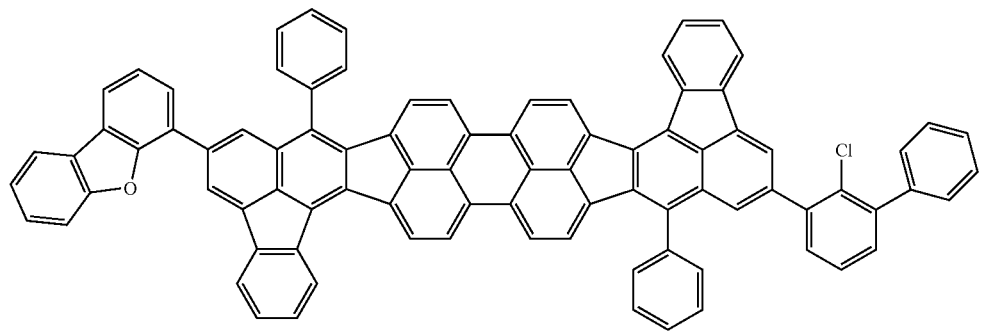
C7/1133
Example 14
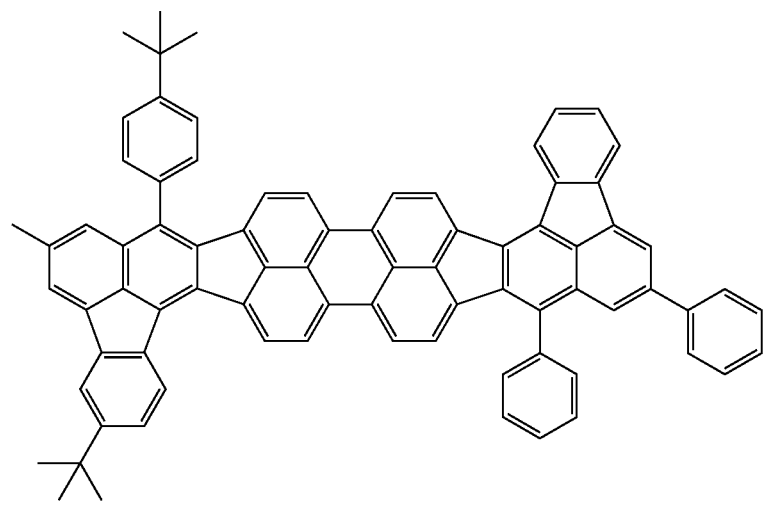
B28/1003
Example 15
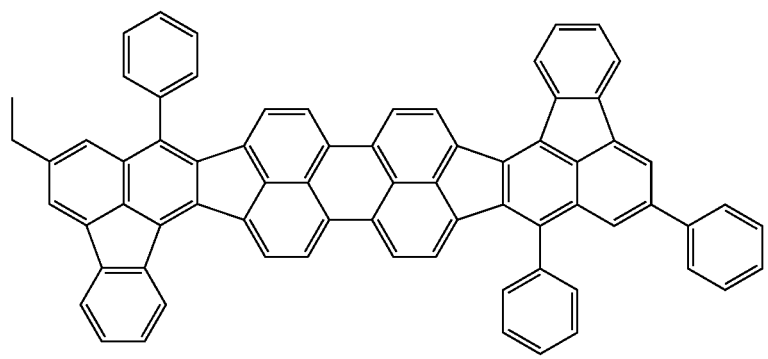
B33/905

TABLE 4-continued
| | Raw material 5 | Raw material 6 |
|---|---|---|
| Example 11 | 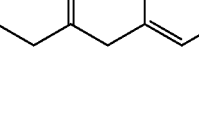 | 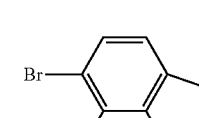 |
| Example 12 | E2 | E11 |
| Example 13 | E2 | E11 |
| Example 14 | E2/ 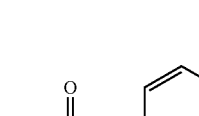 | E11 |
| Example 15 | E2 | E11 |
| | Raw material 7 | Raw material 8 |
|---|---|---|
| Example 11 | | |
| Example 12 | E12 |  |
| | | 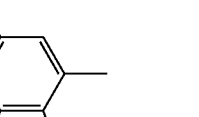 |
| Example 13 | E12 |  |
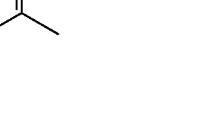

TABLE 4-continued

| Example 14 | E14 |

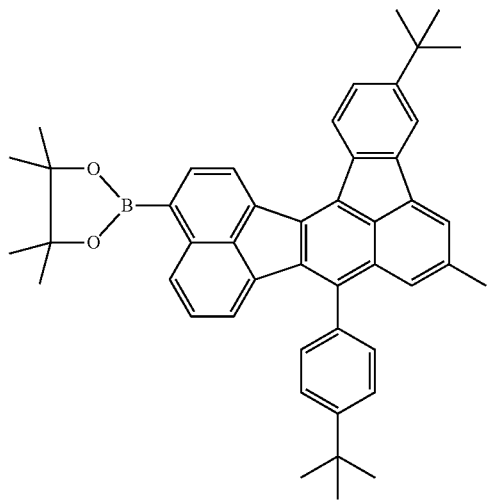

| Example 15 | E14 |

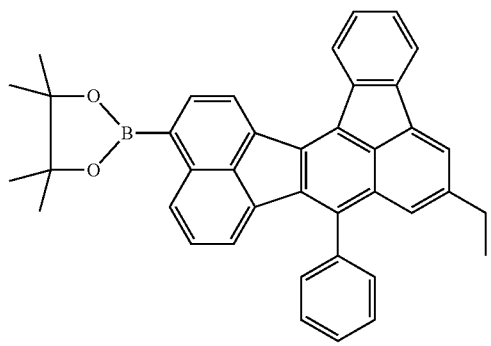 [SMILES: CCc1cc2c(-c3ccccc3)c3c4cccc5c(B6OC(C)(C)C(C)(C)O6)ccc(c54)c3c3c4ccccc4c(c1)c23]

Example 16

A bottom-emission-type organic light-emitting element was produced in which an anode, a hole injection layer, a hole transport layer, an electron blocking layer, a light-emitting layer, a hole blocking layer, an electron transport layer, an electron injection layer, and a cathode were sequentially formed on a substrate.

First, ITO was deposited on a glass substrate, and the resulting ITO film was subjected to a desired pattering to form an ITO electrode (anode). At this time, the film thickness of the ITO electrode was 100 nm. The substrate on which the ITO electrode was formed as described above was used as an ITO substrate in the following steps. Next, the organic compound layers and the electrode layer shown in Table 5 below were successively deposited on the ITO substrate by a resistance heating vacuum vapor deposition in a vacuum chamber at $1.33 \times 10^{-4}$ Pa. At this time, the area of the electrode (metal electrode layer, i.e., cathode) facing the anode was adjusted to 3 $mm^2$.

TABLE 5

| | Material | | | Thickness (nm) |
|---|---|---|---|---|
| Cathode | Al | | | 100 |
| Electron injection layer (EIL) | LiF | | | 1 |
| Electron transport layer (ETL) | ET5 | | | 20 |
| Hole blocking layer (HBL) | ET17 | | | 20 |
| Light-emitting layer (EML) | Host Guest | EM17 A3 | Weight ratio EM17:A3 = 99.7:0.3 | 30 |
| Electron blocking layer (EBL) | HT12 | | | 15 |
| Hole transport layer (HTL) | HT3 | | | 30 |
| Hole injection layer (HIL) | HT16 | | | 5 |

Characteristics of the element produced as described above were measured and evaluated. The light-emitting element had a maximum emission wavelength of 614 nm. Red light with a chromaticity of (X, Y)=(0.65, 0.32) was emitted. The external quantum efficiency (E. Q. E) was 4.9%. Furthermore, a continuous driving test was conducted at a current density of 100 $mA/cm^2$, and the time taken for a rate of degradation of luminance to reach 5% was measured. According to the results, the time exceeded 500 hours. Regarding the specific measurement devices, current-voltage characteristics were measured with a microammeter 4140B manufactured by Hewlett-Packard, and the emission luminance was measured with a luminance colorimeter BM7 manufactured by Topcon Corporation.

Examples 17 to 25 and Comparative Example 1

Organic light-emitting elements were produced by the same method as that used in Example 16 except that the materials of the layers in Example 16 were changed to the compounds shown in Table 6 below. The characteristics of the resulting elements were measured and evaluated as in Example 16. Table 6 shows the results of the measurement.

TABLE 6

| | | | | EML | | | | E.Q.E | Chromaticity |
|---|---|---|---|---|---|---|---|---|---|
| | HIL | HTL | EBL | Host | Guest | HBL | ETL | [%] | coordinates (x, y) |
| Example 17 | HT16 | HT2 | HT11 | EM17 | A5 | ET12 | ET2 | 5.0 | (0.65, 0.33) |
| Example 18 | HT16 | HT3 | HT11 | EM17 | A9 | ET12 | ET2 | 4.9 | (0.66, 0.32) |
| Example 19 | HT16 | HT3 | HT11 | EM16 | A10 | ET10 | ET2 | 4.8 | (0.66, 0.32) |
| Example 20 | HT16 | HT3 | HT11 | EM17 | B2 | ET12 | ET2 | 4.9 | (0.66, 0.32) |
| Example 21 | HT16 | HT3 | HT11 | EM16 | B4 | ET10 | ET2 | 4.8 | (0.66, 0.32) |
| Example 22 | HT2 | HT1 | HT11 | EM16 | B7 | ET12 | ET3 | 4.8 | (0.66, 0.32) |
| Example 23 | HT15 | HT6 | HT11 | EM18 | B14 | ET13 | ET2 | 4.7 | (0.65, 0.33) |
| Example 24 | HT17 | HT6 | HT8 | EM21 | B16 | ET12 | ET2 | 5.2 | (0.66, 0.32) |
| Example 25 | HT15 | HT6 | HT11 | EM16 | B18 | ET15 | ET2 | 5.1 | (0.66, 0.32) |
| Comparative Example 1 | HT16 | HT3 | HT11 | EM17 | Comparative compound 1-A | ET12 | ET2 | 4.3 | (0.64, 0.35) |

Table 6 shows that the chromaticity coordinates in Comparative Example 1 are (0.64, 0.35) and that Examples further expand the color reproduction range with respect to the chromaticity coordinates (0.71, 0.29) in the red range of BT-2020. This is due to the fact that the organic compounds according to the present disclosure emit red light at a longer wavelength.

Example 26

A top-emission-type organic light-emitting element was produced in which an anode, a hole injection layer, a hole transport layer, an electron blocking layer, a first light-emitting layer, a second light-emitting layer, a hole blocking layer, an electron transport layer, an electron injection layer, and a cathode were sequentially formed on a substrate.

Titanium (Ti) was deposited on a glass substrate by a sputtering method to have a thickness of 40 nm. The titanium film was patterned by photolithography to form an anode. At this time, the area of the electrode (metal electrode layer, i.e., cathode) facing the anode was adjusted to 3 mm$^2$.

Subsequently, the substrate which had been cleaned and on which the anode was formed and materials were attached to a vacuum vapor deposition apparatus (manufactured by ULVAC, Inc.), the apparatus was evacuated to $1.33 \times 10^{-4}$ Pa ($1 \times 10^{-6}$ Torr), and UV/ozone cleaning was then conducted. Subsequently, layers were formed so as to have the layer configuration shown in Table 7. Lastly, sealing was conducted in a nitrogen atmosphere.

TABLE 7

| | | Material | | Thickness (nm) |
|---|---|---|---|---|
| Cathode | | Mg | Weight ratio | 10 |
| | | Ag | Mg:Ag = 50:50 | |
| Electron injection layer (EIL) | | LiF | | 1 |
| Electron transport layer (ETL) | | ET2 | | 30 |
| Hole blocking layer (HBL) | | ET12 | | 70 |
| Second light-emitting layer (2nd EML) | Second host | EM1 | Weight ratio | 10 |
| | Second guest (Blue dopant) | BD5 | EM1:BD5 = 99.5:0.5 | |

TABLE 7-continued

|  |  |  | Material | Thickness (nm) |
| --- | --- | --- | --- | --- |
| First light-emitting layer (1st EML) | First host | EM1 | Weight ratio EM1:B2:GD8 = 96.7:0.3:3.0 | 10 |
|  | First guest (Red dopant) | B2 |  |  |
|  | Third guest (Green dopant) | GD8 |  |  |
| Electron blocking layer (EBL) |  | HT7 |  | 10 |
| Hole transport layer (HTL) |  | HT2 |  | 20 |
| Hole injection layer (HIL) |  | HT16 |  | 5 |

Characteristics of the element produced as described above were measured and evaluated. The element exhibited good white-light emission. The chromaticity coordinates of red after transmission through an RGB color filter was estimated from the resulting white light emission spectrum. The chromaticity coordinates of red were (0.65, 0.32).

Examples 27 to 31 and Comparative Example 2

Organic light-emitting elements were produced by the same method as that used in Example 26 except that the materials of the layers in Example 26 were changed to the compounds shown in Table 8 below. The characteristics of the resulting elements were measured and evaluated as in Example 26. Table 8 shows the results of the measurement.

TABLE 8

|  | 1st EML | | | 2nd EML | | Chromaticity coordinates of red (x, y) |
| --- | --- | --- | --- | --- | --- | --- |
|  | First host | First guest | Third guest | Second host | Second guest |  |
| Example 27 | EM1 | A3 | GD8 | EM1 | BD5 | (0.66, 0.32) |
| Example 28 | EM4 | A5 | GD9 | EM4 | BD7 | (0.66, 0.32) |
| Example 29 | EM5 | C3 | GD4 | EM5 | BD4 | (0.65, 0.33) |
| Example 30 | EM1 | B28 | GD7 | EM4 | BD6 | (0.66, 0.32) |
| Example 31 | EM11 | C7 | GD4 | EM11 | BD6 | (0.66, 0.32) |
| Comparative Example 2 | EM1 | Comparative compound 1-A | GD4 | EM1 | BD6 | (0.64, 0.34) |

Table 8 shows that the chromaticity coordinates of red in Comparative Example 2 are (0.64, 0.34) and that Examples further expand the color reproduction range with respect to the chromaticity coordinates (0.71, 0.29) in the red range of BT-2020. This is due to the fact that the organic compounds according to the present disclosure emit red light at a longer wavelength.

The organic compound according to the present disclosure can emit red light having a high color purity. In addition, the purity of the organic compound according to the present disclosure can be enhanced, and the organic compound according to the present disclosure can provide an organic light-emitting element having a high light emission efficiency and good driving durability.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-187929 filed Oct. 3, 2018, which is hereby incorporated by reference herein in its entirety.

What is claimed is:

1. An organic compound represented by formula

[1]

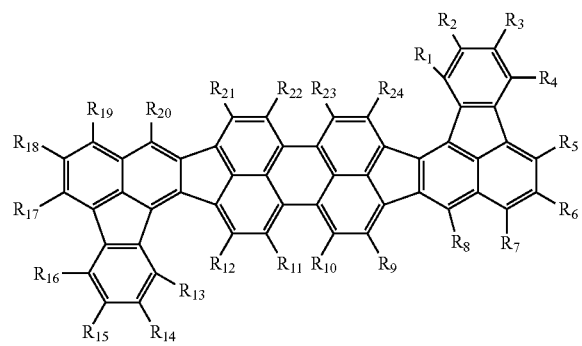

in the formula [1], $R_1$ to $R_{24}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

2. The organic compound according to claim 1, wherein $R_1$ to $R_{24}$ are each independently selected from the group consisting of a hydrogen atom, a substituted or unsubstituted alkyl group having 1 to 10 carbon atoms, and a substituted or unsubstituted aryl group having 6 to 18 carbon atoms.

3. The organic compound according to claim 1, wherein at least two selected from $R_6$, $R_8$, $R_{18}$, and $R_{20}$ are each independently selected from the group consisting of a halogen atom, a substituted or unsubstituted alkyl group having 1 to 10 carbon atoms, a substituted or unsubstituted alkoxy group having 1 to 10 carbon atoms, a substituted or unsubstituted amino group, a substituted or unsubstituted aryl group having 6 to 18 carbon atoms, a substituted or unsubstituted heterocyclic group having 3 to 15 carbon atoms, a substituted or unsubstituted aryloxy group, a silyl group, and a cyano group.

4. The organic compound according to claim 1, wherein at least two selected from $R_6$, $R_8$, $R_{18}$, and $R_{20}$ are each independently selected from the group consisting of a substituted or unsubstituted alkyl group having 1 to 10 carbon atoms and a substituted or unsubstituted aryl group having 6 to 18 carbon atoms.

5. The organic compound according to claim 1, wherein the aryl group has a substituent at an ortho position of the aryl group.

6. The organic compound according to claim 1, wherein at least two selected from $R_6$, $R_8$, $R_{18}$, and $R_{20}$ are each a substituted or unsubstituted phenyl group.

7. The organic compound according to claim 1, wherein the organic compound consists of carbon with an $sp^2$ hybrid orbital and hydrogen.

8. An organic light-emitting element comprising:
a first electrode;
a second electrode; and
an organic compound layer disposed between the first electrode and the second electrode,
wherein the organic compound layer includes a layer that contains the organic compound according to claim 1.

9. The organic light-emitting element according to claim 8, wherein the layer that contains the organic compound is a light-emitting layer.

10. The organic light-emitting element according to claim 9, wherein the organic light-emitting element emits red light.

11. The organic light-emitting element according to claim 9, wherein the organic compound layer further includes another light-emitting layer stacked on the light-emitting layer, and the other light-emitting layer emits light having a color different from a color of light emitted from the light-emitting layer.

12. The organic light-emitting element according to claim 11, wherein the organic light-emitting element emits white light.

13. A display device comprising a plurality of pixels,
wherein at least one of the pixels includes the organic light-emitting element according to claim 8 and an active element connected to the organic light-emitting element.

14. The display device according to claim 13, further comprising a color filter.

15. An image display device comprising:
an input unit configured to input image information; and
a display unit configured to output an image,
wherein display unit includes the display device according to claim 13.

16. An imaging device comprising:
an optical unit having a plurality of lenses;
an imaging element that receives light that has passed through the optical unit; and
a display unit,
wherein the display unit is configured to display information captured by the imaging element and includes the display device according to claim 13.

17. An electronic device comprising:
a housing;
a communication unit that communicates with an outside; and
a display unit,
wherein the display unit is the display device according to claim 13.

18. An illumination device comprising:
a light source; and
a light diffusion unit or an optical filter,
wherein the light source includes the organic light-emitting element according to claim 8.

19. An illumination device comprising:
the organic light-emitting element according to claim 8; and
a power supply circuit connected to the organic light-emitting element.

20. A moving object comprising:
a body; and
a lighting fixture disposed on the body,
wherein the lighting fixture includes the organic light-emitting element according to claim 8.

* * * * *